US010758222B2

(12) United States Patent
Saliman et al.

(10) Patent No.: US 10,758,222 B2
(45) Date of Patent: *Sep. 1, 2020

(54) MENISCUS REPAIR

(71) Applicant: CETERIX ORTHOPAEDICS, INC., Fremont, CA (US)

(72) Inventors: Justin D. Saliman, Beverly Hills, CA (US); Brad S. Culbert, Rancho Santa Margarita, CA (US); Alexander Jasso, Portland, OR (US); Michael J. Hendricksen, Redwood City, CA (US); John G. McCutcheon, Menlo Park, CA (US); Christopher P. Bender, Oakland, CA (US); Michael Murillo, Menlo Park, CA (US)

(73) Assignee: Ceterix Orthopaedics, Inc., Fremont, CA (US)

( * ) Notice: Subject to any disclaimer, the term of this patent is extended or adjusted under 35 U.S.C. 154(b) by 265 days.

This patent is subject to a terminal disclaimer.

(21) Appl. No.: 15/866,343

(22) Filed: Jan. 9, 2018

(65) Prior Publication Data
US 2018/0125479 A1    May 10, 2018

Related U.S. Application Data

(63) Continuation of application No. 13/247,892, filed on Sep. 28, 2011, now Pat. No. 9,861,354.
(Continued)

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0482* (2013.01); *A61B 17/062* (2013.01);
(Continued)

(58) Field of Classification Search
CPC . A61B 17/04; A61B 17/0469; A61B 17/0483; A61B 17/0482; A61B 17/0491;
(Continued)

(56) References Cited

U.S. PATENT DOCUMENTS

| 1,037,864 A | 9/1912 | Carlson et al. |
| 1,815,725 A | 7/1931 | Pilling et al. |

(Continued)

FOREIGN PATENT DOCUMENTS

| CN | 201263696 Y | 7/2009 |
| CN | 101961256 A | 2/2011 |

(Continued)

OTHER PUBLICATIONS

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.
(Continued)

*Primary Examiner* — Christopher L Templeton
(74) *Attorney, Agent, or Firm* — Norman F. Hainer, Jr.

(57) ABSTRACT

Methods for repairing a meniscus, and particularly a torn meniscus. A method of repairing a meniscus may include using a suture passer to pass a suturing element from the region between the superior surface of the meniscus and the femoral condyle, through the meniscus tissue, into the region between the inferior surface of the meniscus and the tibial plateau, across the inferior surface of the meniscus, and back to the superior surface of the meniscus, without deeply penetrating the posterior capsular region of the knee. Equivalently, the suture element may be passed from the inferior surface of the meniscus to the superior surface and back to the inferior surface.

19 Claims, 79 Drawing Sheets

Related U.S. Application Data

(60) Provisional application No. 61/483,200, filed on May 6, 2011, provisional application No. 61/511,922, filed on Jul. 26, 2011.

(51) Int. Cl.
 *A61B 17/06* (2006.01)
 *A61B 17/29* (2006.01)

(52) U.S. Cl.
 CPC ....... *A61B 17/0485* (2013.01); *A61B 17/0625* (2013.01); *A61B 2017/0472* (2013.01); *A61B 2017/0496* (2013.01); *A61B 2017/06009* (2013.01); *A61B 2017/06014* (2013.01); *A61B 2017/06042* (2013.01); *A61B 2017/06176* (2013.01); *A61B 2017/2927* (2013.01)

(58) Field of Classification Search
 CPC ...... A61B 2014/047; A61B 2017/0475; A61B 2017/0477
 See application file for complete search history.

(56) References Cited

U.S. PATENT DOCUMENTS

| | | |
|---|---|---|
| 2,738,790 A | 3/1956 | Todt, Sr. et al. |
| 2,748,773 A | 6/1956 | Vacheresse, Jr. |
| 3,470,875 A | 10/1969 | Johnson |
| 3,580,256 A | 5/1971 | Wilkinson et al. |
| 3,807,407 A | 4/1974 | Schweizer |
| 3,842,840 A | 10/1974 | Schweizer |
| 3,901,244 A | 8/1975 | Schweizer |
| 4,021,896 A | 5/1977 | Stierlein |
| 4,109,658 A | 8/1978 | Hughes |
| 4,164,225 A | 8/1979 | Johnson et al. |
| 4,236,470 A | 12/1980 | Stenson |
| 4,345,601 A | 8/1982 | Fukuda |
| 4,440,171 A | 4/1984 | Nomoto et al. |
| 4,484,580 A | 11/1984 | Nomoto et al. |
| 4,553,543 A | 11/1985 | Amarasinghe |
| 4,605,002 A | 8/1986 | Rebuffat |
| 4,621,640 A | 11/1986 | Mulhollan et al. |
| 4,706,666 A | 11/1987 | Sheets |
| 4,836,205 A | 6/1989 | Barrett |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,059,206 A | 10/1991 | Winters |
| 5,112,344 A | 5/1992 | Petros |
| 5,129,912 A | 7/1992 | Noda et al. |
| 5,139,520 A | 8/1992 | Rosenberg |
| 5,156,608 A | 10/1992 | Troidl et al. |
| 5,193,473 A | 3/1993 | Asao et al. |
| 5,211,650 A | 5/1993 | Noda |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,254,126 A | 10/1993 | Filipi et al. |
| 5,281,237 A | 1/1994 | Gimpelson |
| 5,312,422 A | 5/1994 | Trott |
| 5,320,633 A | 6/1994 | Allen et al. |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Failla et al. |
| 5,368,601 A | 11/1994 | Sauer et al. |
| 5,383,877 A | 1/1995 | Clarke |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,352 A | 4/1995 | Weston |
| 5,405,532 A | 4/1995 | Loew et al. |
| 5,431,666 A | 7/1995 | Sauer et al. |
| 5,431,669 A | 7/1995 | Thompson et al. |
| 5,437,681 A | 8/1995 | Meade et al. |
| 5,454,823 A | 10/1995 | Richardson et al. |
| 5,454,834 A | 10/1995 | Boebel et al. |
| 5,468,251 A | 11/1995 | Buelna |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,756 A | 4/1996 | Hasson |
| 5,507,757 A | 4/1996 | Sauer et al. |
| 5,520,702 A | 5/1996 | Sauer et al. |
| 5,522,820 A | 6/1996 | Caspari et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,601,576 A | 2/1997 | Garrison |
| 5,607,435 A | 3/1997 | Sachdeva et al. |
| 5,616,131 A | 4/1997 | Sauer et al. |
| 5,618,290 A | 4/1997 | Toy et al. |
| 5,626,588 A | 5/1997 | Sauer et al. |
| 5,632,748 A | 5/1997 | Beck et al. |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,665,096 A | 9/1997 | Yoon |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,797,958 A | 8/1998 | Yoon |
| 5,800,445 A | 9/1998 | Ratcliff et al. |
| 5,814,054 A | 9/1998 | Kortenbach et al. |
| 5,814,069 A | 9/1998 | Schulze et al. |
| 5,824,009 A | 10/1998 | Fukuda et al. |
| 5,827,300 A | 10/1998 | Fleega |
| 5,843,100 A | 12/1998 | Meade |
| 5,843,126 A | 12/1998 | Jameel |
| 5,865,836 A | 2/1999 | Miller |
| 5,871,490 A | 2/1999 | Schulze et al. |
| 5,876,411 A | 3/1999 | Kontos |
| 5,876,412 A | 3/1999 | Piraka |
| 5,895,393 A | 4/1999 | Pagedas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,910,148 A | 6/1999 | Reimels et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 5,997,554 A | 12/1999 | Thompson |
| 6,039,753 A | 3/2000 | Meislin |

(56) References Cited

U.S. PATENT DOCUMENTS

| | | |
|---|---|---|
| 6,042,601 A | 3/2000 | Smith |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |
| 6,099,568 A | 8/2000 | Simonian et al. |
| 6,113,610 A | 9/2000 | Poncet |
| 6,126,666 A | 10/2000 | Trapp et al. |
| 6,129,741 A | 10/2000 | Wurster et al. |
| 6,139,556 A | 10/2000 | Kontos |
| 6,152,934 A | 11/2000 | Harper et al. |
| 6,159,224 A | 12/2000 | Yoon |
| 6,190,396 B1 | 2/2001 | Whitin et al. |
| 6,217,592 B1 | 4/2001 | Freda et al. |
| 6,221,085 B1 | 4/2001 | Djurovic |
| 6,231,606 B1 | 5/2001 | Graf et al. |
| 6,238,414 B1 | 5/2001 | Griffiths |
| 6,264,694 B1 | 7/2001 | Weiler |
| 6,277,132 B1 | 8/2001 | Brhel |
| 6,322,570 B1 | 11/2001 | Matsutani et al. |
| 6,325,808 B1 | 12/2001 | Bernard et al. |
| 6,332,889 B1 | 12/2001 | Sancoff et al. |
| 6,355,050 B1 | 3/2002 | Andreas et al. |
| 6,368,334 B1 | 4/2002 | Sauer |
| 6,368,343 B1 | 4/2002 | Bonutti et al. |
| 6,443,963 B1 | 9/2002 | Baldwin et al. |
| 6,454,778 B2 | 9/2002 | Kortenbach |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,605,096 B1 | 8/2003 | Ritchart |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |
| 6,641,592 B1 | 11/2003 | Sauer et al. |
| 6,719,764 B1 | 4/2004 | Gellman et al. |
| 6,719,765 B2 | 4/2004 | Bonutti |
| 6,723,107 B1 | 4/2004 | Skiba et al. |
| 6,770,084 B1 | 8/2004 | Bain et al. |
| 6,833,005 B1 | 12/2004 | Mantas |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |
| 6,936,054 B2 | 8/2005 | Chu |
| 6,972,027 B2 | 12/2005 | Fallin et al. |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,153,312 B1 | 12/2006 | Torrie et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,442,198 B2 | 10/2008 | Gellman et al. |
| 7,481,817 B2 | 1/2009 | Sauer |
| 7,481,826 B2 | 1/2009 | Cichocki |
| 7,491,212 B2 | 2/2009 | Sikora et al. |
| 7,588,583 B2 | 9/2009 | Hamilton et al. |
| 7,594,922 B1 | 9/2009 | Goble et al. |
| 7,608,084 B2 | 10/2009 | Oren et al. |
| 7,632,284 B2 | 12/2009 | Martinek et al. |
| 7,674,276 B2 | 3/2010 | Stone et al. |
| 7,717,927 B2 | 5/2010 | Hahn et al. |
| 7,722,630 B1 | 5/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,938,839 B2 | 5/2011 | DiFrancesco et al. |
| 7,951,147 B2 | 5/2011 | Privitera et al. |
| 7,951,157 B2 | 5/2011 | Gambale |
| 7,951,159 B2 | 5/2011 | Stokes et al. |
| 7,972,344 B2 | 7/2011 | Murray et al. |
| 8,298,230 B2 | 10/2012 | Sutter et al. |
| 8,394,112 B2 | 3/2013 | Nason |
| 8,398,673 B2 | 3/2013 | Hinchliffe et al. |
| 8,449,533 B2 | 5/2013 | Saliman et al. |
| 8,465,505 B2 | 6/2013 | Murillo et al. |
| 8,500,809 B2 | 8/2013 | Saliman |
| 8,562,631 B2 | 10/2013 | Saliman |
| 8,632,563 B2 | 1/2014 | Nagase et al. |
| 8,647,354 B2 | 2/2014 | Domingo |
| 8,663,253 B2 | 3/2014 | Saliman |
| 8,702,731 B2 | 4/2014 | Saliman |
| 8,808,299 B2 | 8/2014 | Saliman et al. |
| 8,821,518 B2 | 9/2014 | Saliman |
| 8,888,848 B2 | 11/2014 | Saliman et al. |
| 8,911,456 B2 | 12/2014 | McCutcheon et al. |
| 8,920,441 B2 | 12/2014 | Saliman et al. |
| 9,011,454 B2 | 4/2015 | Hendrickson et al. |
| 9,211,119 B2 | 12/2015 | Hendrickson et al. |
| 9,247,934 B2 | 2/2016 | Murillo et al. |
| 9,247,935 B2 | 2/2016 | George et al. |
| 9,314,234 B2 | 4/2016 | Hirotsuka et al. |
| 9,332,980 B2 | 5/2016 | George et al. |
| 9,492,162 B2 | 11/2016 | Murillo et al. |
| 9,700,299 B2 | 7/2017 | Saliman et al. |
| 9,848,868 B2 | 12/2017 | Saliman |
| 9,861,354 B2 | 1/2018 | Saliman et al. |
| 9,913,638 B2 | 3/2018 | Saliman et al. |
| 2001/0041938 A1 | 11/2001 | Hein |
| 2002/0169477 A1 | 11/2002 | Demopulos et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0078617 A1 | 4/2003 | Schwartz et al. |
| 2003/0181926 A1 | 9/2003 | Dana et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0117014 A1 | 6/2004 | Bryant |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0043746 A1 | 2/2005 | Pollak et al. |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0178680 A1 | 8/2006 | Beverly et al. |
| 2006/0282098 A1 | 12/2006 | Shelton et al. |
| 2007/0032799 A1 | 2/2007 | Pantages et al. |
| 2007/0038230 A1 | 2/2007 | Stone et al. |

(56) References Cited

U.S. PATENT DOCUMENTS

| | | |
|---|---|---|
| 2007/0156174 A1 | 7/2007 | Kaiser et al. |
| 2007/0185532 A1 | 8/2007 | Stone et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2008/0027468 A1 | 1/2008 | Fenton et al. |
| 2008/0086147 A1 | 4/2008 | Knapp |
| 2008/0091219 A1 | 4/2008 | Marshall et al. |
| 2008/0097482 A1 | 4/2008 | Bain et al. |
| 2008/0097489 A1 | 4/2008 | Goldfarb et al. |
| 2008/0140091 A1 | 6/2008 | DeDeyne et al. |
| 2008/0140094 A1 | 6/2008 | Schwartz et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0275553 A1 | 11/2008 | Wolf et al. |
| 2008/0294256 A1 | 11/2008 | Hagan et al. |
| 2009/0012520 A1 | 1/2009 | Hixson et al. |
| 2009/0012538 A1* | 1/2009 | Saliman ............. A61B 17/0491 606/145 |
| 2009/0018554 A1 | 1/2009 | Thorne et al. |
| 2009/0062816 A1 | 3/2009 | Weber |
| 2009/0062819 A1 | 3/2009 | Burkhart et al. |
| 2009/0105729 A1 | 4/2009 | Zentgraf |
| 2009/0105751 A1 | 4/2009 | Zentgraf |
| 2009/0112232 A1 | 4/2009 | Crainich et al. |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1 | 11/2009 | Le et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0217286 A1 | 8/2010 | Gerber et al. |
| 2010/0228271 A1 | 9/2010 | Marshall et al. |
| 2010/0241142 A1 | 9/2010 | Akyuz et al. |
| 2010/0249806 A1 | 9/2010 | Oren et al. |
| 2010/0249809 A1 | 9/2010 | Singhatat et al. |
| 2010/0256564 A1 | 10/2010 | Park |
| 2010/0280530 A1 | 11/2010 | Hashiba |
| 2010/0305581 A1 | 12/2010 | Hart |
| 2010/0305583 A1 | 12/2010 | Baird et al. |
| 2011/0022061 A1 | 1/2011 | Orphanos et al. |
| 2011/0022063 A1 | 1/2011 | McClurg et al. |
| 2011/0028998 A1 | 2/2011 | Adams et al. |
| 2011/0060350 A1 | 3/2011 | Powers et al. |
| 2011/0071563 A1 | 3/2011 | Magliani |
| 2011/0087246 A1 | 4/2011 | Saliman et al. |
| 2011/0100173 A1 | 5/2011 | Stone et al. |
| 2011/0112555 A1 | 5/2011 | Overes et al. |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0251626 A1 | 10/2011 | Wyman et al. |
| 2011/0270306 A1 | 11/2011 | Denham et al. |
| 2012/0101524 A1 | 4/2012 | Bennett |
| 2012/0303046 A1 | 11/2012 | Stone et al. |
| 2013/0072948 A1 | 3/2013 | States, III et al. |
| 2013/0253536 A1 | 9/2013 | Harris et al. |
| 2014/0222034 A1 | 8/2014 | Saliman |
| 2015/0034694 A1 | 2/2015 | Cappola |
| 2015/0073442 A1 | 3/2015 | Saliman et al. |
| 2015/0209029 A1 | 7/2015 | Hendricksen et al. |
| 2015/0257756 A1 | 9/2015 | Sauer |
| 2015/0297215 A1 | 10/2015 | Hendricksen et al. |
| 2015/0313589 A1 | 11/2015 | Hendricksen et al. |
| 2016/0192926 A1 | 7/2016 | Hendricksen et al. |
| 2016/0220244 A1 | 8/2016 | Murillo et al. |
| 2016/0242765 A1 | 8/2016 | George et al. |
| 2016/0302789 A1 | 10/2016 | Hirotsuka et al. |
| 2017/0020512 A1 | 1/2017 | Murillo et al. |
| 2017/0027558 A1 | 2/2017 | Murillo et al. |
| 2017/0119372 A1 | 5/2017 | Peter et al. |
| 2018/0199931 A1 | 7/2018 | Saliman et al. |

FOREIGN PATENT DOCUMENTS

| | | |
|---|---|---|
| CN | 103298503 A | 9/2013 |
| CN | 103717149 A | 4/2014 |
| EP | 0647431 A2 | 4/1995 |
| EP | 2030575 A1 | 3/2009 |
| EP | 2184015 A2 | 5/2010 |
| EP | 2081481 B1 | 11/2015 |
| JP | 3032847 U | 3/1991 |
| JP | 2009138029 A | 6/2009 |
| JP | 2009538190 | 11/2009 |
| SU | 376089 A | 4/1973 |
| SU | 728848 A1 | 4/1980 |
| SU | 1725847 A1 | 4/1992 |
| WO | WO 92/05828 A1 | 4/1992 |
| WO | WO 95/13021 A1 | 5/1995 |
| WO | WO98/11825 A1 | 3/1998 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO01/56478 A1 | 8/2001 |
| WO | WO 02/07607 A1 | 1/2002 |
| WO | WO 02/096296 A1 | 12/2002 |
| WO | WO 03/028532 A2 | 4/2003 |
| WO | WO 03/077771 A1 | 9/2003 |
| WO | WO 2006/001040 A1 | 1/2006 |
| WO | WO 2006/007399 A1 | 1/2006 |
| WO | WO 2006/040562 A1 | 4/2006 |
| WO | WO 2010/036227 A1 | 4/2010 |
| WO | WO 2010/050910 A1 | 5/2010 |
| WO | WO 2010/141695 A1 | 12/2010 |
| WO | WO 2011/057245 A2 | 5/2011 |

OTHER PUBLICATIONS

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filing date and any foreign priority date) 2007, 22 pages.

ArthroCare® Sportsmedicine, Sunnyvale, CA, SmartStitch® Suture Passing System with the PerfectPasserTM, Product brochure, (year of pub. sufficiently earlier than effective US filing date and any foreign priority date) 2006, 4 pages.

Baena et al.; Inside-out medial meniscus suture: an analysis of the risk of injury to the popliteal neurovascular bundle; Arthroscopy; 27(4):516-21; Apr. 2011.

BiPass(TM) Suture Punch, Biomet® Sports Medicine, Inc., accessed Feb. 29, 2008 at <http://www.arthrotek.com/prodpage.cfm?c=0A05 &p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Ceterix; Novocut suture manager; retrieved from the internet (https://web.archive.org/web/20150314071511/http://www.ceterix.com:80/im-a-physician/products/) on Oct. 11, 2017; 1 page; Mar. 12, 2015.

(56) References Cited

OTHER PUBLICATIONS

Ceterix; Novocut suture manager; retrieved from the internet (https://www.youtube.com/watch?v=6txqBJxvnuA) on Oct. 11, 2017; 1 page; Mar. 5, 2015.
Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2 pgs.
Depuy Mitek, Inc; Raynham, MA, "Versalok Surgical Technique for Rotator Cuff Repair: The next generation in rotator cuff repair," Product brochure, (year of pub. sufficiently earlier than effective US filing date and any foreign priority date) 2007, 18 pages.
Dictionary.com; Adjacent (definition); 5 pgs.; retrieved from the internet (http://www.dictionary.com/browse/adjacent) on Apr. 5, 2016.
Duerig, T. et al., "An overview of nitinol medical applications" Materials Science and Engineering A273-275, pp. 149-160; May 1999.
Eggli et al.; Long-term results of arthroscopic meniscal repair. An analysis of isolated tears; Am J Sports Med; 23(6):715-20; Nov.-Dec. 1995.
Grant et al.; Comparison of inside-out and all-inside techniques for the repair of isolated meniscal tears: a systematic review; Am J Sports Med preview; Jul. 7, 2011; pp. 1-10.
Klecker et al.; The aberrant anterior tibial artery: magnetic resonance appearance, prevalence, and surgical implications; Am J Sports Med; 36(4):720-7; Apr. 2008.
Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.
Lozano et al.; All-inside meniscus repair: a systematic review; Clin Orthop Relat Res; 455:134-41; Feb. 2007.
Ma et al; "Biomechanical Evaluation of Arthroscopic Rotator Cuff Stitches," J Bone Joint Surg Am, Jun. 2004; vol. 86(6):1211-1216.
Medsfera; Suturing devices; accessed Dec. 4, 2012 at <http://www.medsfera.ru/shiv.html> 13 pages.
Nho et al; "Biomechanical fixation in Arthroscopic Rotator Cuff Repair," Arthroscopy: J of Arthroscop and Related Surg; vol. 23. No. 1, Jan. 2007: pp. 94-102.
Nord et al.; Posterior lateral meniscal root tears and meniscal repair; Orthopedics Today; 5 pgs; Nov. 2010; retrieved from the internet on Aug. 21, 2014 (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).
Paxton et al.; Meniscal repair versus partial meniscectomy: a systematic review comparing reoperation rates and clinical outcomes; Arthroscopy; 27(9):1275-88; Sep. 2011.
Pujol et al.; Meniscal healing after meniscal repair: a CT arthrography assessment; Am J Sports Med; 36(8):1489-95; Aug. 2008.
Rimmer et al.; Failure Strength of Different Meniscal Suturing Techniques; Arthroscopy: The Journal of Arthroscopic and Related Surgery; vol. 11; No. 2; pp. 146-150; Apr. 1995.
Rockborn et al.; Results of open meniscus repair. Long-term follow-up study with a matched uninjured control group; J Bone Joint Surg Br; 82(4):494-8; May 2000.
Schneeberger, et al; "Mechanical Strength of Arthroscopic Rotator Cuff Repair Techniques: An in Vitro Study," J Bone Joint Surg Am., Dec. 2002; 84:2152-2160.
Small et al.; Avoiding Complications in Meniscal Repair; Techniques in Orthopaedics; 8(2):70-75; Summer (Jun.-Aug.) 1993.
Smith&Nephew; Fast-Fix Meniscal Repair System (product webpage); 4 pgs.; downloaded Nov. 21, 2011 (http://endo.smith-nephew.com/fr/node.asp?NodeId=3562).
Stärke et al.; Current Concepts: Meniscal Repair; Arthroscopy: The Journal of Arthroscopic and Related Surgery; vol. 25; Issue 9; pp. 1033-1044; Sep. 2009.
Strobel; Manual of Arthroscopic Surgery (1st Edition); Springer Verlag, Hiedelberg © 2002; pp. 127-129; Dec. 15, 2001.
USS SportsMedicine ArthoSew™ Single Use Automated Suturing Device with 8.6 mm ArthroPort Cannula Set, Instructions for Use, <http:www.uss-sportsmed.com/imageServer.aspx? contentID=5020&contenttype=application/pdf> accessed Apr. 25, 2007, 2 pages.
USS SportsMedicine ArthroSew™ Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.
Saliman; U.S. Appl. No. 15/853,531 entitled "Suture methods for forming locking loops stitches," filed Dec. 22, 2017.
Brazilian Informal Translation The Preliminary Of The Office Action—Application No. BR112013028339-4.

\* cited by examiner

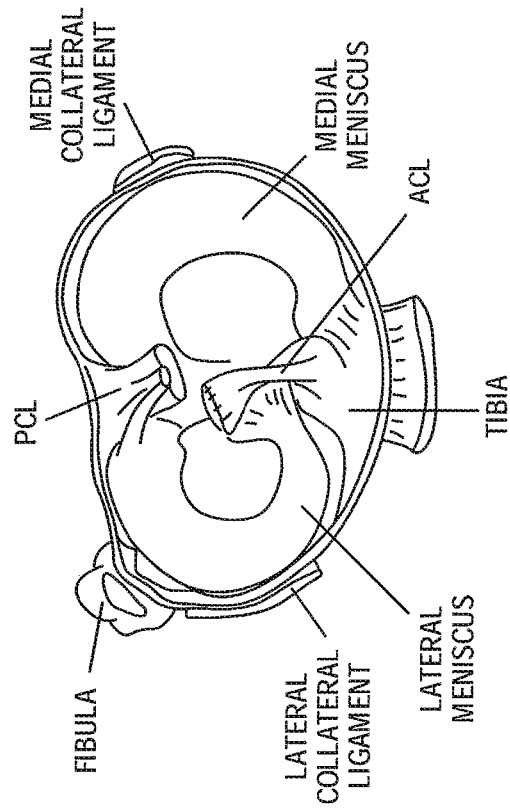
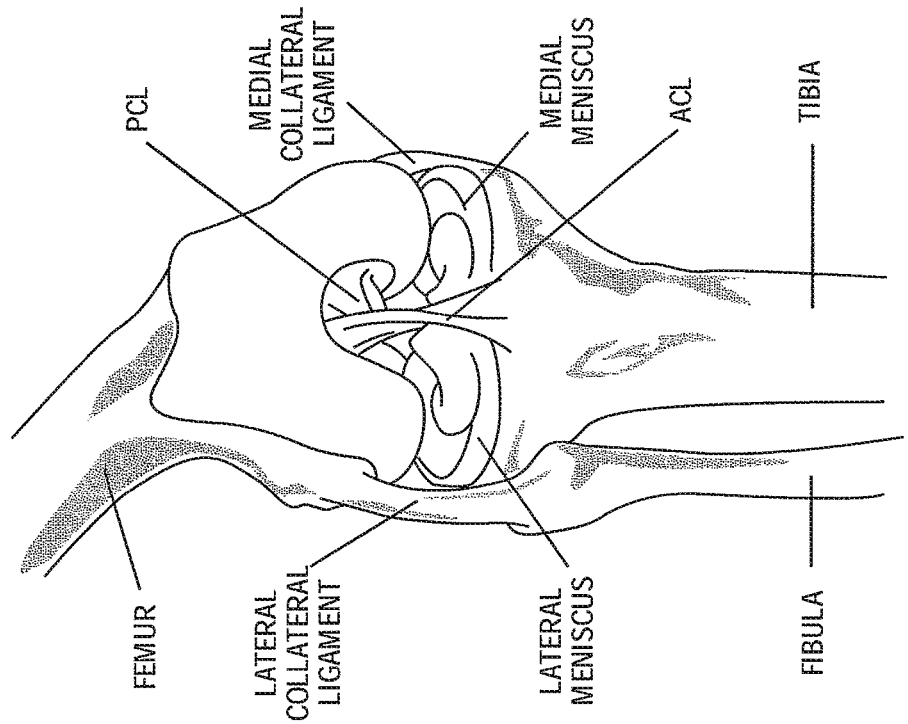
FIG. 1B
FIG. 1A

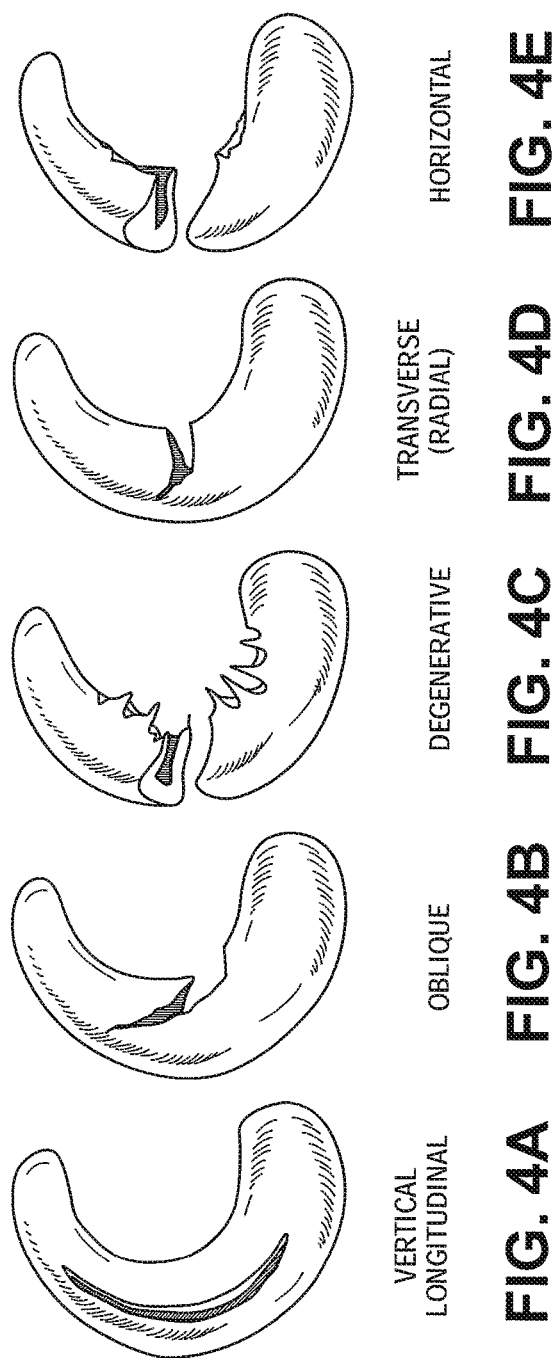

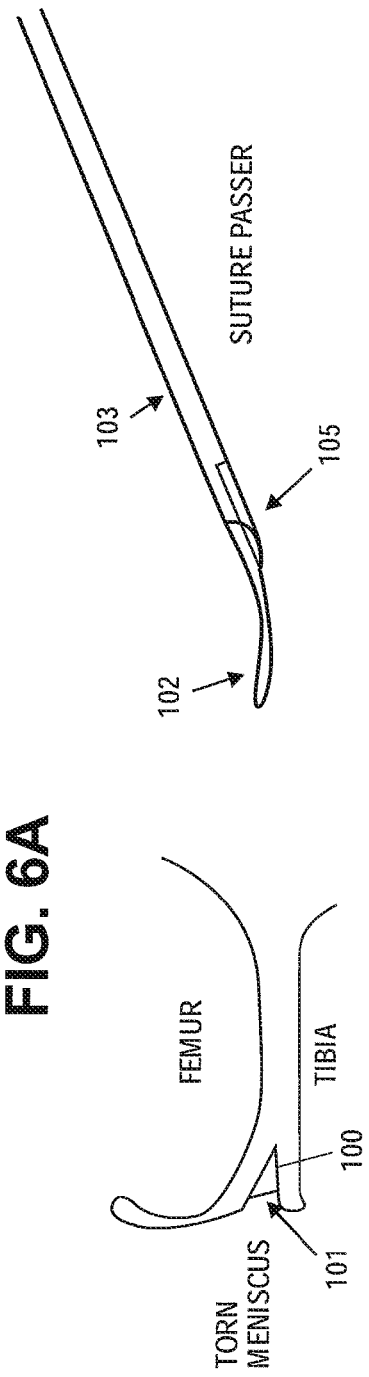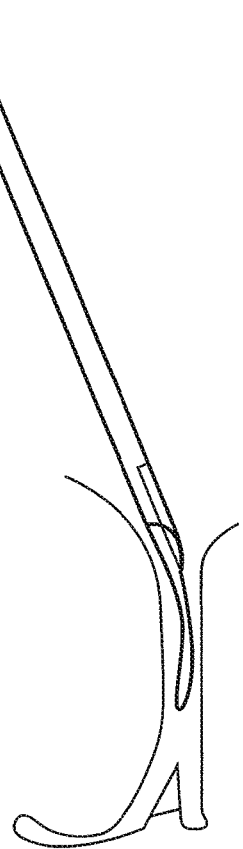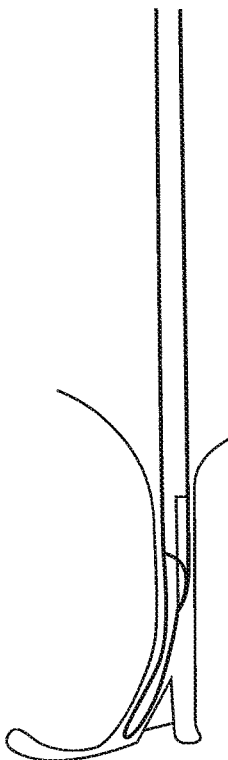

SHEET METAL RETURNS

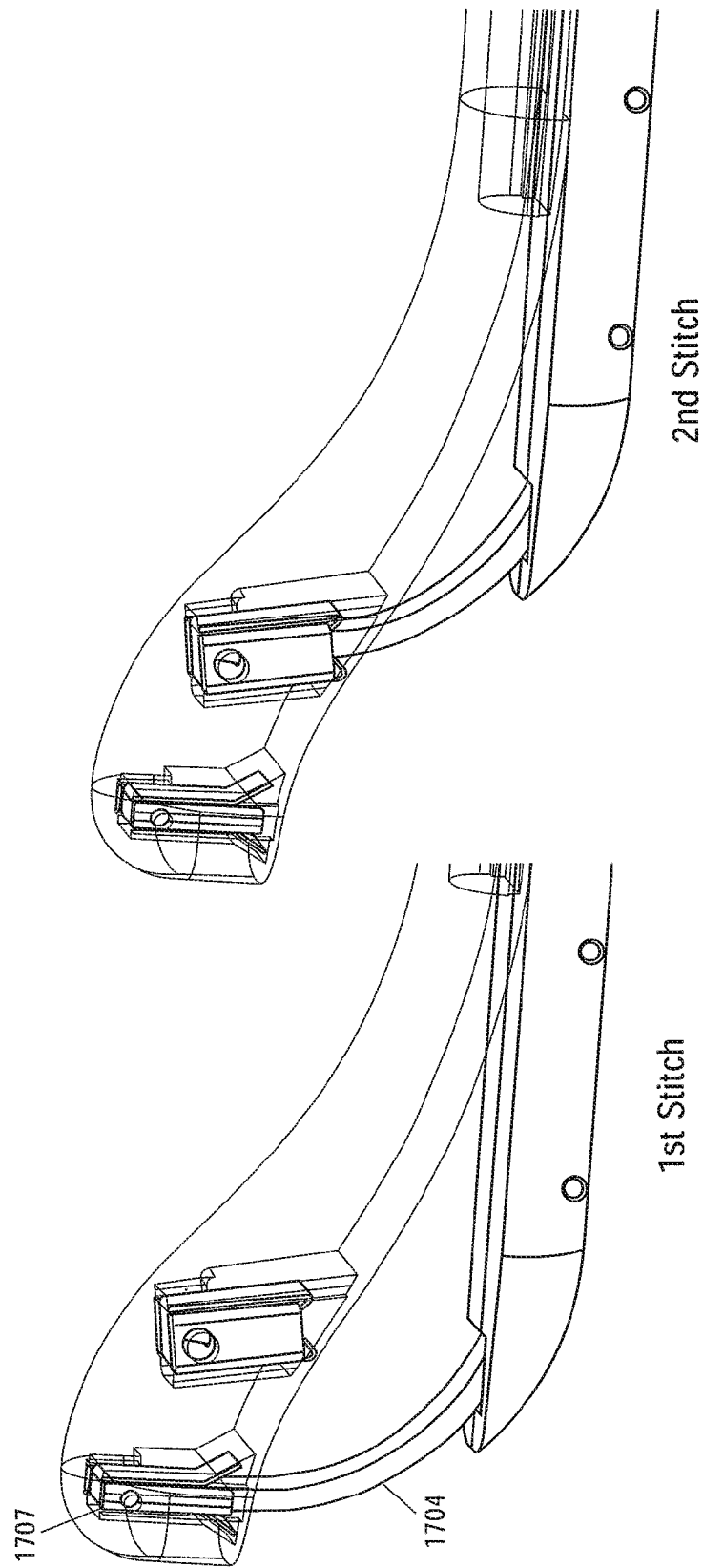

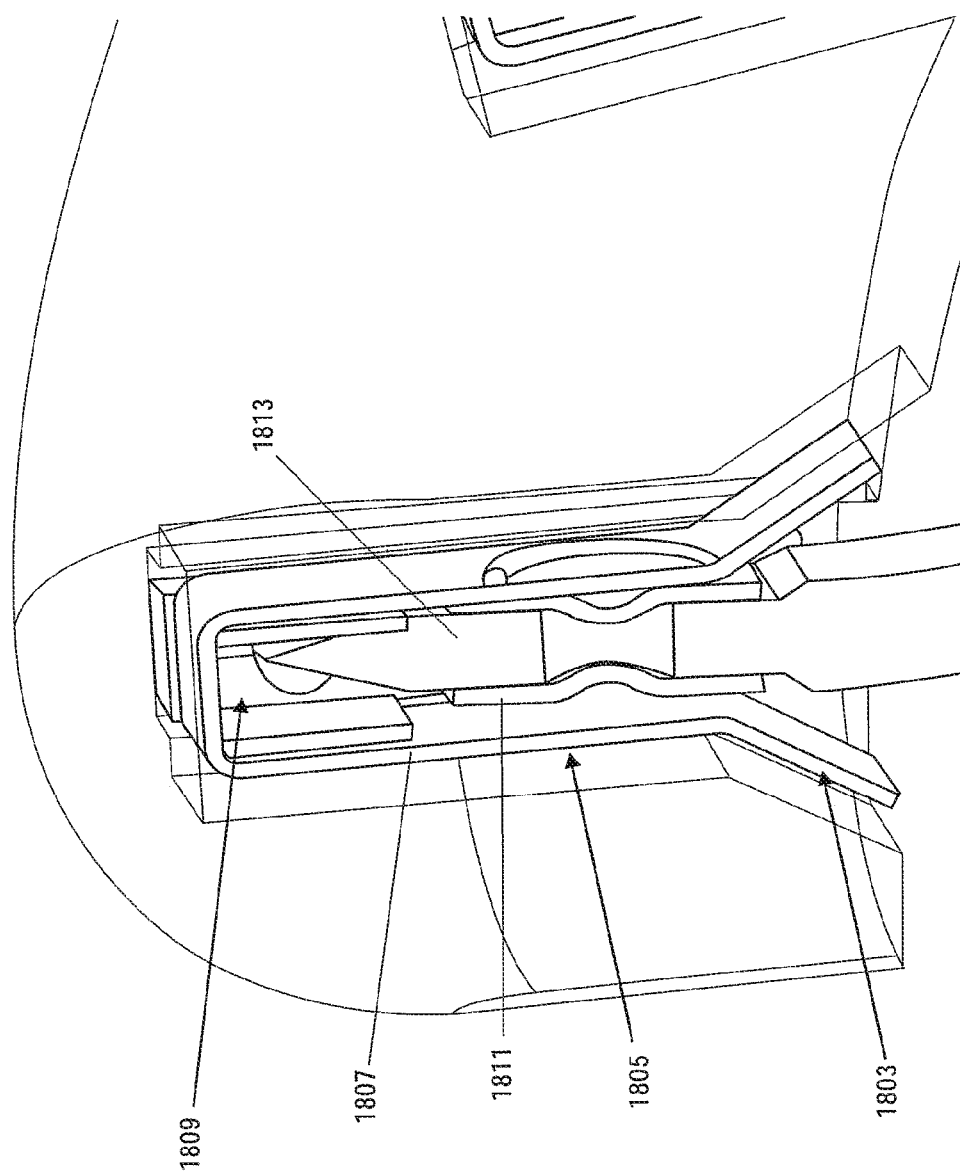

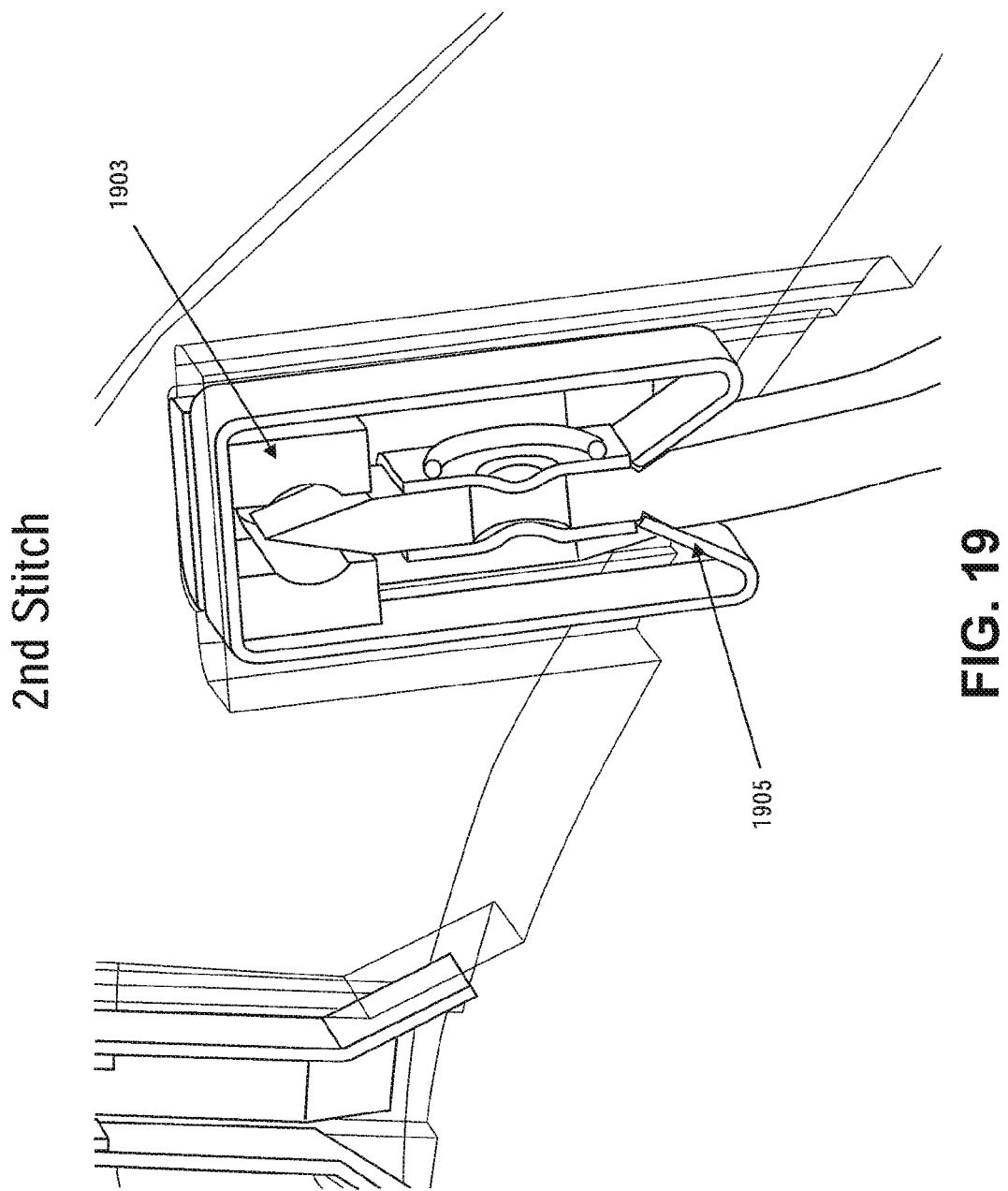

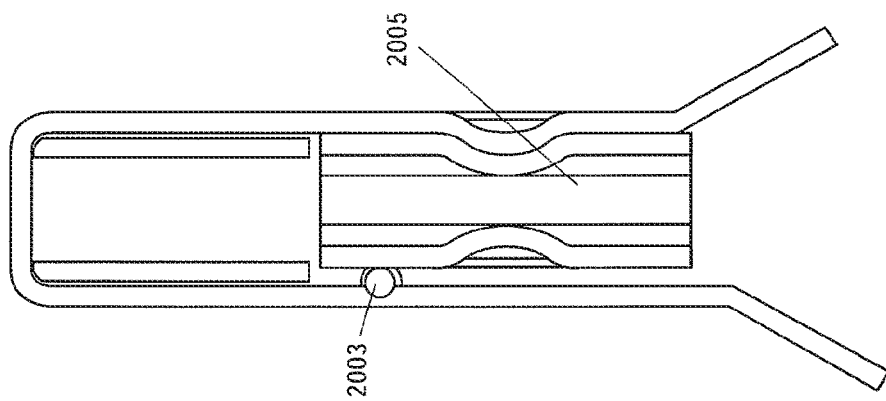
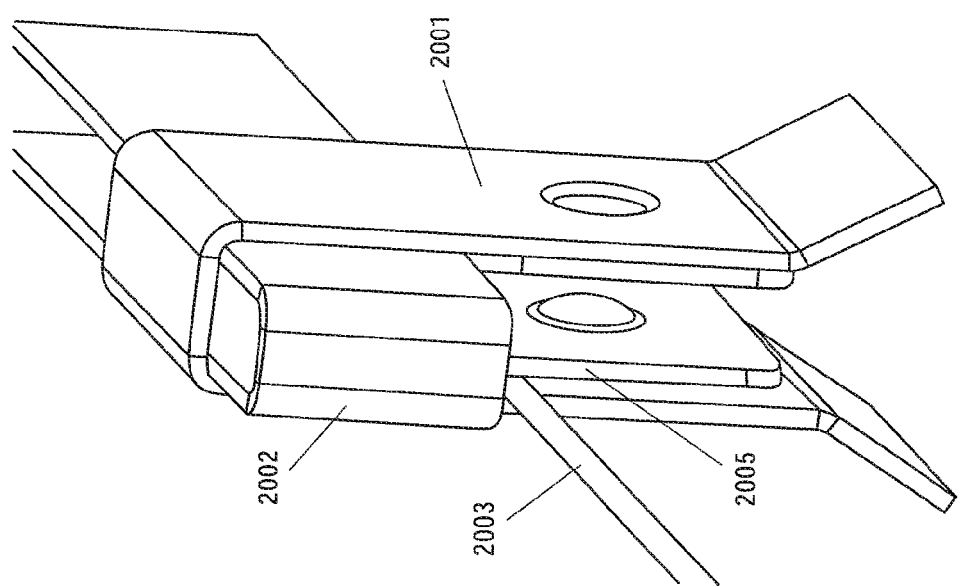

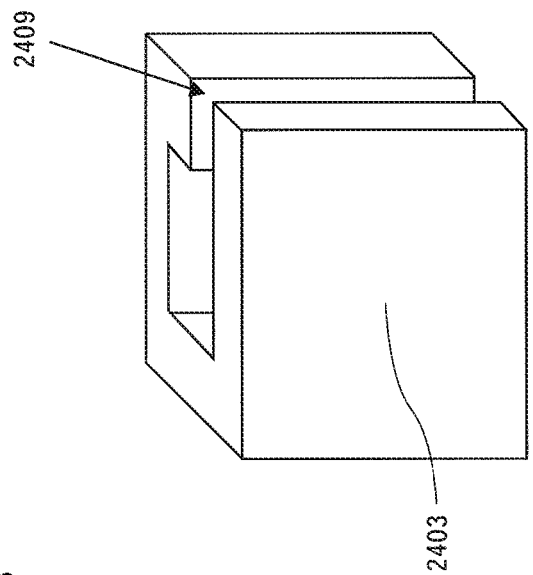
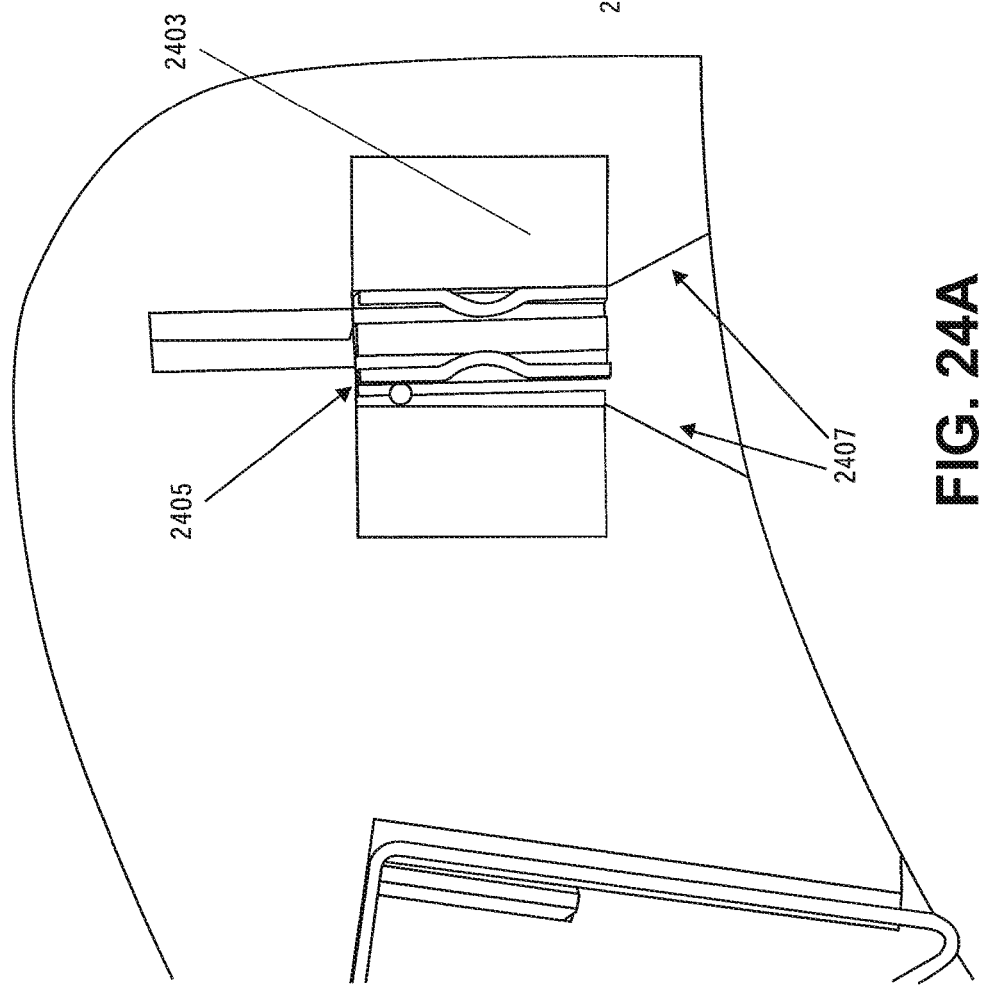
FIG. 24B
FIG. 24A

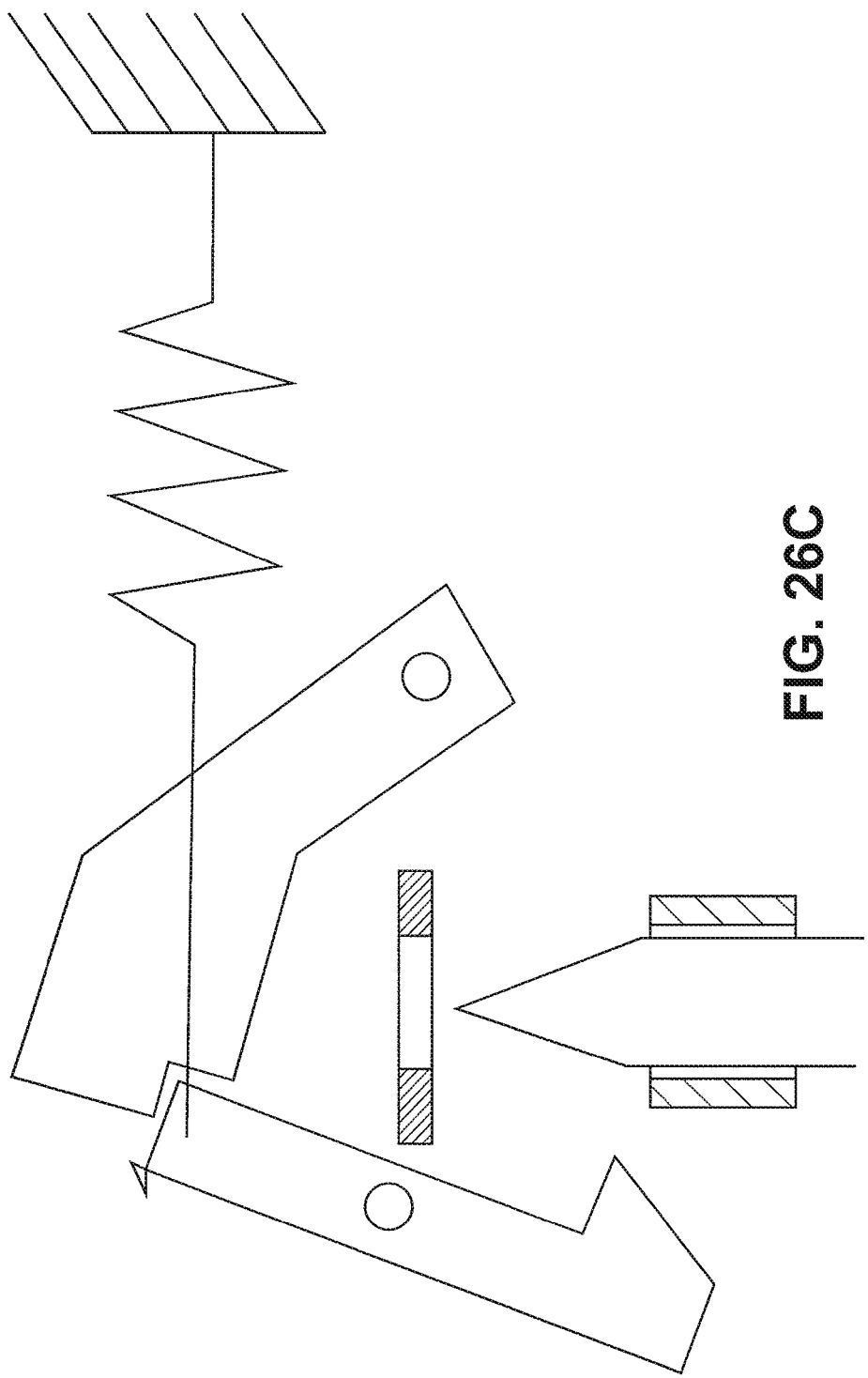

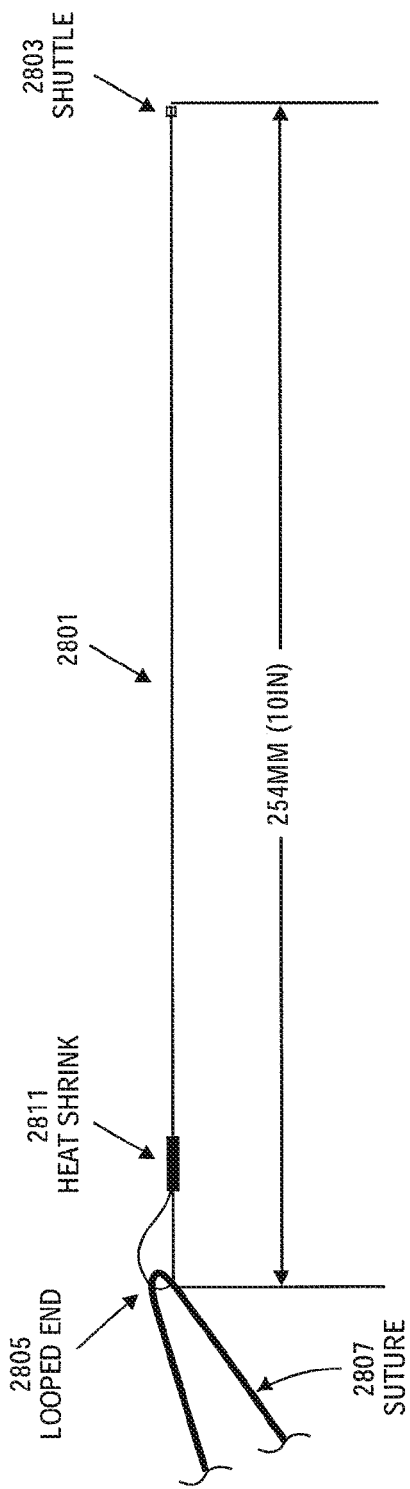
FIG. 28
FIG. 29A
FIG. 29B

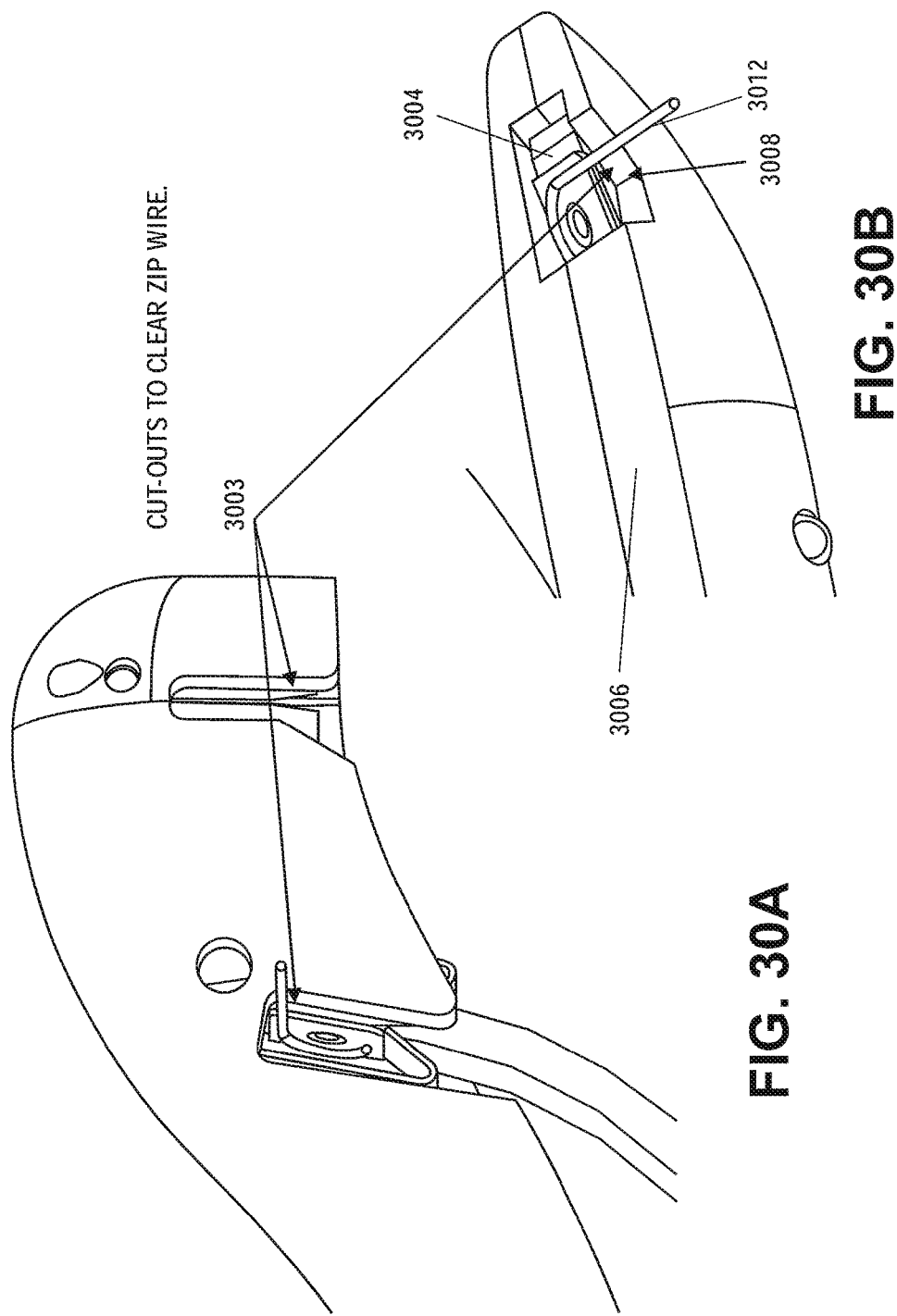

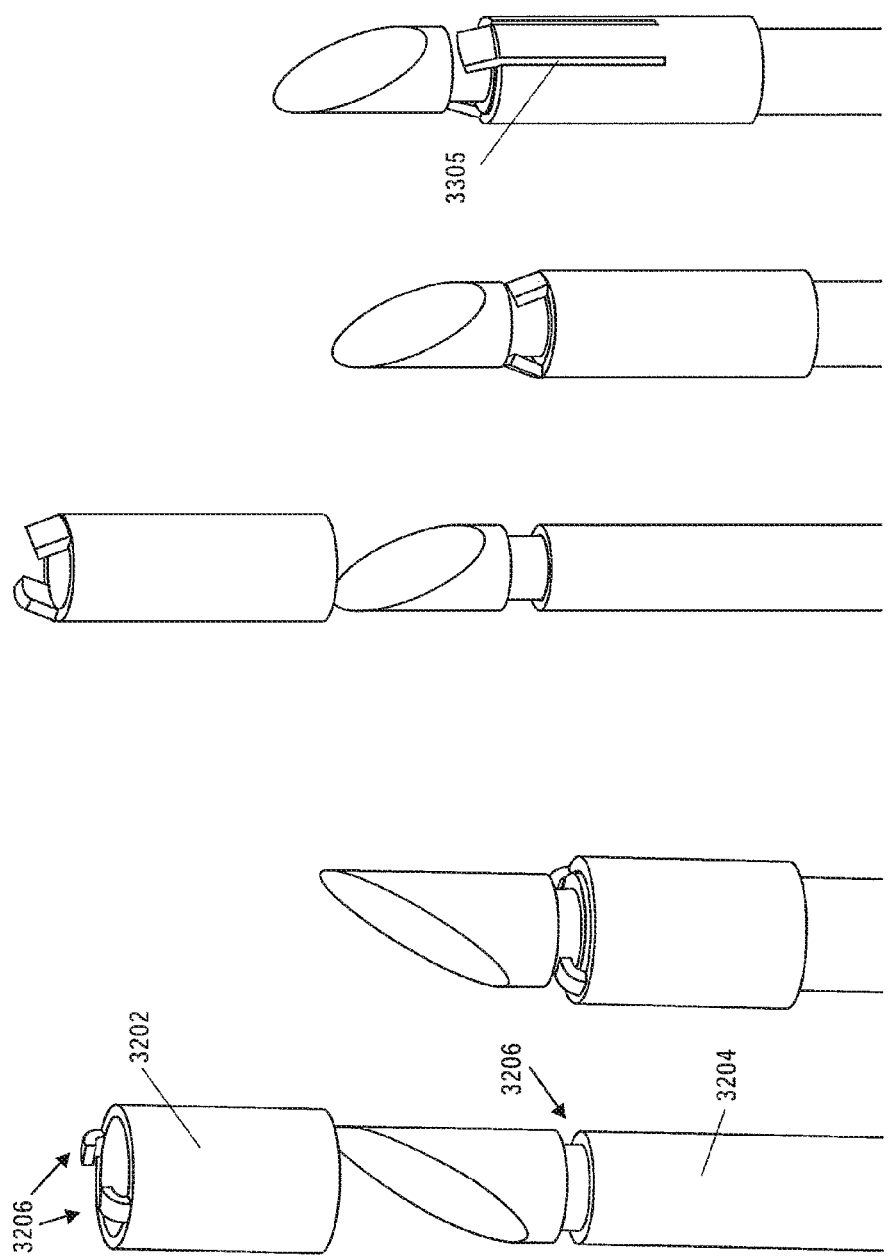

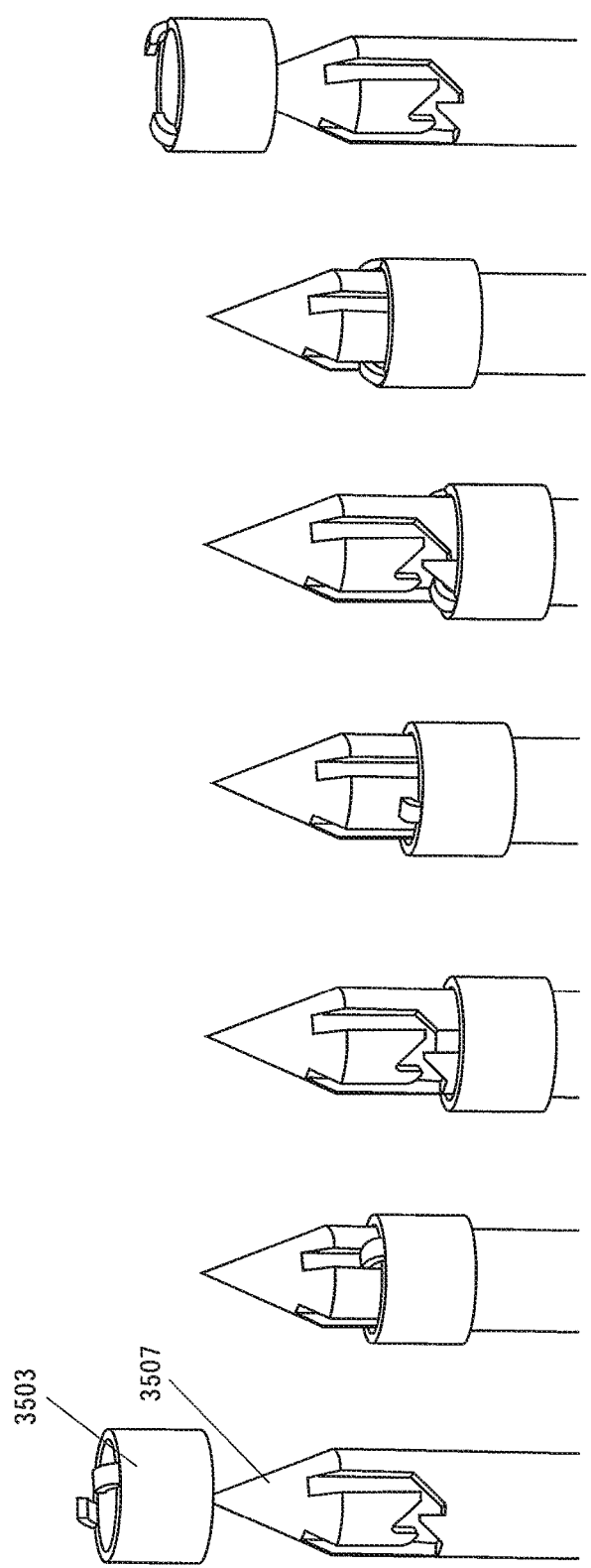

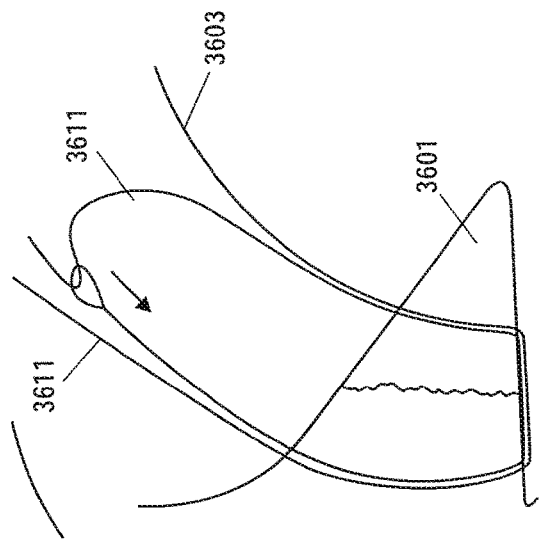
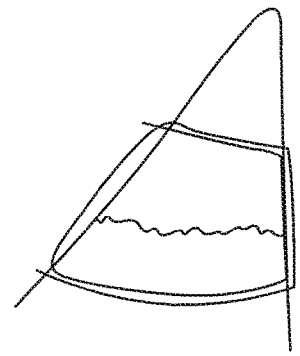
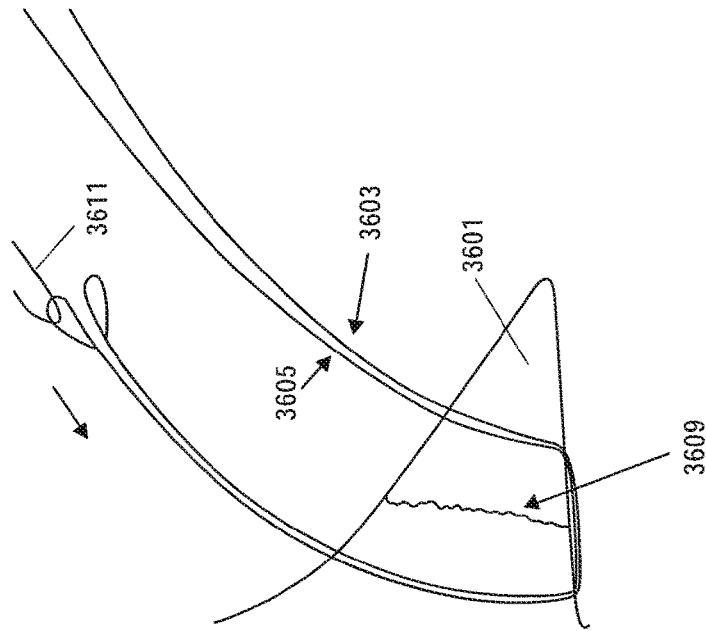
FIG. 36B
FIG. 36C
FIG. 36A

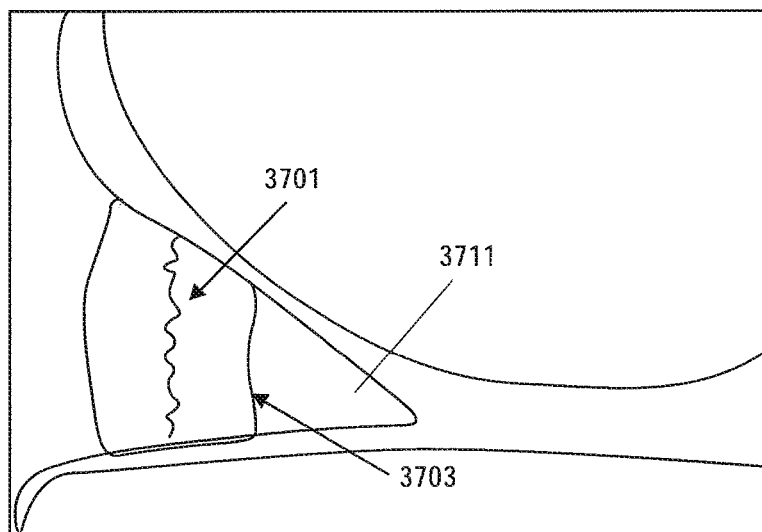
FIG. 37A
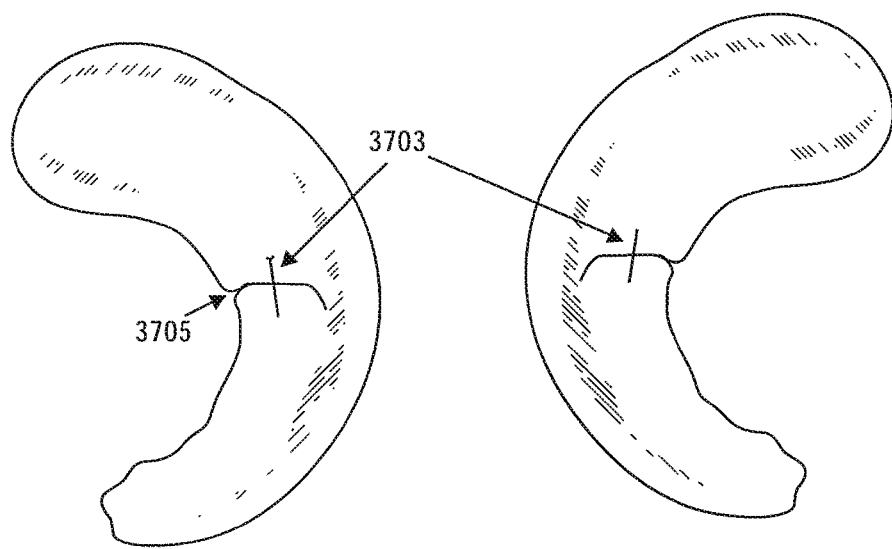
FIG. 37B  FIG. 37C

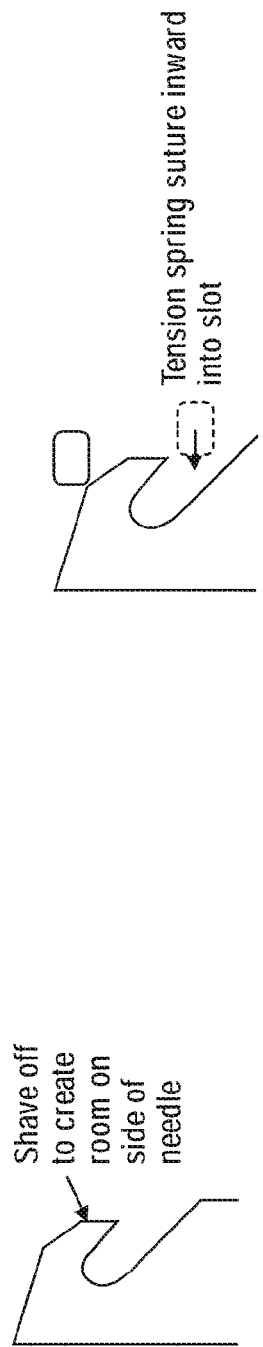

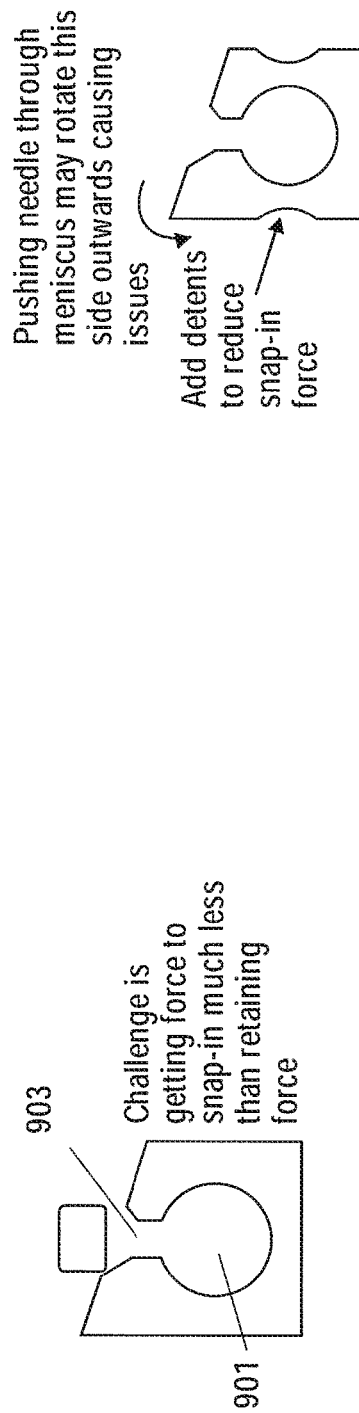
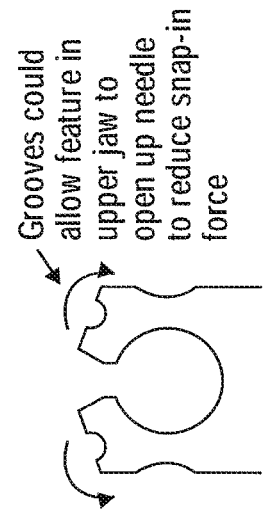
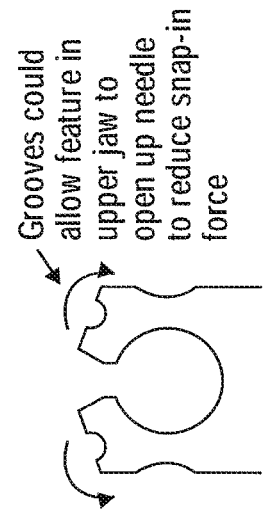
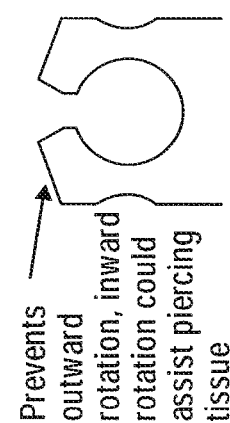
FIG. 43A
FIG. 43B
FIG. 43C
FIG. 43D Prevents outward rotation Mandrel is advanced, pops under suture, restraining suture; needle is then retracted

    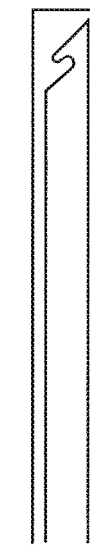 
FIG. 46A   FIG. 46B   FIG. 46C   FIG. 46D   FIG. 46E   FIG. 46F
    
FIG. 46G   FIG. 46H   FIG. 46I   FIG. 46J   FIG. 46K

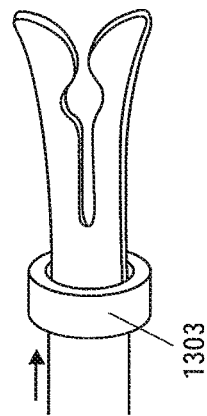
FIG. 47B
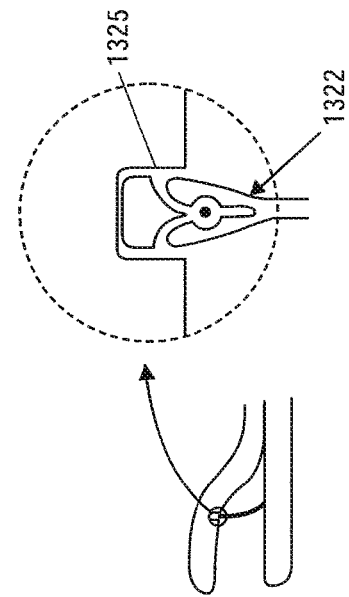
FIG. 47D1   FIG. 47D2
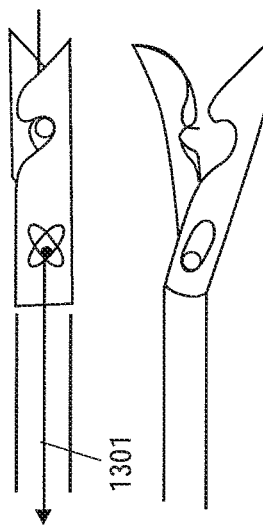
FIG. 47A1   FIG. 47A2
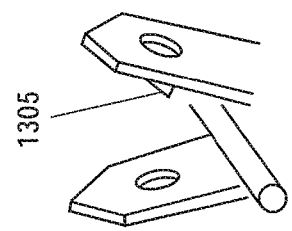
FIG. 47C

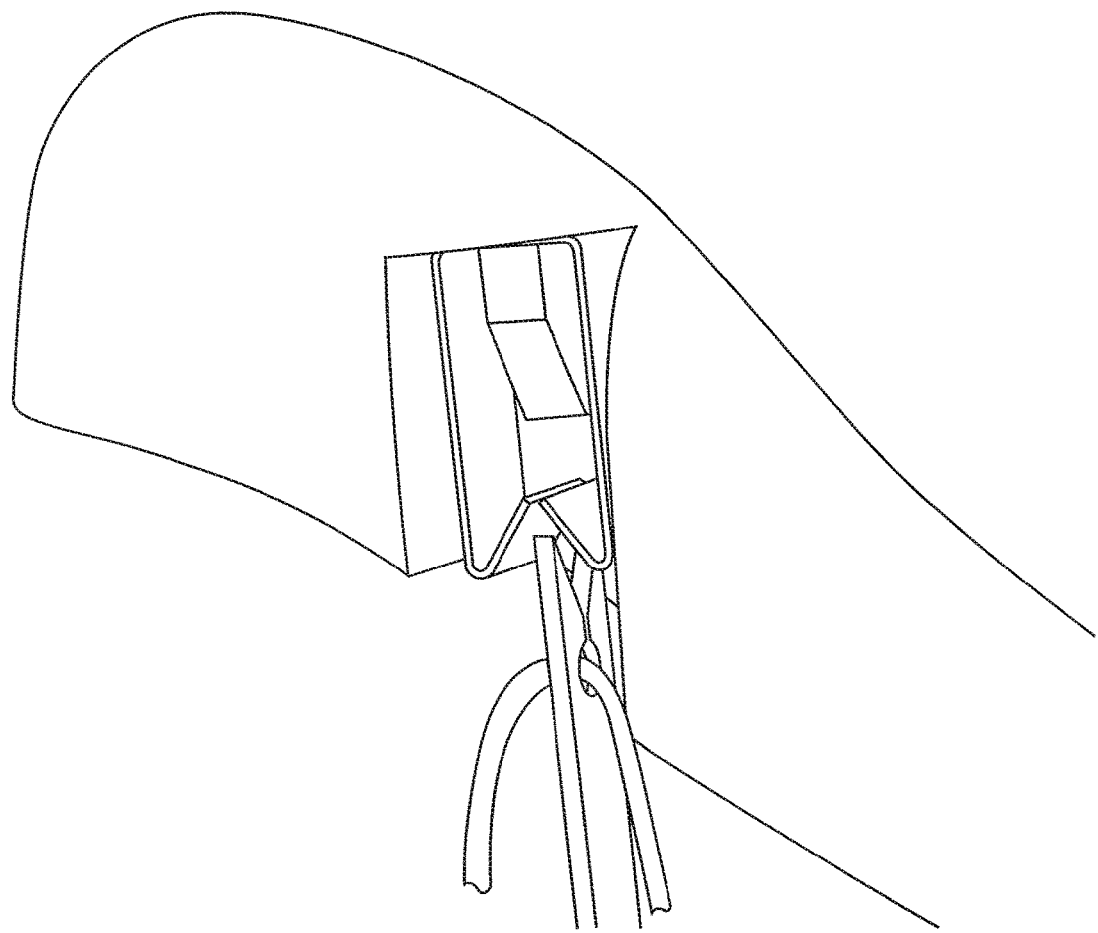
FIG. 47D3

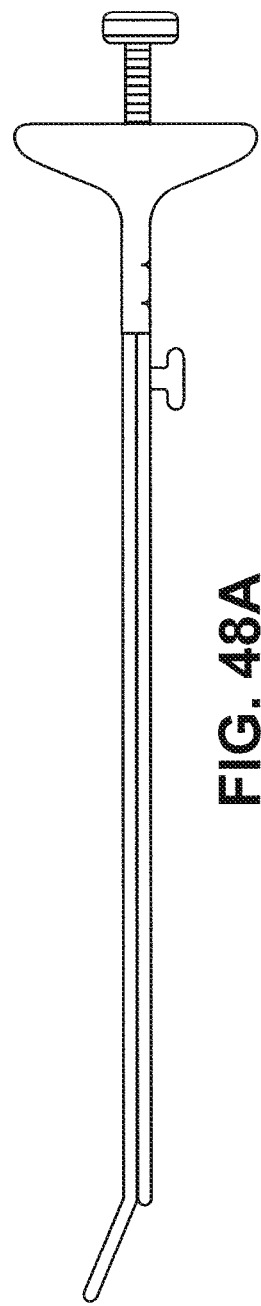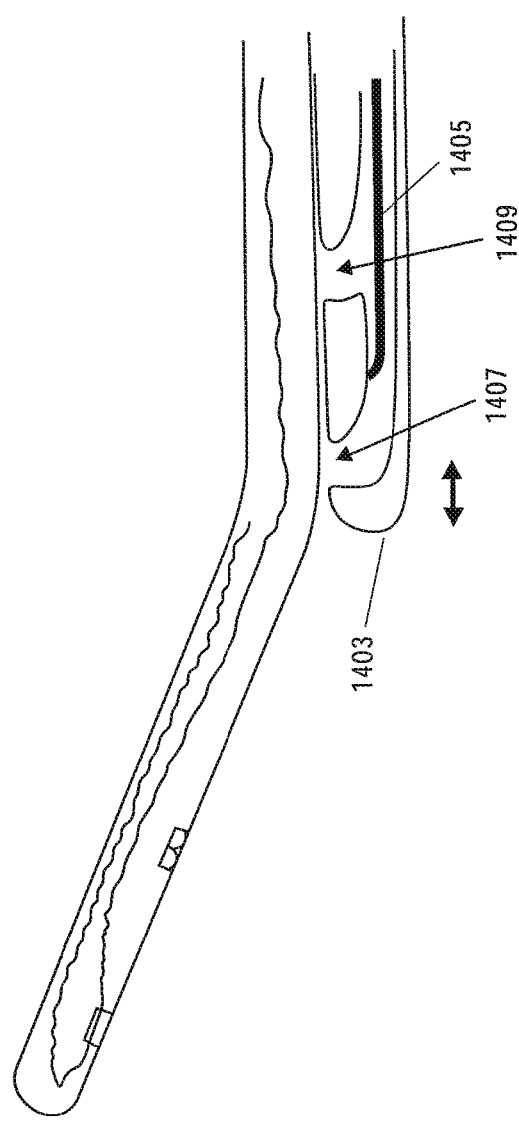
FIG. 48A
FIG. 48B

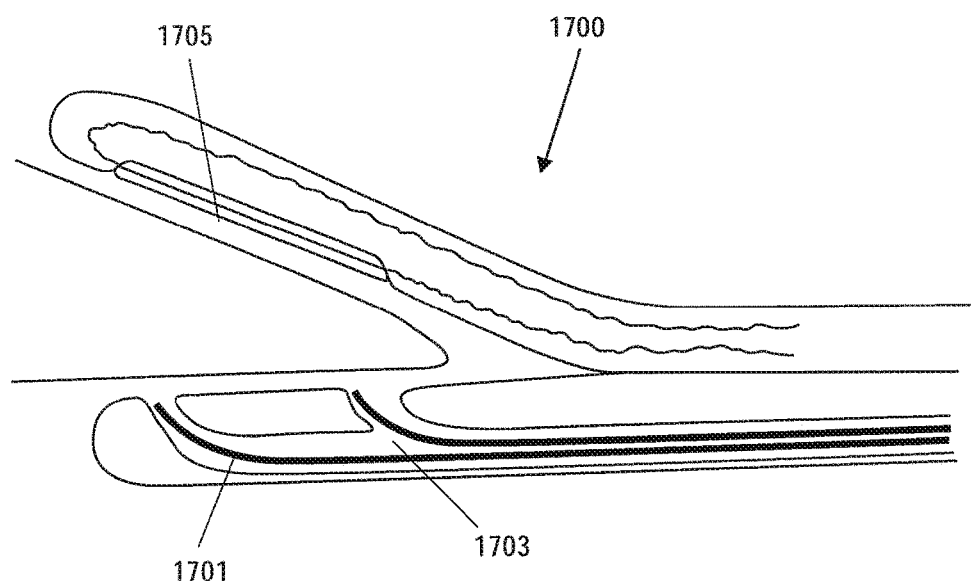
FIG. 51
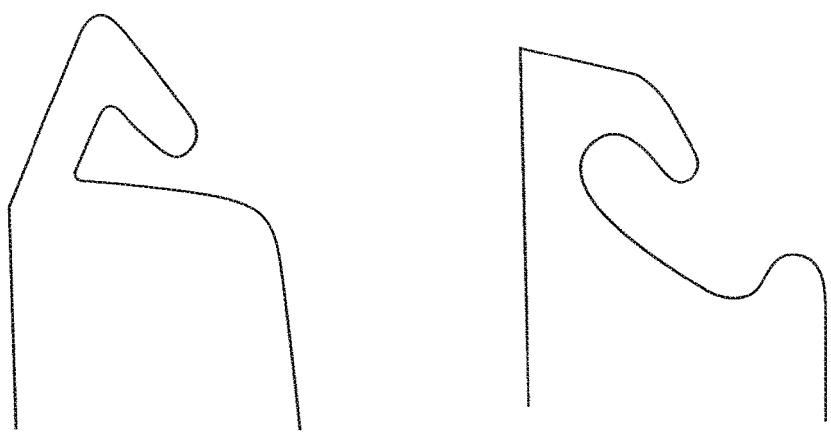
FIG. 52A   FIG. 52B

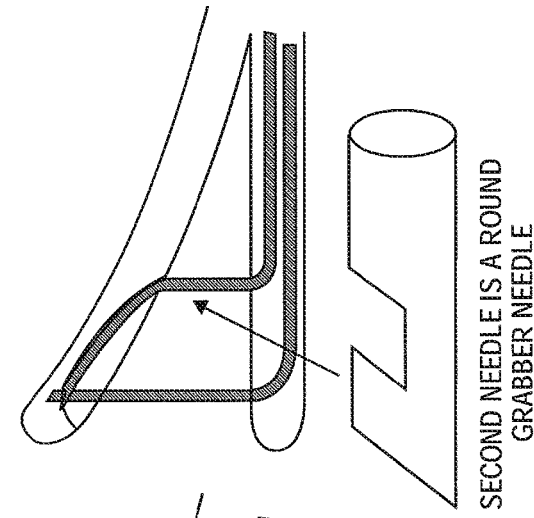

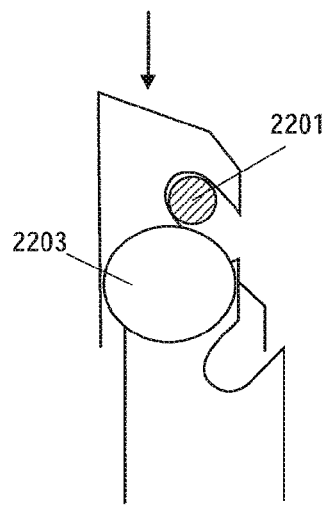
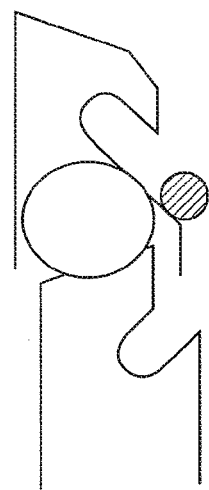
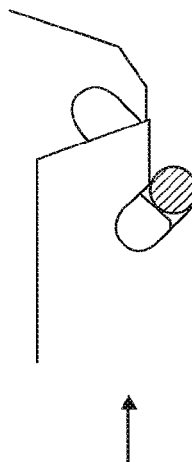
FIG. 56A   FIG. 56B   FIG. 56C
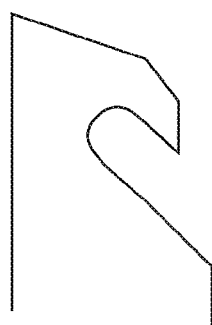
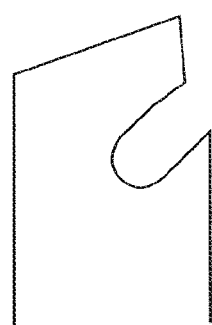
FIG. 56D   FIG. 56E

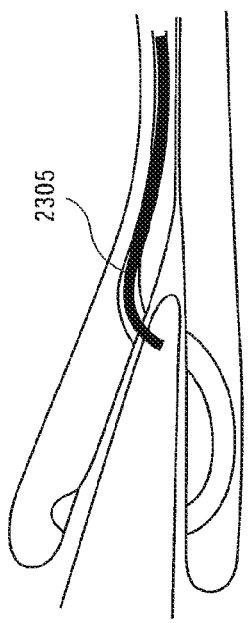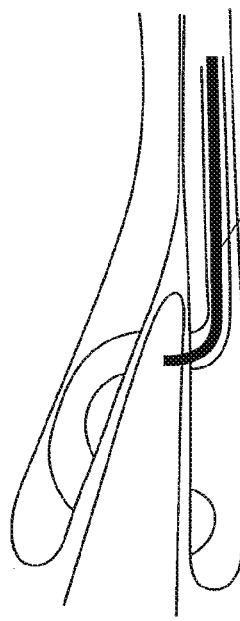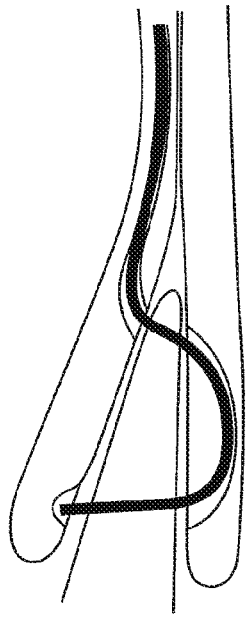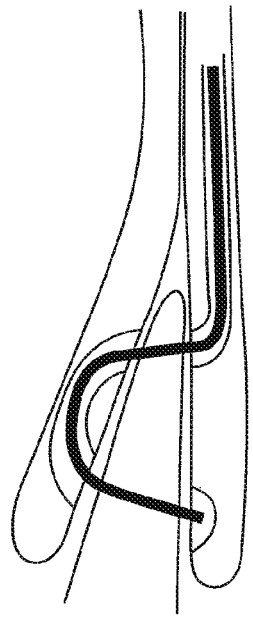

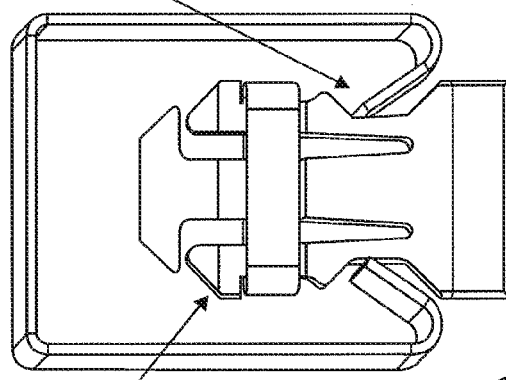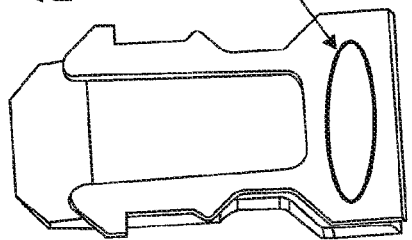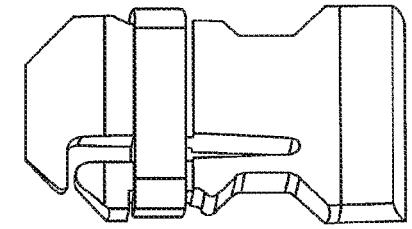

US 10,758,222 B2

MENISCUS REPAIR

CROSS REFERENCE TO RELATED APPLICATIONS

This patent application is a continuation of U.S. patent application Ser. No. 13/247,892, titled "MENISCUS REPAIR," filed Sep. 28, 2011, now U.S. Pat. No. 9,861,354, which claims priority to the following provisional patent applications: U.S. Provisional Patent Application No. 61/483,200, titled "MENISCUS REPAIR" and filed May 6, 2011, and U.S. Provisional Patent Application No. 61/511,922, titled "MENISCUS REPAIR" and filed Jul. 26, 2011.

This patent application may be related to U.S. patent application Ser. No. 12/942,803, filed on Nov. 9, 2010, titled "DEVICES, SYSTEMS AND METHODS FOR MENISCUS REPAIR" which claim priority to U.S. Provisional Patent Application Nos.: 61/259,572, filed Nov. 9, 2009, titled "DEVICES, SYSTEMS AND METHODS FOR MENISCUS REPAIR"; 61/295,354, filed Jan. 15, 2010, titled "DEVICES, SYSTEMS AND METHODS FOR MENISCUS REPAIR;" and 61/318,215, filed Mar. 26, 2010, titled "CONTINUOUS SUTURE PASSERS HAVING TISSUE PENETRATING SUTURE SHUTTLES."

All of these applications are herein incorporated by reference in their entirety

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods, devices and systems described herein may be used for the repair of a meniscus. In particular, the methods, devices and systems described herein may be useful for the surgical repair of a torn meniscus.

BACKGROUND

The meniscus is a C-shaped piece of fibrocartilage which is located at the peripheral aspect of the joint (e.g., the knee) between the condyles of the femur and the tibia on the lateral and medial sides of the knee. The central $\frac{2}{3}^{rds}$ of the meniscus has a limited blood supply while the peripheral $\frac{1}{3}^{rd}$ typically has an excellent blood supply. Acute traumatic events commonly cause meniscus tears in younger patients while degenerative tears are common in older patients as the menisci become increasingly brittle with age. Typically, when the meniscus is damaged, a torn piece may move in an abnormal fashion inside the joint, which may lead to pain and loss of function of the joint. Early arthritis can also occur due to these tears as abnormal mechanical movement of torn meniscal tissue and the loss of the shock absorbing properties of the meniscus lead to destruction of the surrounding articular cartilage. Occasionally, it is possible to repair a torn meniscus. While this may be done arthroscopically, surgical repair using a suture has proven difficult because of the hard-to-reach nature of the region and the difficulty in placing sutures in a way that compresses and secures the torn surfaces.

Arthroscopy typically involves inserting a fiberoptic telescope that is about the size of a pencil into the joint through an incision that is approximately ⅛ inch long. Fluid may then be inserted into the joint to distend the joint and to allow for the visualization of the structures within that joint. Then, using miniature instruments which may be as small as ⅒ of an inch, the structures are examined and the surgery is performed.

FIGS. 1A-2 illustrate the anatomy of the meniscus in the context of a knee joint. As shown in FIG. 2 the capsule region (the outer edge region of the meniscus) is vascularized. Blood enters the meniscus from the menisculocapsular region 211 lateral to the meniscus. A typical meniscus has a flattened ("bottom") and a concave top, and the outer cross-sectional shape is somewhat triangular. The outer edge of the meniscus transitions into the capsule. FIG. 3 illustrates the various fibers forming a meniscus. As illustrated in FIG. 3, there are circumferential fibers extending along the curved length of the meniscus, as well as radial fibers, and more randomly distributed mesh network fibers. Because of the relative orientations and structures of these fibers, and the predominance of circumferential fibers, it may be beneficial to repair the meniscus by suturing radially (vertically) rather than longitudinally or horizontally, depending on the type of repair being performed.

For example, FIGS. 4A-4E illustrate various tear patterns or injuries to a meniscus. Tears may be vertical/longitudinal (FIG. 4A), Oblique (FIG. 4B), Degenerative (FIG. 4C), including radially degenerative, Transverse or radial (FIG. 4D) and Horizontal (FIG. 4E). Most prior art devices for suturing or repairing the meniscus are only capable of reliably repairing vertical/longitudinal tears. Such devices are not typically recommended for repair of radial tears, particularly not arthroscopically/minimally invasively. FIGS. 5A-5C illustrate sutures placed with prior art devices to repair (via suturing) a torn meniscus (showing a longitudinal tear). FIG. 5A illustrates the results of a repair by a Smith&Nephew "Fast-Fix" device (comparable to a repair by a Biomet MaxFire device). FIG. 5B illustrates a Cayenne "CrossFix" device, and FIG. 5C illustrates a repair using an Arthrex meniscal "Viper" device.

In FIGS. 5A-5C the devices affecting these repairs require projection through the meniscus and substantially into the capsule region outside of the meniscus, which could potentially damage the nearby major nerves and large blood vessels. Further, the prior art devices, such as those placing the sutures illustrated in FIG. 5A-5C, typically place horizontal mattress suture patterns rather than vertical mattress suture patterns because vertical patterns are considerably more difficult (if not impossible) for surgeons to place when using these devices. Vertical mattress patterns would have improved pull through strength because of the aforementioned predominance of circumferential collagen fibers found within the meniscus structure. See, e.g., Boenisch, U. W., et al, "Pull-out strength and stiffness of meniscal repair using absorbable arrows or Ti-Cron vertical and horizontal loop sutures," Am J Sports Med. 1999 September-October; 27(5):626-31. Additionally, the devices forming the suture patterns illustrated in FIG. 5A-5C are only capable of point fixation; that is they cannot compress the tears uniformly across the torn surface. Finally, such prior art devices are designed for repairing peripheral vertical meniscus tears (torn from the superior surface to the inferior surface in line with the C-shape of the meniscus) and are incapable of repairing commonly encountered radial meniscus tears.

Thus, there is a need for methods, devices and systems for repairing a torn meniscus that allow repair of the meniscus in a manner that decreases patient discomfort and enhances the rate of recovery. In particular, it would be beneficial to provide methods, devices and systems capable of repairing both radial and longitudinal tears without risking additional damage to the meniscus or the vascular systems feeding the meniscus. In addition, it would be highly beneficial to provide methods and devices allowing a physician to minimally invasively suture the meniscus in a vertical loop. The methods, devices and systems described herein may address this need.

SUMMARY OF THE DISCLOSURE

The present invention relates to devices, systems and methods for repairing a meniscus, and particularly a torn meniscus. In general, described herein are meniscus repair devices, including suture passers, as well as methods of repairing a meniscus, including methods of suturing a meniscus.

For example, described herein are methods of arthroscopically placing a suture around a meniscus tear without penetrating the perimeniscular capsule. The suture may be placed entirely arthroscopically. Thus, two or fewer incisions may be made into the knee, and a camera and suture passer may be placed within the knee. In any of these methods, the suture may be placed by extending a tissue penetrating element from the suture passer in an arcuate pathway through the meniscus. Further, in any of these methods, the suture passer may approach the meniscus from the anterior of the knee, and may approach the meniscus tear from the apex of the meniscus.

For example, the methods described herein may include methods of minimally invasively repairing a torn meniscus by joining both sides of a tear in the meniscus and securing the joined entire length of the tear, from the superior surface of the meniscus to the inferior surface of the meniscus, in at least one plane. The plane may be in any appropriate section through the meniscus, spanning the tear. The plane may be formed by a loop of suture. The device does not significantly penetrate into the structures in the back of the knee (peripheral to the capsule) therefore there is little risk of iatrogenic injury to major knee nerves or vessels during repair. In some variations, the suture passers described herein may be used to repair the meniscus without substantially penetrating (or puncturing through) the capsule of the meniscus; the capsular region is highly vascularized, and it is therefore desirable to minimize damage to this region. In general, these methods may be performed minimally invasively, by minimally invasively accessing the apex of the meniscus with a meniscus repair device (e.g., suture passer, probe, etc.). For example, an anterior approach may be used to place the repair device within the interior of the knee; from the interior of the knee the entire procedure may be performed without having to leave the interior of the knee. Thus, joining both sides of the tear in the meniscus may include joining both sides without penetrating toward neurovascular structures beyond the posterior capsule of the knee. As described herein, joining the torn surfaces of the meniscus may mean passing a suture loop completely around the tear in the meniscus from the superior surface to the inferior surface of the meniscus.

For example, described herein are methods of repairing a meniscus that include using a suture passer to pass a suturing element from the region between the superior surface of the meniscus and the femoral condyle, through the meniscus tissue, into the region between the inferior surface of the meniscus and the tibial plateau, across the inferior surface of the meniscus, and back to the superior surface of the meniscus, without deeply penetrating the posterior capsular region of the knee. Equivalently, the suture element may be passed from the inferior surface of the meniscus to the superior surface and back to the inferior surface.

For example, described herein are methods of repairing a meniscus by suturing a loop around the meniscus (e.g. around a tear in a meniscus) from the femoral-facing upper outer surface (i.e., the superior surface) of the meniscus to the tibial-facing lower outer surface (i.e., the inferior surface) of the meniscus. These methods may include the steps of: minimally invasively positioning a suture passer adjacent to the meniscus; using the suture passer to pass a suturing element around the meniscus extending from the upper outer surface of the meniscus, through the meniscus to the lower outer surface of the meniscus, across the lower outer surface of the meniscus, and back to the upper outer surface of the meniscus.

The suture passer may be minimally invasively inserted in any appropriate manner, including arthroscopically inserting the suture passer into the knee (e.g., near the meniscus). For example, minimally invasively inserting the suture passer may include inserting a suture passer having a curved or bent first arm and a straight second arm. In particular, the suture passer may be inserted with the first arm extended distally and the second arm located proximal to the first arm. In general, the first arm may be movable proximally and distally relative to the second arm.

Any appropriate suturing element may be used, including each of (alone or in combination): a suture, a suture shuttle, and/or a lead wire. In some variations, the suturing element is a staple. When a lead wire is used, the method may also include the step of pulling on the lead wire to draw a suture through and/or around the meniscus.

In some variations, the step of using the suture passer may include positioning a first arm of the suture passer adjacent to the upper surface of the meniscus and positioning a second arm of the suture passer adjacent to the lower surface of the meniscus.

Also described herein are methods of repairing a meniscus by suturing a loop around the meniscus from the femoral-facing upper outer surface of the meniscus to the tibial-facing lower outer surface of the meniscus, including the steps of: minimally invasively positioning a suture passer adjacent to the meniscus; using the suture passer to pass a suturing element around the meniscus extending from the lower outer surface of the meniscus, through the meniscus to the upper outer surface of the meniscus, across the upper outer surface of the meniscus, and back to the lower outer surface of the meniscus.

For example, described herein are methods of minimally invasively repairing a meniscus using a suture passer including the steps of: extending a first arm of the suture passer into a space between the superior surface of the meniscus and the femur; extending a second arm of the suture passer into a space between the inferior surface of the meniscus and the tibia; and passing a suturing element between the first arm and second arm of the suture passer. The steps of extending the first arm and the second arms may be performed in any sequence, or may be performed simultaneously (e.g., extending the first arm of the suture passer comprises extending the first arm before extending the second arm). The method may also include accessing the apex of a meniscus in the knee joint from an anterior approach. In some variations, it may be helpful to push the superior surface of the meniscus with the first arm to enlarge the space between the inferior surface of the meniscus and the tibia before extending the second arm. In general, the method may include extending a tissue penetrator between the first arm and the second arm to capture a suturing element and retracting the tissue penetrator to draw the captured suturing element through the meniscus.

Also described herein are methods of repairing a meniscus by suturing a vertical loop through and/or around the meniscus from the femoral-facing upper outer surface of the meniscus to the tibial-facing lower outer surface of the meniscus, including the steps of: minimally invasively inserting a suture passer adjacent to the meniscus; using the suture passer to pass a suturing element around the meniscus in a vertical loop extending from the upper outer surface of the meniscus, through the meniscus to the lower outer surface of the meniscus, radially across the lower outer surface of the meniscus and back to the upper outer surface of the meniscus.

Also described are methods of repairing a meniscus by suturing a longitudinal loop around the meniscus from the femoral-facing upper outer surface of the meniscus to the tibial-facing lower outer surface of the meniscus, including the steps of: minimally invasively inserting a suture passer adjacent to the meniscus; using the suture passer to pass a suturing element around the meniscus in a lateral loop extending from the upper outer surface, through the meniscus to the lower outer surface of the meniscus, laterally along the lower outer surface of the meniscus and back to the upper outer surface of the meniscus.

Meniscus repair devices (including but not limited to suture passers) are also described. For example, a meniscus repair device configured to aid in repair of a meniscus of a knee may include: an elongate body extending distally and proximally; a first arm extending distally in parallel or in line with the elongate body; and a second arm extendable distally at an acute angle from the elongate body, wherein either or both the first and second arms are slideably coupled to move distally and proximally relative to each other such that the device has a first configuration in which the first and second arms form an acute-angled distal-facing opening, and a second configuration wherein the first arm is proximal to the second arm.

In some variations the device includes a handle at the proximal end, and/or a tissue penetrator configured to extend between the first and second arms when the device is in the first configuration. The device may also include at least one dock in the second arm configured to receive a tissue penetrator extending from the first arm when the device is in the first configuration. The tissue penetrator may be configured to extend from the first arm.

Thus, also described herein are meniscus repair devices configured to aid in repair of a meniscus of a knee, the devices comprising: an elongate body extending distally and proximally; a first arm extending distally in parallel or in line with the elongate body; a second arm extendable distally at an acute angle from the elongate body, wherein either or both the first and second arms are slideably coupled to move distally and proximally relative to each other such that the device has a first configuration in which the first and second arms form an acute-angled distal-facing opening, and a second configuration wherein the first arm is proximal to the second arm; and a tissue penetrator configured to extend between the first arm and second arm and pass a suturing element between the first and second arms. As mentioned, a suturing element may include: a suture shuttle; a lead wire, a suture, staple, or some combination of these elements.

Also described herein are methods of passing a suture using a suture passer device and lead wire, including the steps of: positioning a first arm and a second arm of the suture passer device around a target tissue to be sutured; forming a first stitch through the target tissue with a lead wire by passing a tissue penetrator between the first and second arms and through the target tissue to draw the distal end of the lead wire through the target tissue from the first arm to the second arm; forming a second stitch through the target tissue with the lead wire by passing the tissue penetrator between the first and second arms and through the target tissue to draw the distal end of the lead wire through the target tissue from the second arm to the first arm; pulling a suture coupled to the proximal end of the lead wire through the target tissue by pulling from the distal end of the lead wire; and removing the lead wire from the tissue while leaving the suture in the tissue. The step of positioning the first and second arms around the target tissue may include positioning the first and second arms around a meniscus of a knee. Forming the first stitch may include extending the tissue penetrator through the target tissue from the first arm to the second arm, to engage a suturing element releasably held by the second arm, the suturing element comprising the lead wire, and pulling the suturing element back through the target tissue to the first arm.

Also described herein are suture passers configured to pass a suture from a first side of a target tissue to a second side of a target tissue and back to the first side. For example, a suture passer may include: an elongate body extending distally from a proximal handle; a first arm extending distally from the elongate body; a second arm extending distally from the elongate body and configured to move relative to the first arm to form a distal-facing opening to hold a target tissue; a tissue penetrator configured to extend through tissue within the opening and to carry a suturing element between the first arm and the second arm; a release dock on the second arm configured to hold the suturing element until the suturing element is engaged by the tissue penetrator; and a holding dock on the second arm configured to receive the suturing element from the tissue penetrator.

The tissue penetrator may extend and retract into the first arm, and in some variations may be formed of a shape memory material configured to extend between the first and second arms in a curved path. In general, the tissue penetrator is configured to carry a suturing element (e.g., a shuttle and/or pull wire and/or a suture).

The second arm may extend distally from the elongate body to form an acute angle with the elongate body, and in some variations may be configured to move distally or proximally relative to the first arm. The holding dock may be configured to lock the suturing element within the second arm.

Some variations of the suture passers described herein are generally configured to pass a suture at least twice through the meniscus, i.e., from the femoral surface of the meniscus to the tibial surface of the meniscus, and back to the femoral surface, or from the tibial surface to the femoral surface and back to the tibial surface.

Any of the variations described herein may be configured to have an elongate body extending from the distal to proximal direction; the distal-to-proximal direction may be referred to as longitudinal, relative to the device. In some variations, the elongate body is relatively stiff or rigid, though flexible, bendable or compliant elongate bodies are also contemplated. In some variations, the elongate body includes a bend near the distal end. The devices described herein may include one or two "arms" located at the distal end. The arm or arms near the distal end are configured to be positioned adjacent to the meniscus. In some variations, the distal end of the device is configured with a pair of arms that are configured to be positioned adjacent to the tibial and femoral faces of the meniscus when the device approaches the meniscus from the inside of the joint (e.g., from the apex of the meniscus); one of the arms may be substantially straight (e.g., in line with rest of the elongate body, and the other arm may be bent at a position proximal to the distal end of the arm, forming the bend. The two arms (bent and unbent) may form an acute opening which may fit around the meniscus when approaching from the meniscus. In variations having a single arm, the single arm may be bent as described above, or it may be straight, relative to the elongate body of the device.

In some variations, both arms are fixed relative to the body of the device. In some variations, the one or more arms are movable. For example, one of the arms may be laterally movable (in the distal/proximal axis) relative to the other arm; in some variations, the bent arm is fixed relative to the elongate axis of the device, while the straight arm is laterally movable. In some variations, the arms are jaws that may be opened and closed (scissorlike) and/or locked into a position (open and/or closed) to either a selectable or predetermined degree.

Any of the variations of suture devices described herein may include one or more tissue penetrators. These tissue penetrators may be referred to as needles, knives, or the like, and are generally elongate members configured to extend through the meniscus tissue. A tissue penetrator typically has sufficient column strength to penetrate the meniscus and pull or push a suture element (e.g., a suture, suture shuttle, loop/suture puller, etc.) through the tissue. In some variations the tissue penetrators include elongate, metal or metallic (e.g., Nitinol) needles, which may be formed of a shape memory material; these needles may include a tissue-penetrating (e.g., sharp, pointed) distal end or may have a rounded end. In some variations, the tissue penetrator comprises a tissue penetrator assembly, including a number of components such as more than one needle, e.g., telescoping needles, sliding blades, etc.

Some variations of the devices described herein may be used with a suturing element. A suturing element may include a suture or any other element configured to draw the suture through the tissue, including a suture shuttle and a pullwire or loop to which one or more sutures may be connected and used to pull the suture through the tissue.

In general, the devices described herein may include a proximal handle having one or more controls for controlling the action of the suture passer. For example, the devices may include a grip or finger grip region at the proximal end (handle) and a control (e.g., trigger) for deploying the tissue penetrator through the tissue. Other controls may be used, or integrated with the trigger or with each other, for example, to control transferring/release of the suture element from the tissue penetrator and/or for moving one or more of the arms at the distal end of the device.

Any of the variations of the devices described herein may include one or more pre-formed knots or knotting/locking elements for use with the suture being passed. In addition, any of the device variations described herein may be used as part of a percutaneous, minimally invasive procedure, including (but not limited to) minimally-invasively repairing the meniscus.

The various devices described herein may address and/or solve problems and challenges faced by other meniscus suture or repair devices. In particular, the devices described herein are configured to fit adjacent (and in some cases over, around or alongside) the meniscus, including one or both of the femoral face and/or tibial face of the meniscus. Thus, the devices described herein may include a narrow distal end region and/or distal shaft region allowing positioning within the narrow confines of the meniscal space. This improvement in geometry may be achieved by reducing the size and/or thickness of the arms. For example, in variations adapted for use with a suture element configured as a suture shuttle that docks on one or more positions on the suture passer, the suture passer may include shuttle docks that are narrow or flatter, allowing the arm on which the shuttle dock is present to be narrow. In some variations the shuttle dock is oriented to minimize the height of the arm. In some variations, the tissue penetrator and/or shuttle and/or shuttle dock may be adapted to minimize the space needed for the shuttle dock, and therefore the thickness of the arm.

Part I describes suture passer devices having two arms that are positionable around the meniscus, along the femoral surface and the tibial surface, and a single tissue penetrator (e.g., needle) that is configured to extend from and retract into one of the arms (a first arm); the tissue penetrator (or tissue penetrator assembly) is configured to exit from the first arm from a first lateral position (along the length) and extend into the tissue to engage or disengage a suture on the opposite (second) arm, and also to exit from the first arm from a second, more proximal lateral position and extend into the tissue to disengage or engage a suture on the second arm at a second location on the second (more proximal) location on the second arm. A control may switch the tissue penetrator or tissue penetrator assembly between the first exit position and the second exit position; a toggle, internal switch, deflector or the like may be used to switch between the two exit positions.

In some variations, the suture passer device may include a two-part tissue penetrator, in which the first part extends from the first arm, and though the meniscus along a first path from the first (e.g., distal) lateral position and the second part is configured to either adjust the trajectory of the first part so that it extends from the first arm along a second path from the second (e.g., proximal) lateral position, or the second part is configured to receive the suture (or suturing element) from the first part and extend from the first arm along a second path from the second (e.g., proximal) position. In some variations the two-part tissue penetrator includes a pair of flat or interlocking needles that may slide together and/or separately relative to each other.

Part II of the disclosure illustrates meniscus suturing devices in which two or more tissue penetrators (e.g., needles) are located on the suture passer for passing the same suture. For example, in some variations two tissue penetrators are held on one of the two arms of the suture passer. In one variation, one of the tissue penetrators is configured to pull the suture from the opposite arm through the tissue and hand off the suture to the second tissue penetrator which then pushes the suture back through the tissue at a second location. In some variations, two tissue penetrators may extend simultaneously or sequentially from different lateral positions on a first arm. For example, two tissue penetrators may extend from different lateral locations (e.g., proximal and distal) on the first arm, though the tissue and engage different regions of a suture held on the opposite arm, then pull the suture back though the tissue from either side. In some variations, as mentioned above, the tissue penetrator may be a flat or substantially flat member.

Part III describes meniscus suture passers that include one or more curved tissue penetrator (e.g., needle) extending from a first arm, configured to pass through the tissue and end up back at the same arm, where the suture may be secured. In some variations the device includes only a single arm from which the tissue penetrator extends and retracts, passing the suturing element (suture, suture shuttle, pull-wire/loop, etc). In some variations the device includes a second arm or other deflector surface which helps guide or direct the tissue penetrator back through the tissue to a second location (e.g. proximal or distal to the starting location of the tissue penetrator). In some variations, the device includes a telescoping tissue penetrator that extends through the tissue with a telescoping (or over- or under-sliding element, as in a two-part construction) element.

Part IV describes meniscus suture passers that may include stapling elements having a pair of tissue penetrators that are coupled together by a flexible element (e.g., suture) between them.

Part V describes other embodiments of suture passers, including accessory elements, and methods of use. For example, part V illustrates screw anchors, manual methods of passing a suture to repair a meniscus, and suturing shields to guide the tissue penetrator and/or protect non-target tissue from penetration.

BRIEF DESCRIPTION OF THE DRAWINGS

FIGS. 1A and 1B illustrate the anatomy of the meniscus.

FIGS. 4A-4E illustrate various tear patterns that may be repaired using the invention described herein.

FIG. 6A illustrates a portion of a torn meniscus between a femur and tibia, with a suture passer shown on the right.

FIGS. 6B-6D illustrate insertion of the suture passer surgical device into the joint and around the torn meniscus.

FIGS. 17A and 17B illustrate operation of the distal end of one variation of a suture passer device during a first stitch (FIG. 17A) and a second stitch (FIG. 17B).

FIG. 18 shows an enlarged view of the upper arm of the device shown in FIGS. 17A and 17B, during the formation of a first stitch, in which the tissue penetrator is engaging with a suture shuttle releasably held in the upper arm.

FIG. 19 shows an enlarged view of the upper arm of the device shown in FIGS. 17A and 17B during the formation of the second stitch (FIG. 17B), in which the tissue penetrator is disengaging the shuttle so that it can be held in the receiving dock in the upper arm.

FIGS. 20A and 20B show side perspective and side views, respectively, of another variation of a dock region configured to accommodate a pull wire.

FIGS. 24A and 24B show another variation of a dock such as a release dock and/or holding dock for securing a suturing element. In this variation an elastomeric material (FIG. 24B) is included to secure a suturing element (e.g., shuttle) within the dock.

FIGS. 26A-26C illustrate another variation of a dock for releasably securing a shuttle within an arm of a suture passer. In this variation, the dock includes a spring-loaded latch and pawl.

FIG. 28 illustrates an enlarged view of one variation of a pull wire.

FIGS. 29A and 29B illustrate other variation of a suture and pull wire.

FIGS. 30A and 30B illustrate one variation of a suture device including arms adapted for use with a pull wire. In particular, these variations include cut-out regions allowing passage of the pull wire as it is passed between the arms during use.

FIGS. 32A-32B illustrate operation of another variation of tissue penetrator and shuttle, in which the shuttle is hypotube having retaining features (e.g., tabs) that may be secured/released from the tissue penetrator having a matching rounded cross-sectional profile.

FIGS. 33A-33C illustrate another variation of tissue penetrator and shuttle, similar to that shown in FIGS. 32A-32B.

FIGS. 35A-35G illustrate another variation of a tissue penetrator and shuttle, in which the needle and shuttle are keyed to engage/disengage as the tissue penetrator is extended and retracted between the first and second arms of the suture passer.

FIG. 36A-36C illustrate one method of placing two lead wires to pull a suture loop through the meniscus.

FIG. 37A shows another variation of a vertical loop stitch placed by a suture passer as described herein, and extending from the upper outer surface (superior surface) of the meniscus to the lower outer surface (inferior surface) of the meniscus.

FIGS. 37B and 37C illustrate a lateral loop of suture placed by a suture passer as described herein, showing a view of the superior surface (femur facing side) of the meniscus in FIG. 37B and the inferior surface (tibial facing side) of the meniscus in FIG. 37C.

FIGS. 42A-42E illustrate variations of tissue penetrating elements which may be used with some of the suture passers described herein.

FIGS. 43A-43D illustrate additional variations of tissue penetrating elements which may be used with some of the suture passers described herein.

FIGS. 46A-46K illustrate variations of tissue penetrating elements which may be used with some of the suture passers described herein.

FIGS. 47A1 and 47A2 show one variation of a tissue penetrator configured as a grasper.

FIGS. 47B-47D3 illustrate additional tissue penetrators configured as graspers.

FIG. 48A shows one variation of a suture passer as described herein.

FIGS. 48B-48H illustrate operation of the suture passer shown in FIG. 48A.

FIG. 51 shows the distal end region (in partial cross-section) of another variation of a suture passer having two parallel tissue penetrators.

FIGS. 52A and 52B show partial views of tissue penetrators for use with suture passers including the variation shown in FIG. 51.

FIGS. 54A-54C show partial views of another variation of a meniscus suture passer configured so that two tissue penetrators hand off a suturing element between them when used to suture a meniscus.

FIGS. 54D and 54E illustrate side perspective views of the tissue penetrators used with the suture passer of FIGS. 54A-54C.

FIGS. 56A-56C illustrate operation of the tissue penetrators for the suture passer shown in FIG. 55.

FIGS. 56D and 56E illustrate both of the tissue penetrators used with the suture passer shown in FIG. 55.

FIGS. 59G1 and 59G2 illustrate another variation of a meniscus suture passer configured to pass a suture twice through a meniscus.

FIGS. 59H1 and 59H2 illustrate another variation of a meniscus suture passer configured to pass a suture twice through a meniscus.

FIGS. 59*i*1 and 59*i*2 illustrate another variation of a meniscus suture passer configured to pass a suture twice through a meniscus.

FIGS. 61A-61D show another variation of a tissue penetrator for a suture passer configured for use with a suture shuttle.

DETAILED DESCRIPTION OF THE INVENTION

Figure 2:
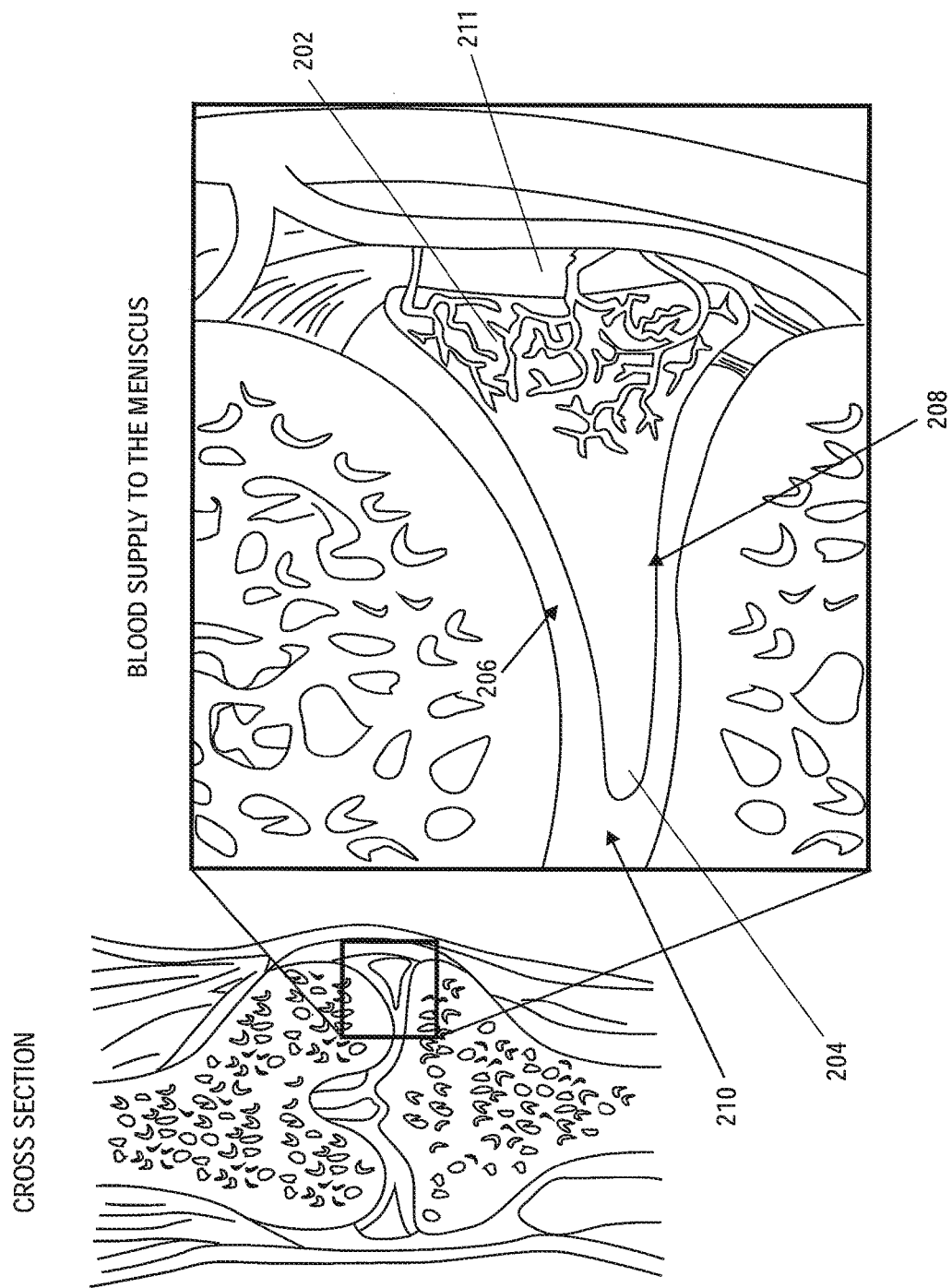
FIG. 2 illustrates the anatomy of the meniscus, including the capsule and associated vascular tissue.

Described herein are suture passers for meniscus repair. In general, these devices may be referred to herein as meniscus repair suture passers, meniscus repair devices, or simply suture passers. The devices described herein may be configured to repair a meniscus (knee joint meniscus), and have a distal end region that has two arms, at least one of which is extendable and retractable distally/proximally along the longitudinal axis of the device (e.g., "longitudinally). The device has a deployed configuration with a distal-facing opening configured to fit around the tapering outer surfaces (e.g., the superior and inferior surfaces) of a meniscus. The device also has an insertion configuration in which one arm (e.g., the bent or angled arm) extends distally beyond the other arm of the device. One or more additional operational configurations may be formed intermediate to these two positions, and the device may be switched between these configurations by retracting or extending one or both arms.

The deployed configuration having a distal-facing opening is typically configured to fit around the inner portion of a meniscus. In some variations, this means that one arm is typically bent, angled or bendable into an angled form, where in the angle refers to the angle between the arm and the elongate body of the device. For example, the device may form a V-shaped opening which can fit around a meniscus from a lateral (central) approach. Thus, the distal end of the device is divided up into two arms (one of which may be an extension of the elongate body of the device). One of the arms is bent, curved, or bendable relative to the other arm and relative to the long axis of the body of the device. At least one of the arms is movable distally/proximally relative to the other arm, which may be used to form the angled opening at the distal end region (e.g., the distal-most 3 or less cm) of the device.

In one variation, a first arm is bent, curved, or bendable at an angle away from the long axis of the device, and the second arm is straight (e.g., parallel or in-line with the long axis of the device). Either the bent or straight arm, or both, is movable distally and proximally (in the direction of the long axis of the device) relative to the other arm. Retracting one of the arms proximally relative to the other arm will form an acute angled opening at the distal end of the device that can be positioned around the meniscus, and a suturing element can be passed between the arms through the meniscus to repair the meniscus.

The devices described herein are further configured to pass a suturing element between the two arms and thereby pass the suture through the meniscus. In some variations, the devices are configured to pass a suturing element at least from one arm to the other and back to the first arm. In some variations, the suture passer may be adapted to pass multiple times between the two arms, or an unlimited number of times. In some variations, the suture passer is configured to pass just twice (e.g., from the first arm to the second arm, and back to the first arm).

In general, these devices include a tissue penetrating element that is capable of extending between the two arms when the device is in the deployed and intermediate configurations to pass a suturing element through tissue. The tissue penetrator may releasably mate with a suturing element (e.g., suture shuttle, suture, and/or wire lead), and may pass the suturing element from a first arm to a second arm, and back to the first arm. The arm opposite to the tissue penetrating element may have one or more seat/docks for releasably or permanently holding the suturing element.

In some variations, the suturing element is a staple. For example, a staple may act as both the tissue penetrating element (or elements) and the tissue fixation element. A staple may include two tissue penetrating legs and a join region. The tissue penetrating legs of the staple may extend from a first arm through the meniscus where they contact a deflector or, alternatively, an anchor, on the second arm positioned on the opposite side of the meniscus. The tissue penetrating legs may then be secured (by deflection or otherwise anchoring) on the opposite side of the meniscus. In general, a staple may be secured across (e.g., may span) a tear in the meniscus.

Thus, the meniscus repair suture passer devices described herein may pass a suture two or more times through the meniscus so that the suture passes from the upper to the lower outer surfaces of the meniscus. The angle and/or position of the device may be adjusted as necessary before and during the procedure, including between passing the suture through various portions of the meniscus. Thus, the meniscus repair suture passers describe herein are adapted for percutaneous use.

In general, a system including a suture passer as described herein may include a first arm, a second arm, a suture-passing tissue penetrating element (e.g., needle), a suturing element to be passed between the two arms, and one or more docks for retaining and/or releasing the suturing elements. In some variations the tissue penetrating element is a pre-bent wire, ribbon or needle element that is configured to extend from the first or second arm (from which it may be extended and retracted), through tissue (or air), and approach the second or first arm, where it may engage or disengage (alternately or cyclically) a suture shuttle held in a shuttle dock. In some variations, the first arm of the suture passer may be configured for distal/proximal movement, e.g., forward and backwards axially along the long axis of the device. The suture passer may be configured to include two or more stops corresponding to different operational configurations. For example, the device may include a first stop in which one arm is fully retracted axially, forming the distal opening for the meniscus, and a second stop (extended stop) when one arm is fully extended distally forming a device having bent distal end (formed by the extended arm). In some variations the suture passer includes a third or more (e.g., intermediate) stop(s) in which an arm is partially extended distally.

Figure 7:
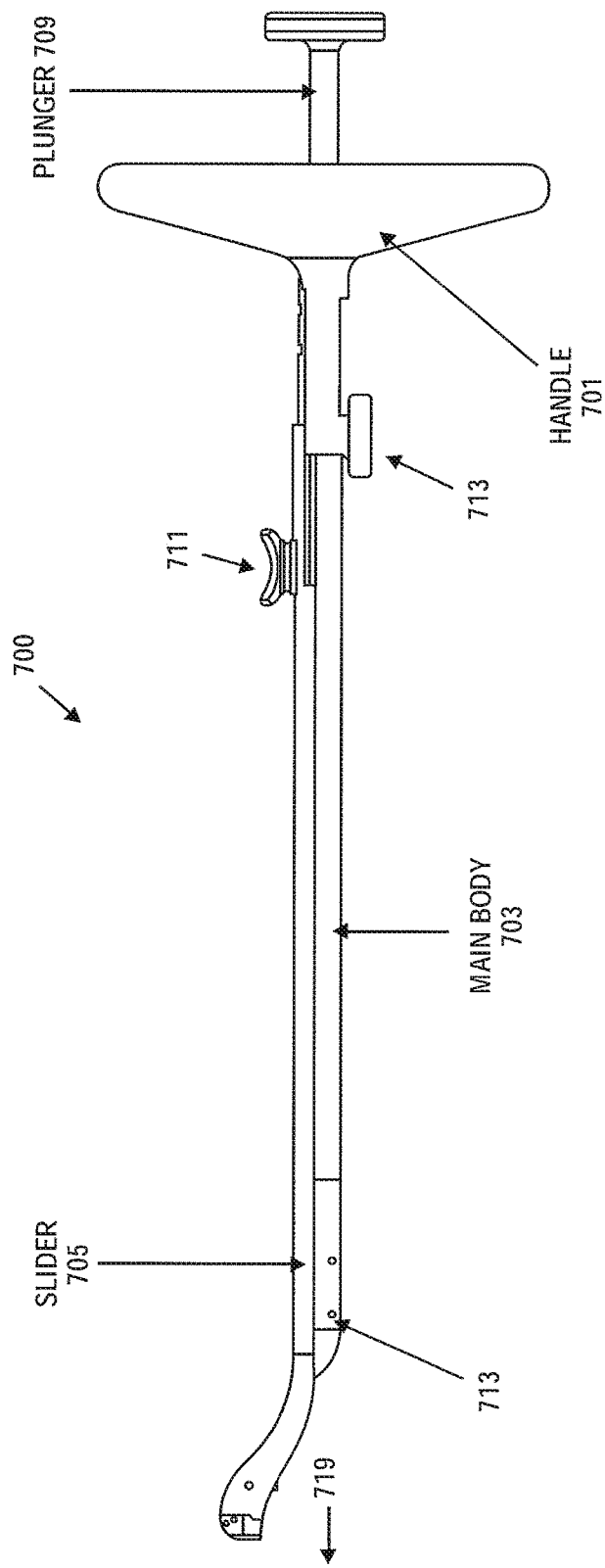
FIG. 7 illustrates one variation of a meniscus suture passer in a delivery configuration, wherein the angled distal arm is extended beyond the opposite arm.

FIG. 7 illustrates one variation of a meniscus suture passer 700, as described herein. In this example, the suture passer includes an elongate main body 703 extending the length of the device. The proximal end of the device 700 includes a handle 701. The distal end of the main body 703 of the device may be referred to as a first arm forming the distal end of the device. A slider 705 is movably coupled to the main body. The distal end of the slider 705 forms the second (e.g., "upper") arm. Sliding the slider 705 proximally relative to the first arm (and main body 703) will result in the formation of an angled opening. The opening is roughly V-shaped, in which one side is substantially flat while the other side is angled relative to the flat side.

In FIG. 7, the distal end of the slider is rounded or blunted to prevent damage to the meniscus when operating the device. In some variations the distal end of the slider (angled or second arm) may be enlarged relative to the more proximal region of the slider. The slider may also include a slider control (e.g., finger control 711) which may be manipulated manually or automatically to move the slider distally or proximally. A similar control on the opposite side (e.g., on the main body) may also be included to slide the first arm (the main body) relative to the slider when it is desirable to hold the slider in a fixed position relative to the patient, for example.

As mentioned, one or more arms of the suture passer may be bent or curved. In the example shown in FIG. 7, the second (slider) arm of the device is bent or angled "upwards" away from the first arm, or from the long axis of the device, including the first arm, so that the ends region of the second arm (the upper arm) relative to the long axis is bent at approximately the angle formed by the superior surface of a meniscus relative to the inferior surface of the meniscus. The angle may be fixed (e.g., at an acute angle of approximately 10°, 15°, 20°, 25°, 30°, 35°, 40°, 45°, 60°, etc. including any angle between 1° and 90°); for example, the angle may be between 20 degrees and 50 degrees. In some variations, the angle between the first and second arms is variable. In some variations the angle is adjustable (e.g., either or both arms may be bent or adjusted to adjust the angle there between). The angle of the bend in the upper (second) arm may be approximately the average angle between the superior and inferior faces of the meniscus; for example, the angle may be approximately 35 degrees ±2 degrees, ±5 degrees, ±7 degrees, ±10 degrees, ±15 degrees, etc. In general the bend forms an acute angle with the lower (second) arm when the second arm is extended distally. In some variations, as mentioned, the distal end region of the second arm may be bendable from a straight or pre-bent configuration into the final bend configuration.

In the variation shown in FIG. 7, a tissue penetrator (not shown) is housed within the first arm 713, which in this example is integral with the main body 703. In FIG. 7, the first arm extends distally, in-line with the proximal-distal axis of the elongate main body; in some variations the first arm is separate from the main body, but extends in parallel with the distal/proximal axis of the main elongate body of the device. A second, bent arm formed by the slider 705 may include one or more shuttle docks. The second arm may also be referred to as the slider, since it is slideably coupled with the elongate body (e.g., main body) and/or the first arm of the device. As shown in FIG. 7, the distal end of the second arm extends at an angle from the main body. In this example, the angle is not constant over the entire length, as the distal tip of the second arm is rounded (having a region almost in parallel with the long axis of the elongate body and first arm). When the second arm is retracted relative to the first arm (or, relative to the second arm, when the first arm is extended) an acute-angled, distal-facing 719 opening is formed between the first arm and the second arm which may be positioned around the apical region of a meniscus, e.g., the tapered region opposite from the capsular region. FIGS. 17A and 17B, described in greater detail below, show the acute-angled opening formed by the first and second arms.

As mentioned, in the exemplary device shown in FIG. 7 the second, upper arm (slider) include one or more seats or docks (e.g., shuttle dock) for holding a suturing element within the second arm. The device of FIG. 7 is configured to have two docks. One of these docks may be configured as release dock which may hold the suturing element (e.g., suture, suture shuttle and/or lead wire) within the dock and release the suturing element from the dock to engage the tissue penetrator; the second dock may be identical to the first dock, or it may be configured as a holding dock that is configured to receive the suturing element from the tissue penetrator but not release it back to the tissue penetrator. The first dock and the second dock may be separated from each other along the length of the second arm. For example, in some variations a release dock is located near the distal tip of the second arm and a holding dock is located proximal to the release dock. In some variations these positions are reversed. In some variations the second arm includes more than two docks. The release dock may be pre-loaded with a suturing element.

As mentioned, a shuttle dock may be configured to releasably engage a suture shuttle (or other suturing element). The suture shuttle may be passed between a shuttle dock and the tissue penetrating element that may extend between the first and second arms. For example, a tissue penetrator may extend from within a first arm, though the meniscus tissue, and engage a suture shuttle held in a dock in the second arm; the tissue penetrator with attached shuttle may then retract back through the tissue to the first arm. If a pull wire and/or suture is attached to the shuttle, the distal end of the pull wire and/or suture will be pulled back from the second arm to the first arm. Thereafter, the first arm may be retracted proximally relative to the second arm, or the device may be otherwise repositioned on the meniscus (without requiring that the device be removed from the meniscus). The tissue penetrator may then be passed back through the tissue to engage either another shuttle dock, or the same (first) shuttle dock, and release the suture shuttle within this dock; the tissue penetrator may again be withdrawn, leaving the suture and/or lead wire stitched through the meniscus from a first (e.g., superior) surface of the meniscus to an opposite (e.g., inferior) surface of the meniscus and back to the first surface of the meniscus. Additional stitches may be made, or the device may be withdrawn from the knee and the suture pulled taut and secured in position.

Suture shuttle and tissue penetrating element may be configured as described in the descriptions previously incorporated by reference (e.g., U.S. Ser. No. 11/773,388 and U.S. Ser. No. 12/291,159). For example, the shuttle may be a clip (e.g., a triangular-shaped clip) to which a suture is secured; the clip may be configured to snap on an off of the tissue penetrating element (e.g., a curved needle having a triangular cross-section). In some variations, the suture shuttle with a suture attached is pre-loaded into a shuttle dock on the first arm of the device. FIGS. 10A-16C, described in more detail below, illustrate variations of suture shuttles and tissue penetrators which may be used.

In general a tissue penetrator or penetrating element is held within and extended from and retractable into one arm of the suture passer. Once it exits the arm of the suture passer, the tissue penetrator extends across the gap between the two arms, through any intervening meniscus tissue, where it can transfer a suturing element between its distal tip region and a dock or seat on the opposite arm. Ideally, the suture passer follows a predetermined pathway between the two arms of the device, so that it reliably encounters the dock and can exchange the suturing element (e.g., suture shuttle). Further, the distal end region of the tissue penetrator may be adapted to releasably engage the suturing element and also to allow penetration though the tissue.

In some variations the tissue penetrator is a curved member that retracts or extends from one of the arms. In particular, a tissue penetrating member may be a curved or curvable element that retracts completely into a housing in the distal end region of the first arm, and extends outwards in a curved pathway. In some variations, the tissue penetrator may be configured to extend from the distal end region of the second arm, and to retract fully into the body of the second arm; in some variations a portion of the tissue penetrating member may extend from the first arm even when fully retracted into the first arm. The second arm or other portions of the suture passer may be configured to include a track or pathway for the tissue penetrating member so that the tissue penetrating member does not prevent the first arm from extending or retracting axially relative to the body of the device.

In some variations, the tissue penetrator is pre-bent or pre-curved into a curved shape configured to allow the tissue penetrator to pass in a curved or arced pathway from within a first arm and across the gap between the first and second arms, and engage a seat or dock on the second arm. Thus, the tissue penetrator may be formed of any appropriate material, including shape-memory materials. For example, the tissue penetrator may be formed of a shape memory polymer or alloy. In some variations the tissue penetrator comprises a nickel titanium material (e.g., Nitinol).

The tissue penetrator is typically pushed and/or pulled to extend and retract it from the first arm. For example, the proximal end of the tissue penetrator may be connected to a push/pull rod.

Figure 8:
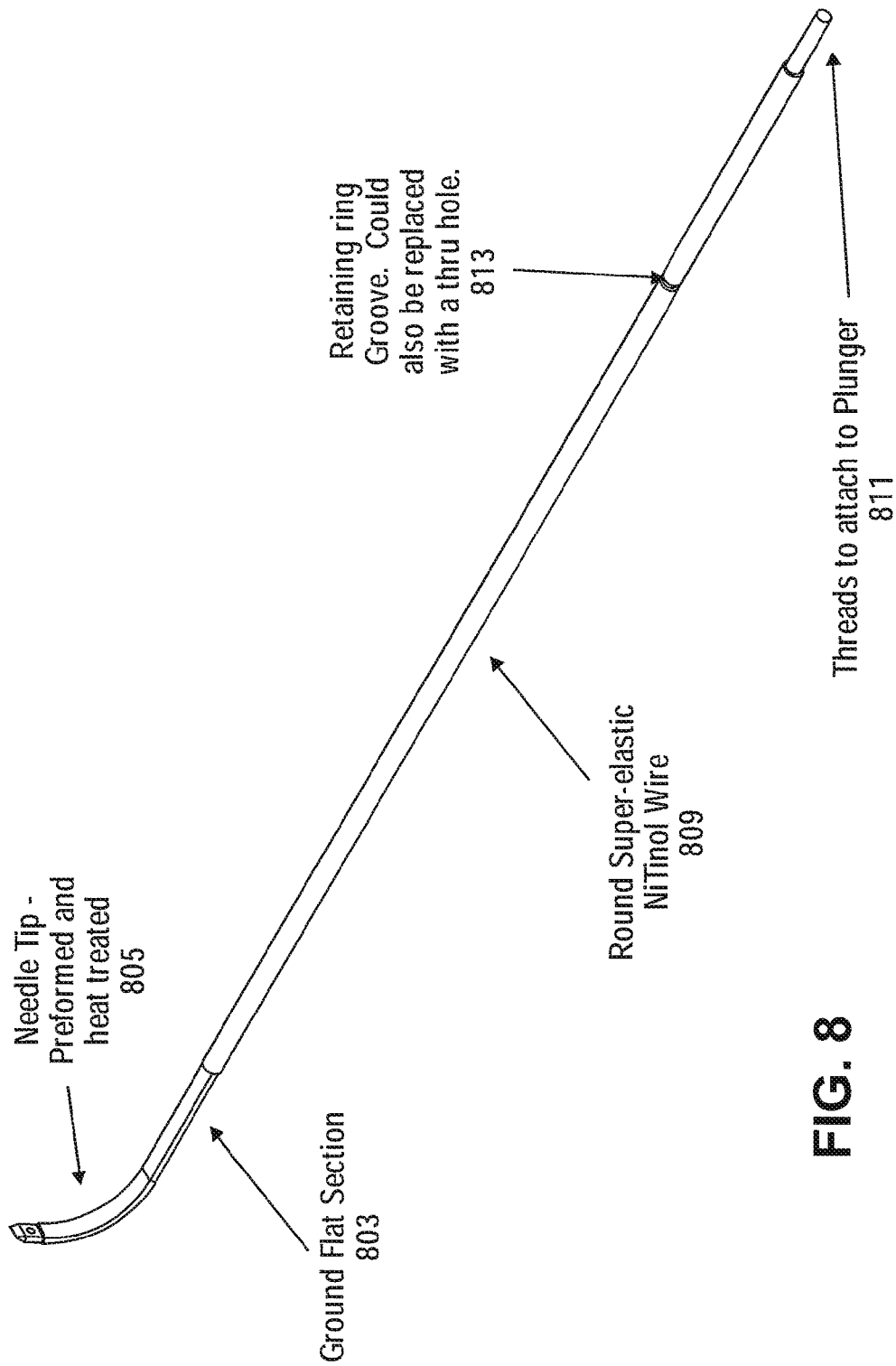
FIG. 8 shows one variation of a tissue penetrator configured as an elongate needle formed at the end of a shape memory push rod.

For example, FIG. 8 illustrates one variation of a preformed tissue penetrator formed as part of a nickel titanium push rod or wire. In this example, the tissue penetrator, which may also be referred to as a needle, if formed at, or otherwise joined to, the distal end of the rod or wire 809. The distal end in this example has been flattened (e.g., by grinding) and pretreated to form the needle tip with a curve 805, as shown. The distal end has therefore been ground flat 803, and is continuous with an elongate rod length 809. Near the proximal end, the rod has been modified to include a retaining structure, e.g., ring, for holding the device within the suture passer while allowing it to be extended and retracted for operation. The proximal end in this example also includes a threaded region to connect to a plunger and/or handle member that allows the rod to be advanced and withdrawn within the elongate body of the suture passer (and the first arm) to extend and retract the tissue penetrator. In some variations all or a portion of this tissue penetrator assembly is keyed to prevent rotation of the needle. For example, the body may include a groove or a protrusion to mate with a channel or other element within the suture passer and prevent rotation.

Thus, the variation of the device described in FIGS. 7 and 8 utilize a one piece pre-formed Nitinol needle that has been heat set into the desired shape. In some variations, the entire length of the needle may be made from a flat wire; alternatively, the entire length may be made from a round wire, as shown in FIG. 8 (which may be partially or complexly ground or otherwise shaped to include the necessary flat regions. In some variations, the needle (tissue penetrator) assembly is formed of a combination of a round wire for the proximal shaft with a distal end ground/cut flat. This configuration may allow sufficient stiffness and axial push to drive the penetrator through tissue, but enable sufficient flexibility at the distal tip so it can be shape set.

As mentioned, in general the distal end region of the tissue penetrator is configured to receive a suturing element such a suture shuttle. In particular, the region of the tissue penetrator just proximal to the most distal tip region may be configured to retain a suture shuttle or other suturing element. The most distal region (the actual distal tip) is typically tapered and/or sharpened to allow the device to penetrate though the tissue. In some variations the distal tip region is shaped to receive, retain and/or release a suturing element. For example, FIGS. 9A and 9B illustrate one variation of a distal tip of a device that is shaped to penetrate the meniscus tissue while retaining (and later releasing) a suture shuttle.

Figures 9A, 9B:
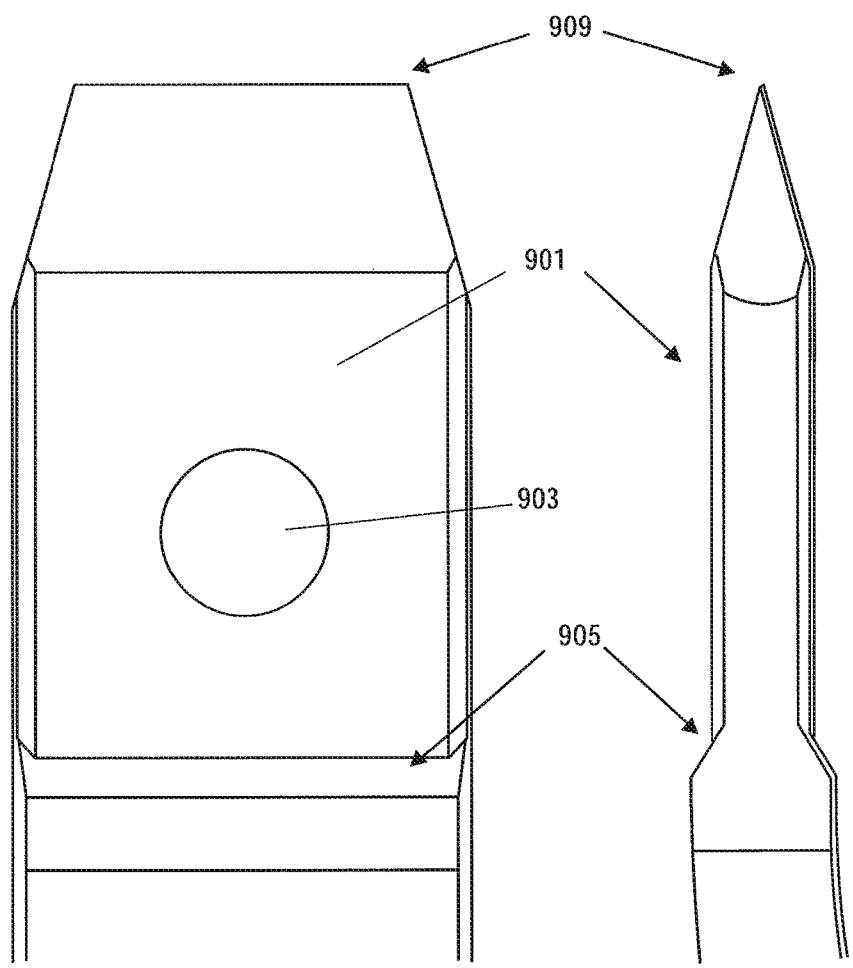
FIGS. 9A and 9B show one variation of the distal tip region of a tissue penetrator, having a flattened profile and a mating surface for a suture shuttle.
Figure 10B:
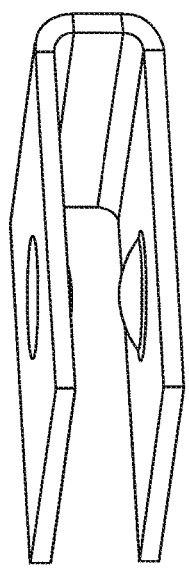
FIGS. 10A-10E show top, side, perspective side and perspective views, respectively of one variation of a suture shuttle configured to mate with a tissue penetrator such as the tissue penetrator show in FIGS. 8 and 9.
Figure 10C:
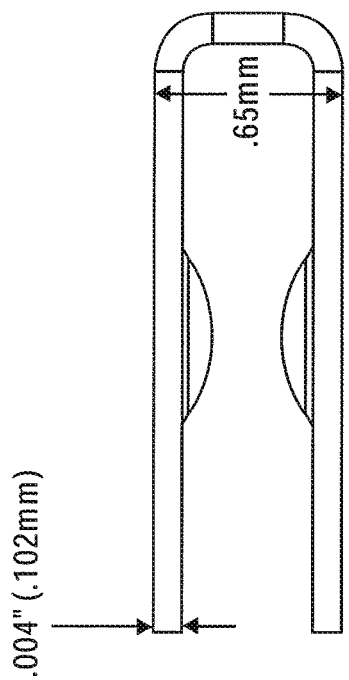
Figure 10A:
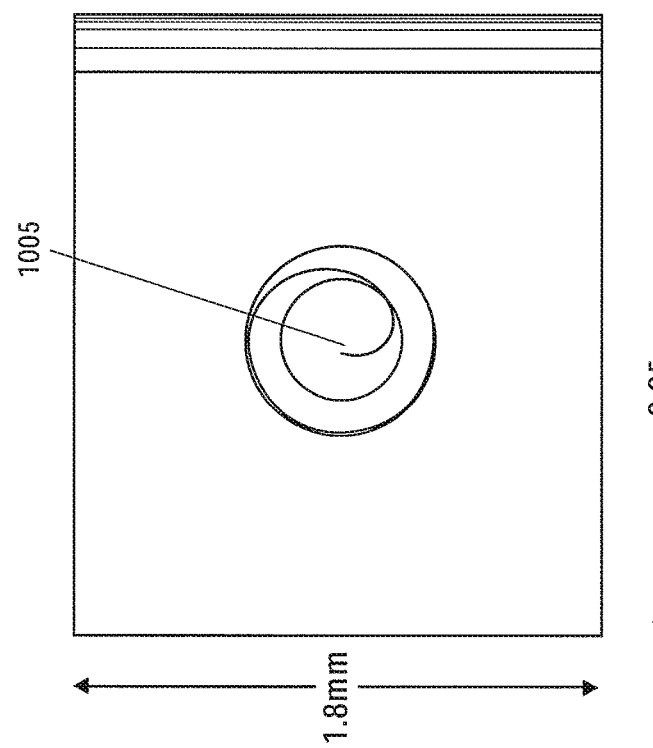
Figure 10E:
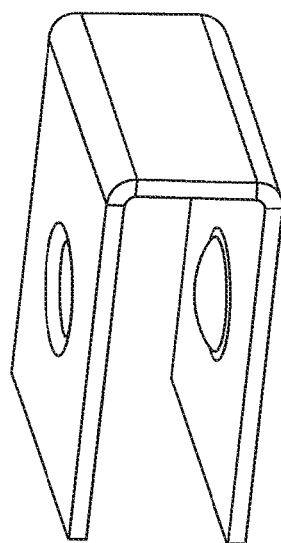
Figure 10D:
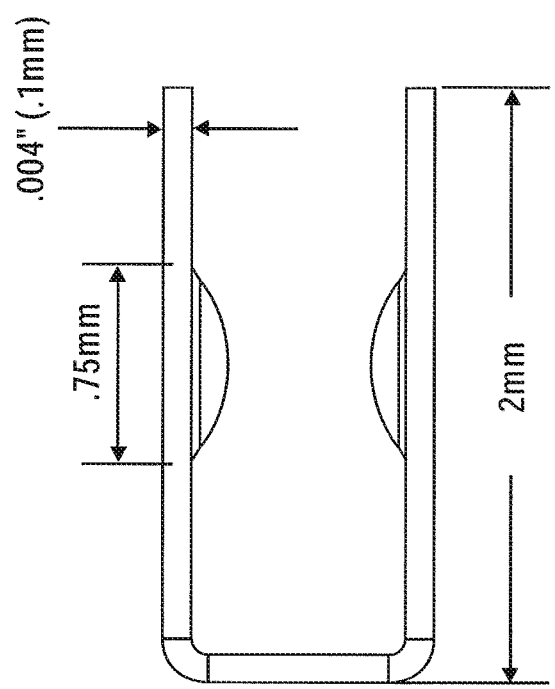

In FIGS. 9A and 9B, the distal tip region is configured to receive a shuttle by including a recessed region 901 that allows the shuttle to be held by the needle with a low profile. The distal tip region also includes a hole or opening 903 to mate with dimple on the suture shuttle; in some variations other mating elements (e.g., buttons, tabs, slots, etc. may also be included to mate the tissue penetrator with the suture shuttle. The tissue penetrator also includes a stop 905 against which the shuttle may be held in position. This recessed region is configured to match the approximate size of the inner diameter of the shuttle such that the outer diameter of the shuttle matches the outer diameter of the tissue penetrator, forming a flush connection between the two components.

In FIG. 9A, the very distal tip 909 of the tissue penetrator is sharpened and/or tapered. The tissue penetrator variation shown in FIGS. 9A and 9B is a flattened (ribbon-like) tissue penetrator, having a roughly rectangular cross-section. This variation may be referred to as a rectangular needle.

FIGS. 10A-10E illustrate one variation of a suture shuttle that may be used. In general, a suture shuttle may be used to connect the tissue penetrator with a suture or with a lead wire that may be passed through the tissue to form a suturing pattern. The suture shuttles illustrated herein are typically clip-on or snap-on (e.g., snap-fit) elements that secure over and/or around the distal end region of the tissue penetrator and with a dock or seat on an arm of the suture passer. Other variations may include internal structures that are held within the tissue penetrator, shuttles that are held by non-friction fit methods (e.g., magnetically secured, chemically secured, etc.).

In many of the suture shuttles described herein the suture shuttle is configured to resiliently fit over the tissue penetrator distal tip and reside on a region proximal to the distal tip. Thus, in some variations, the suture shuttle includes a flex region or point allowing it to flex "open" to fit over the tissue penetrator. For example, in FIG. 10A-10E, the suture shuttle is partially or completely open on at least one side, and is formed of a resilient material, such as a metal alloy. Any appropriate biocompatible material may be used, including stainless steel, plastic, alloys, shape memory materials (e.g., Nitinol), or the like. For example, in FIGS. 10A-10E the suture shuttle comprises stainless steel (17-7PH or MP35N).

The shuttle illustrated in FIGS. 10A-10E may also be referred to as spring form shapes that snap onto the tip of the needle. The dimensions shown in any of the figures herein are intended for exemplary dimensions only, and may be adjusted without deviating from the principles of the invention. Any of these dimensions may be adjusted by a percentage of their indicated value; for example, any of the dimensions may be adjusted by ±2%, ±5%, ±10%, ±20%, ±30%, ±50%, ±100%, ±150%, ±200%, etc.

Any of the shuttle variations described herein may also include one or more locking or retention features. For example, in FIGS. 10A-10E, the shuttle includes a dimple 1005 or protrusion that is configured to mate with a mating feature (e.g., hole or recess) in the tissue penetrator to retain the shuttle on the tissue penetrator.

Figure 11B:
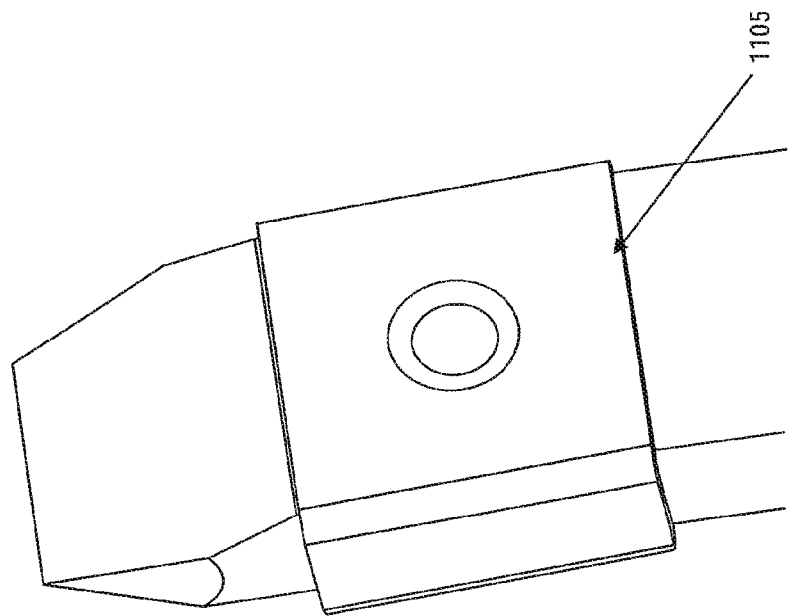
FIGS. 11A and 11B illustrate attachment of a suture shuttle such as the suture shuttle variation shown in FIGS. 10A-10E to a tissue penetrator such.
Figure 11A:
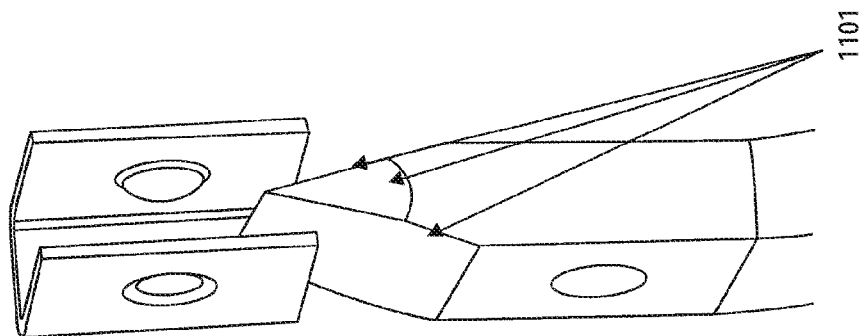

FIGS. 11A to 11B show the attachment of a suture shuttle such as the one in FIGS. 10A-10E to the distal end region of a tissue penetrator. In this example, the distal tip of the tissue penetrator is narrower and smaller (e.g., tapered) 1101 than the opening into the shuttle and the shuttle snaps over the distal tip region so that the protrusion on the shuttle mates with the depression or hole on the tissue penetrator (this arrangement may be reversed so that the protrusion is on the tissue penetrator, for example). The suture shuttle in this example is not held in a recess flush against the outer surface of the tissue penetrator; this configuration may be useful when stripping the shuttle off of the tissue penetrator to transfer it into a dock after passing through the tissue. For example, the back edge of the shuttle 1105 extending above the tissue penetrator may serve as a contact to apply force to remove the shuttle from the tissue penetrator.

Figure 11D:
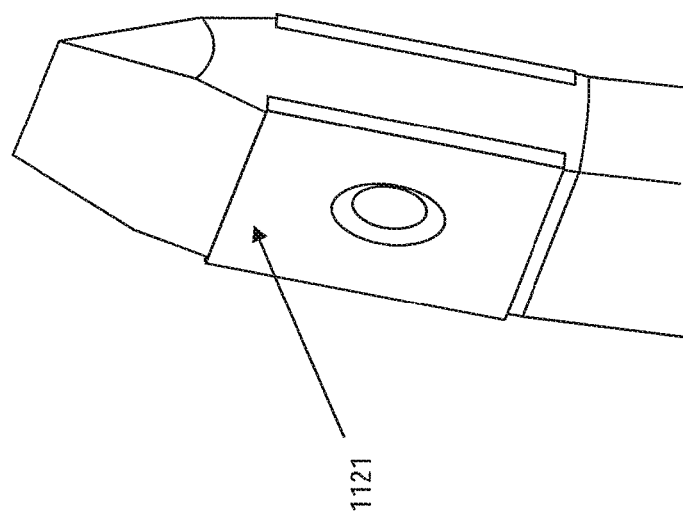
FIGS. 11C and 11D illustrate attachment of a suture shuttle such as the shuttle shown in FIGS. 10A-10E to a tissue penetrator such as the variation shown in FIGS. 8 and 9 having a recessed region for receiving the suture shuttle flush against the tissue penetrator.
Figure 11C:
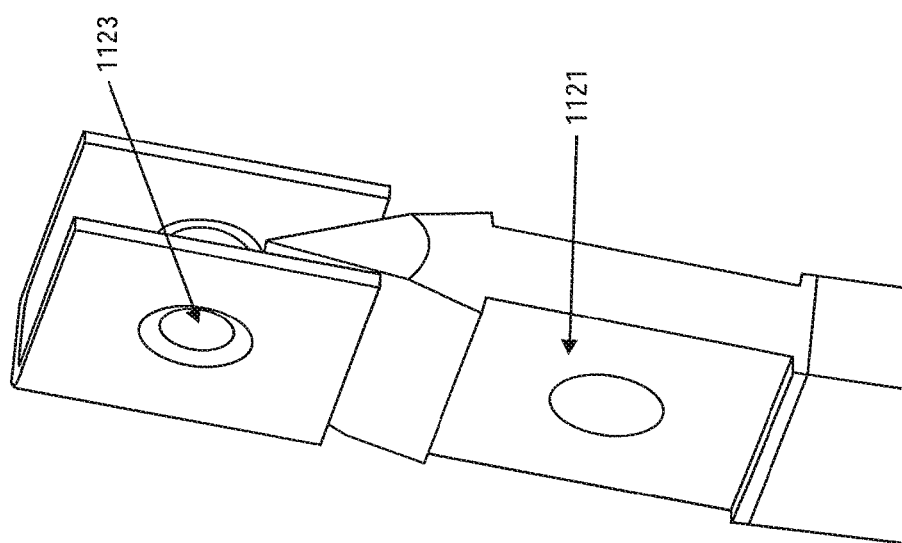

In contrast in FIGS. 11C and 11D illustrate a variation of a tissue penetrator in which the shuttle is held flush with the rest of the needle within a pocket formed (e.g., ground) into the needle. As in the previous example, the dimple or protrusion on the shuttle may help secure and position the shuttle on the tissue penetrator.

Figure 11F:
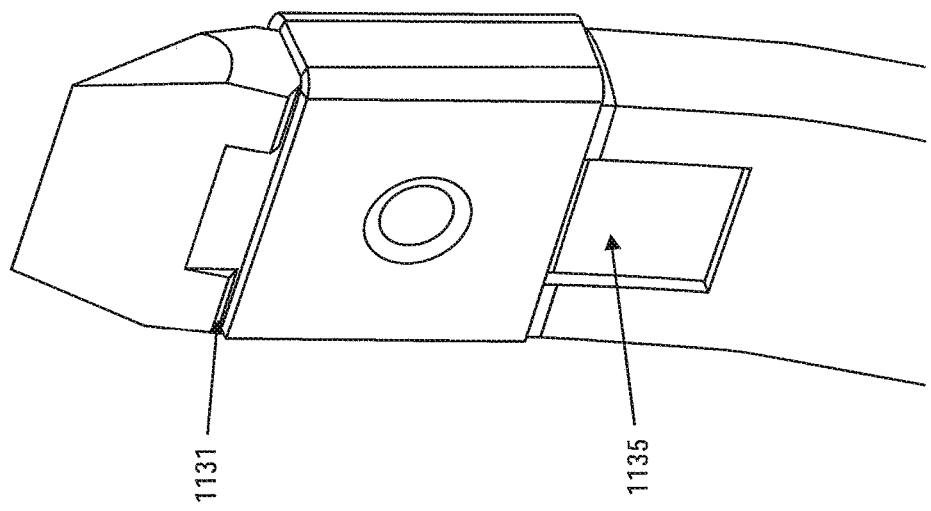
FIG. 11F illustrate attachment of a suture shuttle such as the shuttle shown in FIGS. 10A-10E to a tissue penetrator having a recessed region for receiving the suture shuttle flush against the tissue penetrator as well as a stripping surface formed by a channel in the tissue penetrator to aid in removal of the shuttle from the tissue penetrator.
Figure 11E:
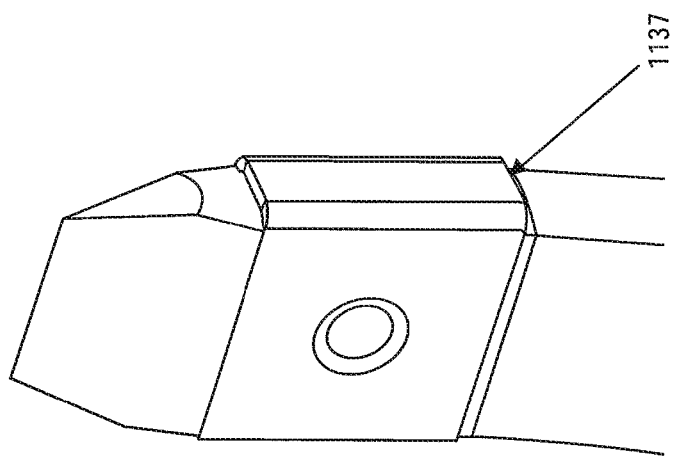
FIG. 11E illustrates attachment of a suture shuttle such as the shuttle shown in FIGS. 10A-10E to a tissue penetrator having a recessed region for receiving the suture shuttle flush against the tissue penetrator forming a stripping surface on the side to aid in removal of the shuttle from the tissue penetrator.
Figure 11H:
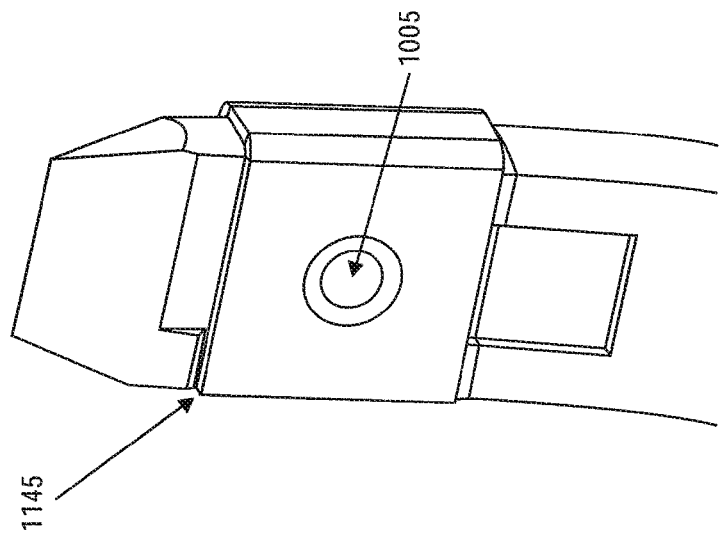
FIGS. 11G and 11H illustrate attachment of a suture shuttle such as the shuttle shown in FIGS. 10A-10E to another variation of a tissue penetrator having a recessed region for receiving the suture shuttle flush against the tissue penetrator as well as a stripping surface to aid in removal of the shuttle from the tissue penetrator.
Figure 11G:
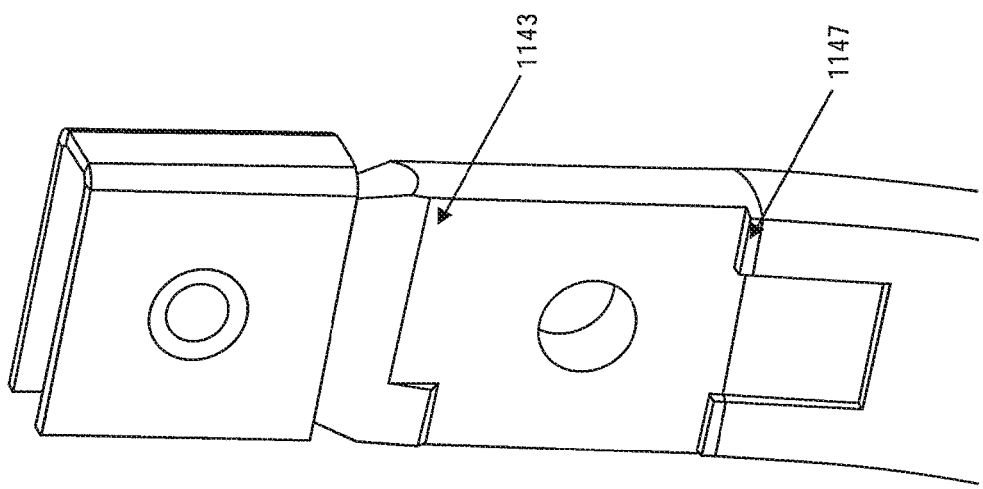

FIGS. 11E and 11F show variations of tissue penetrators which also include a recessed region for holding the shuttle flush against the tissue penetrator, however these versions also include leverage points located proximally on the distal end region (proximal to the seating region) for helping remove the shuttle from the tissue penetrator. For example, in FIG. 11E the needle is narrower in width than the shuttle, so that one side of the shuttle extends slightly from the tissue penetrator 1137 when the suture shuttle is held on the needle; the dimple/protrusion may help maintain this position. This lip region may provide a surface that can be used to remove the shuttle from the needle (e.g., to strip it off of the needle) when transferring the shuttle to a dock. Similarly, in FIG. 11F, the needle includes a groove or channel 1135 in the inner radius of the need exposing the proximal-facing edge of the shuttle, even though the shuttle resides within a pocket 1131 in the distal end region of the device 1131. FIGS. 11G and 11H illustrate a similar variation of the needle. In this variation, a portion of the proximal edge of the recess on the tissue penetrator has been removed 1143, preventing it from interfering with the corners of the shuttle as it is inserted onto the needle or removed from the needle. FIG. 11G also illustrates the stop features 1147 formed at the proximal end of the recess which may help position the shuttle on the needle. In this variation the protrusion may not be necessary given the recess formed on the needle, as well as the snap feature (proximal recess edge 1145) which may also help to secure the shuttle on the needle.

Figure 12A:
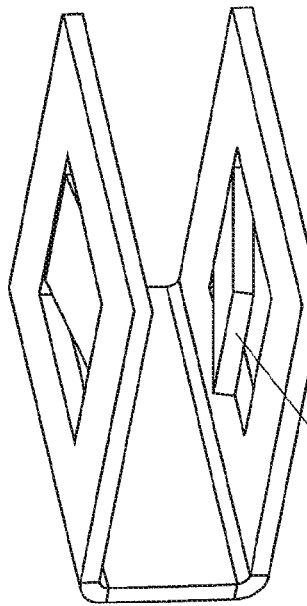
FIGS. 12A-12C show additional variations of rectangular suture shuttles.
Figure 12B:
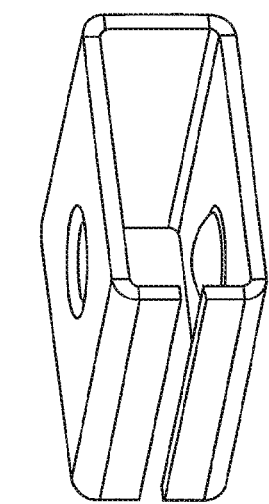
Figure 12C:
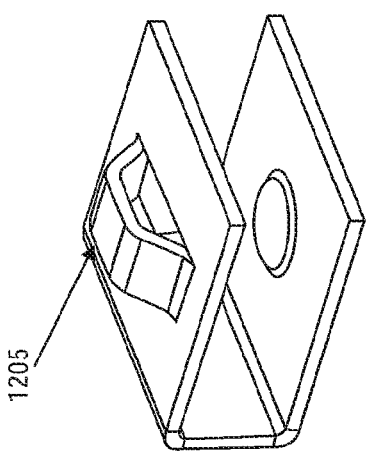
Figure 13A:
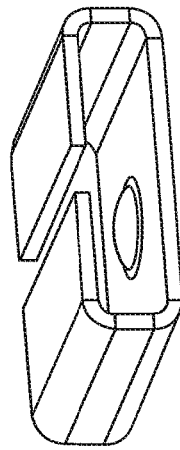
FIGS. 13A-13C show side, perspective and top views, respectively, of another variation of a suture shuttle.
Figure 13B:
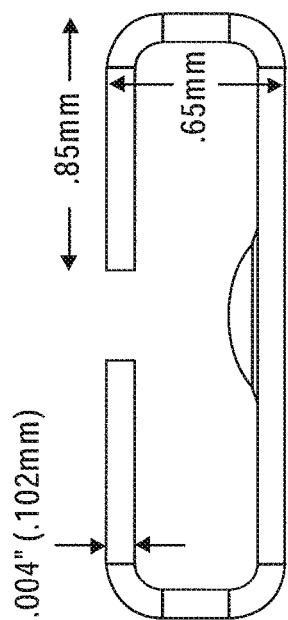
Figure 13C:
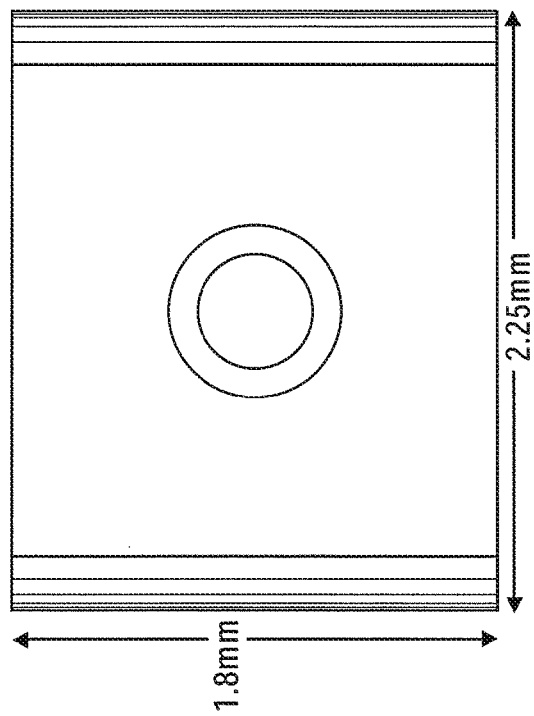
Figure 13E:
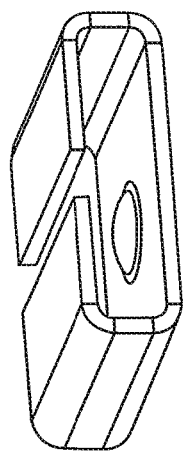
FIGS. 13D-13F show side, perspective and top views, respectively, or another variation of a suture shuttle.
Figure 13D:
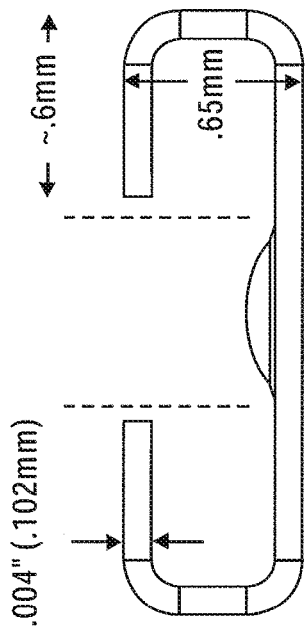
Figure 13F:
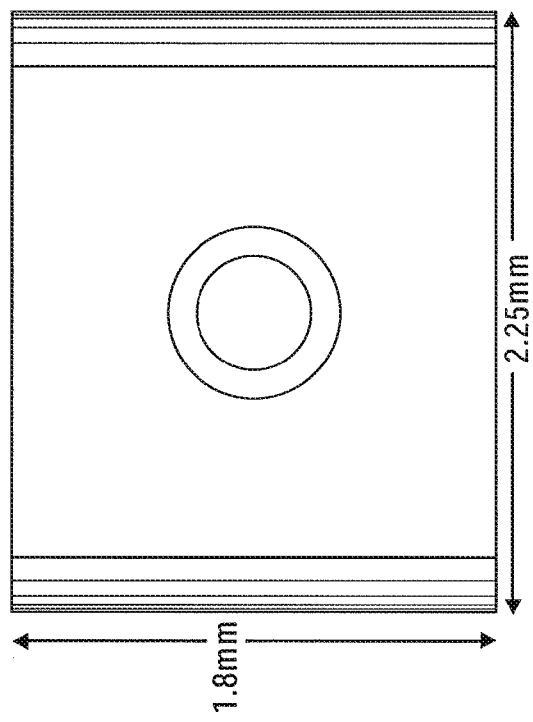

Other variations of shuttles are shown in FIGS. 12A-12C. In these examples the shuttle is roughly rectangular ("box" shaped) having at least one partially open side. This open side may help the shuttle to flex open/closed so that it can reliably secure over the distal end region of the suture passer. In some variations the dimple has been replaced with a tab or protrusion 1205. For example in FIG. 12B the protrusion has been replaced with a tab 1205'. In some variations this tab may be frangible; for example, the tab may be stripped off or deformed when removing the shuttle from the tissue penetrator after transferring it back and forth through the tissue. Other exemplary shuttles are shown in FIGS. 13A-13F. As mentioned, the shuttles may be formed of any appropriate biocompatible material, including shape memory materials such as nickel titanium, stainless steel, etc.

Figures 15A, 15B:
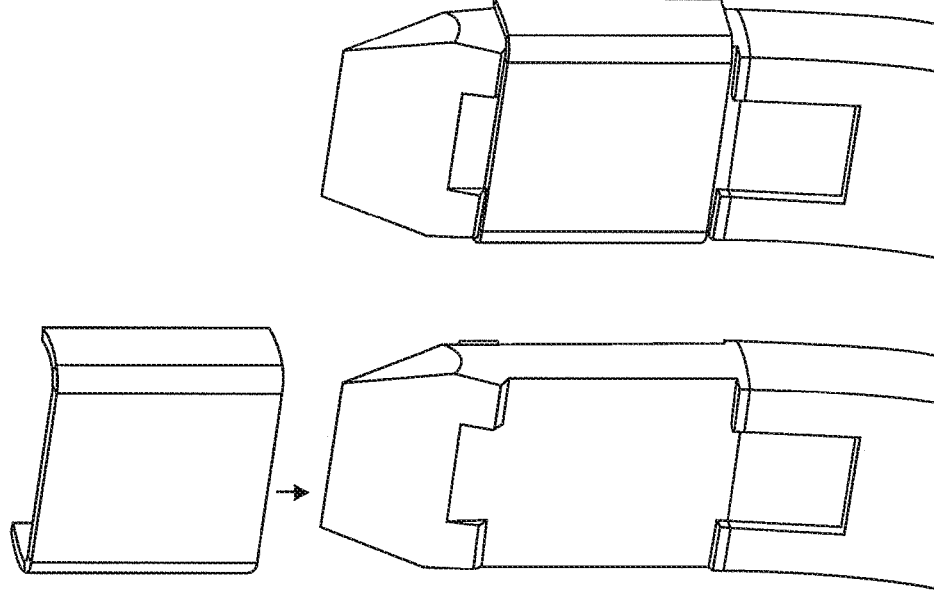
FIGS. 15A and 15B illustrate attachment of the suture shuttle variation shown in FIGS. 14A and 14B to a variation of the tissue penetrator similar to that shown in FIG. 11F.
Figure 14A:
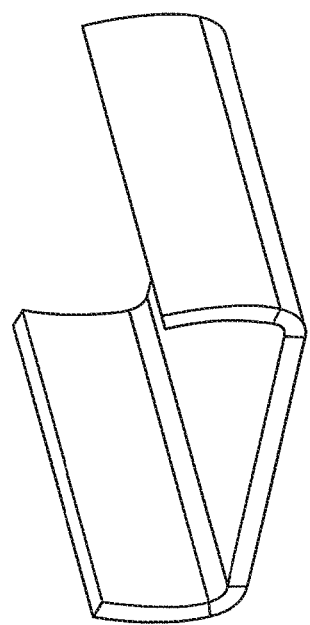
FIGS. 14A and 14 B shows perspective and side views, respectively of another variation of a suture shuttle.
Figure 14B:
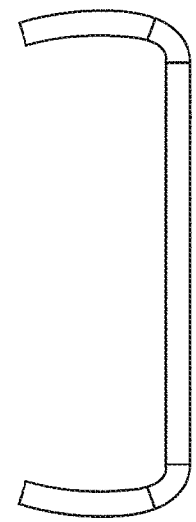
Figure 16C:
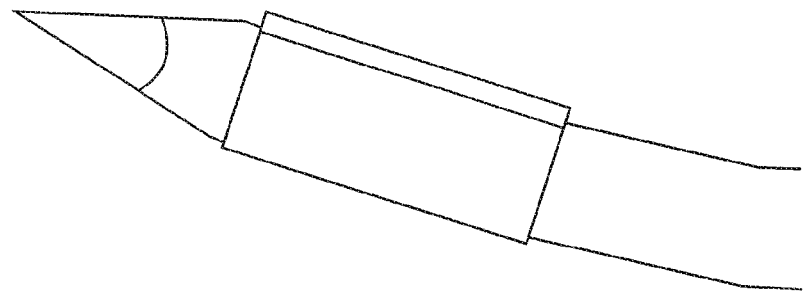
FIGS. 16A-16C illustrate attachment of the suture shuttle variation shown in FIGS. 14A and 14B to another variation of the tissue penetrator similar having a recessed region to retain the suture shuttle.
Figure 16B:
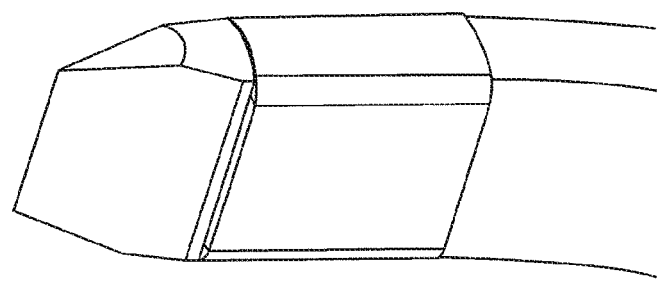
Figure 16A:
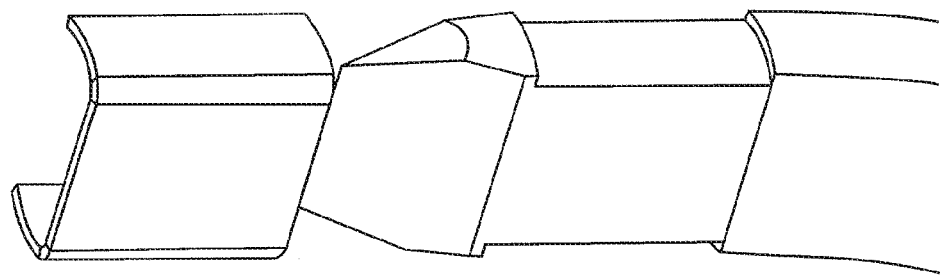

FIGS. 14A-14B show another variation of shuttle, and FIGS. 15A and 15B illustrate the coupling of the shuttle with the distal end of a tissue penetrator. FIGS. 16A to 16C also illustrate coupling of a shuttle with the distal end of a tissue penetrator. In general, any of the tissue penetrator configurations described herein may be used with any of the shuttle configurations described herein, although some combinations may be more optimally matched for coupling and/or uncoupling.

Double Pass Suture Passers

Some variations of the suture passers described herein are configured to form a stitch extending from a first side of a tissue to the opposite side of the tissue and back to the first side again; in some variations the devices are limited to passing twice and thereafter must be re-loaded to pass the suture again. Such variations may be referred to double pass suture passers, because they are configured to pass a suturing element (e.g., suture shuttle, suture, and/or pull wire for pulling a suture) back and then forth through the tissue.

One variation of a meniscus device configured as a double pass suture device includes two docks on one of the two arms of the device. For example, FIGS. 17A and 17B illustrate a portion of suture passing configured to pass two stitches through a meniscus. In FIG. 17A, the upper arm, which extends at an acute angle from the elongate body of the device, includes two dock regions. The distal most dock is a retaining dock (release dock) that is configured to hold a suturing element (e.g., shuttle) until the tissue penetrator extending from the lower arm engages the suturing element and releases it from the release dock. This is illustrated in FIG. 17A. In FIG. 17A, the upper and lower arm are both extended distally forming an acute-angled opening which can be placed over or around the tapered side of a meniscus. This configuration may be referred to as the first deployed position, and the first stitch may be pulled from this configuration.

In FIG. 17A, the tissue penetrator 1704 is shown extending in a curved path from the first (lower) arm to the second (upper) arm to engage the distal most dock 1707. Retracting the tissue penetrator 1704 back into the first arm and thereby drawing the suture shuttle (and any associated suture and/or pull wire) through the tissue from the superior side of the meniscus to the inferior side of the meniscus forms the first pass or stitch through the tissue. If desired, the device may then be repositioned (e.g., moved longitudinally or circumferentially along the meniscus if a longitudinal/circumferential stitch is to be performed), or it may be left in place to form a lateral loop or stitch. If the suture passer remains in the tissue on the meniscus, then the lower arm may be moved proximally relative to the upper arm to align the tissue penetrator with the second dock for passing the second stitch. This second configuration may be referred to as the second device configuration (or the second stitch configuration). As described in greater detail below, the suture passer device may include manual or automatic indexing to adjust the relative positions of the first and second arms whereby the tissue penetrator extending from the first arm is aligned with the first and second docks on the opposite arm.

In FIG. 17B, the first and second arm still form an acute-angled and distal facing opening which may surround the meniscus, however the lower arm is located more proximally than in FIG. 17A. Extending the tissue penetrator from the first (lower) arm to engage the second (upper) arm and transfer the suturing element (e.g., suture shuttle) from the tissue penetrator into the dock, which may be referred to as a retaining dock or holding dock. Both the docks in FIGS. 17A and 17B may include a retention mechanism (e.g., retaining pin, etc.) 1707 for holding the suture shuttle in position.

In the example shown in FIGS. 17A and 17B, the shuttle is preloaded in the distal most dock, and can be engaged by the tissue penetrator when the device is in the $1^{st}$ stitch position. A retaining clip inside the tip of the slider holds the shuttle in place. As mentioned, in this variation, the preformed needle picks up the shuttle from the first dock while in the $1^{st}$ stitch position, and pulls it back into the main body tip. The slider can then be retracted by the spring loaded plunger (see FIG. 7, for an example), allowing the slider (upper arm) to be retracted to the $2^{nd}$ position from which the needle can drop off the shuttle into the second dock when the device is in the second stitch position. In this variation there is a stripping mechanism such as a clip in the second dock that strips the shuttle off of the needle as it is retracted back into the main body.

FIG. 18 shows an enlarged view of a first or release dock. In this example, a machined block 1809 holds a clip 1805 in place. In this example, a suture shuttle 1811 is shown held within the dock, while a tissue penetrator 1813 is shown engaging the shuttle to remove it from the dock. In this example, the block 1809 provides a stop features that acts as a hard stop for shuttle, preventing it from overshooting. A pair of flanges or rims extending from the opening of the dock to help guide the needle into position to receive the shuttle. For example, in FIG. 18, a sheet metal clip 1805 squeezes the shuttle to hold it in place, but doesn't have any positive retention features; in some variations (e.g., see FIGS. 25A-26C) positive and releasable retention mechanisms are included and used to retain the shuttle.

FIG. 19 is an enlarged view of the second seat or dock within the upper arm. This dock is configured as a holding dock because it receives the shuttle from the tissue penetrator but does not readily release the suture shuttle back on the tissue penetrator. As in FIG. 18, the dock in this example also includes a machined block 1903 to hold the elements of the dock in position. In this example, a sheet metal clip surrounding the dock allows for needle insertion, but is also configured to strip-off the shuttle from the tissue penetrator upon needle retraction.

Figure 21B:
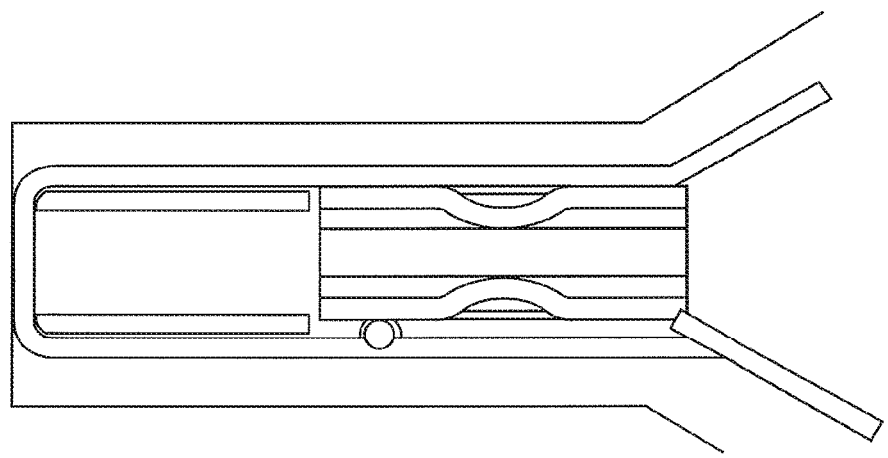
FIGS. 21A and 21B show side perspective and side views, respectively, of another variation of a dock region configured to accommodate a pull wire including a rim region forming a clip to help releasably retain a shuttle and pull wire.
Figure 21A:
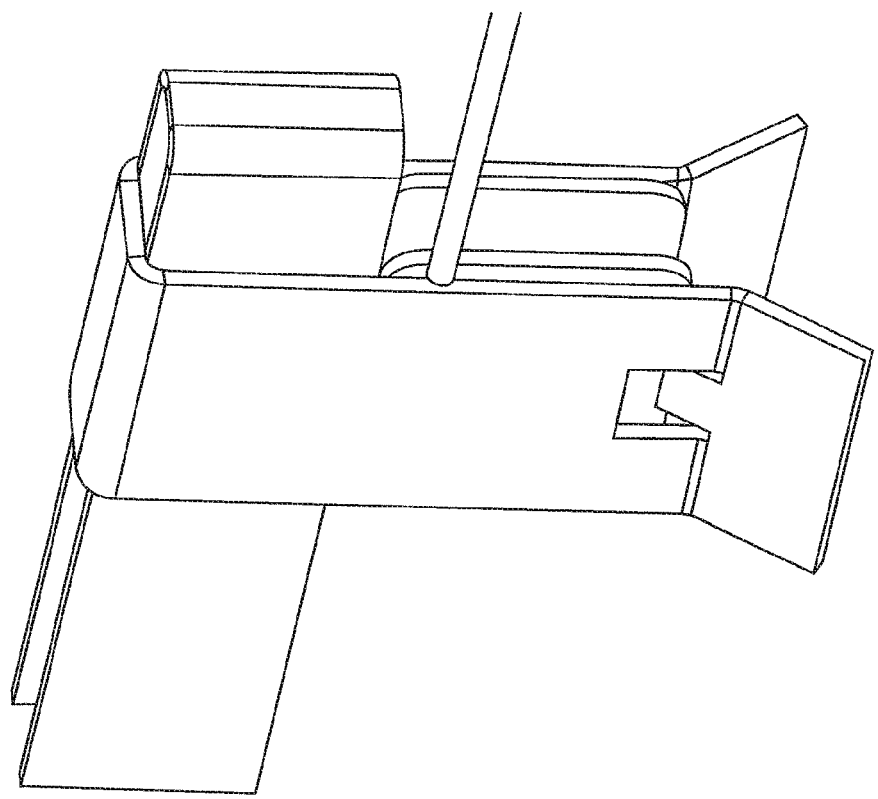

FIGS. 20A and 20A illustrate other variations of configurations for docks which may be used. For example in FIGS. 20A and 20B the dock includes an internal clip 2001 into which the shuttle is held. The dock also include a machined block 2002 that acts as a stop. In the variation shown in FIG. 20A, a bump on one side of clip holds the shuttle in a known location within the dock, and may "hold" the shuttle within the dock less securely than when the shuttle is engaged by the needle, which may have two such bumps for mating with the shuttle more securely, allowing it to be withdrawn. The asymmetric positioning of the shuttle 2005 within the dock may also allow room for an attached pull wire 2003 extending from the side of the suture shuttle. FIGS. 21A and 21B show another variation of a shuttle dock. In this version, the shuttle dock includes a ledge on the clip that provides a stronger hold than the variation shown in FIGS. 20A and 20b.

Figure 22:
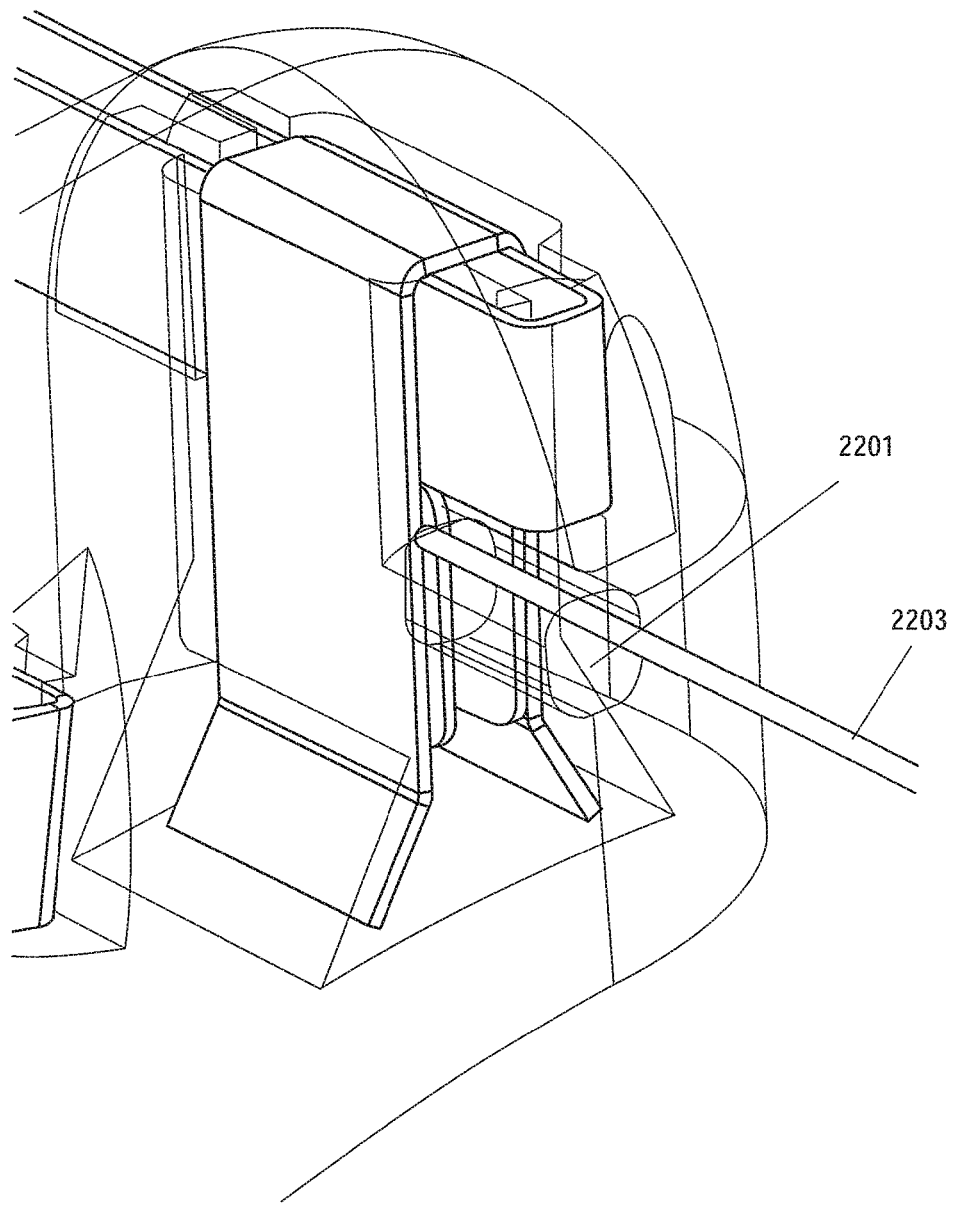
FIG. 22 is another variation of a suture device arm having a dock (e.g., release dock) for holding a pre-loaded shuttle and pull wire. In this variation the arm includes a hole or passage through which the pull wire may be drawn when the shuttle (with attached pull wire) is withdrawn across the space between the two arms of the device by the tissue penetrator.

As described in greater detail below, in some variations the suturing element includes a pull wire or zip wire that is configured to be drawn through the tissue prior to pulling a suture through the tissue. In some variations the pull wire may be managed by one or more structures on the device. For example, in FIG. 22 the device includes a channel or passage 2201 on the upper arm for the pull wire 2203. In this variation, pulling on lead wire will not dislodge shuttle. Thus, this variation is generally very secure when inserting the preloaded device into knee. The surgeon may even yank on lead wire to ensure shuttle is in the proper location for passing.

Figure 23:
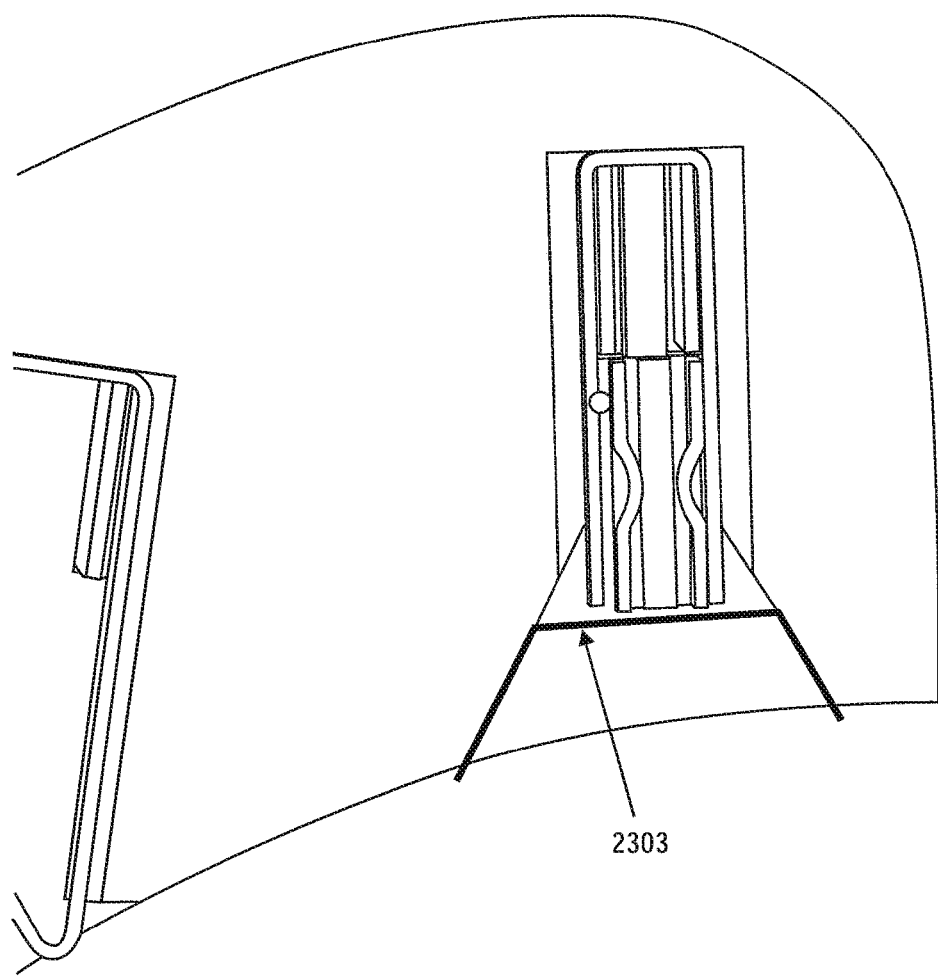
FIG. 23 shows another variation of a dock (e.g., a release dock) for holding a pre-loaded suture shuttle (and/or pull wire). In this variation the release dock is covered by a frangible covering (e.g., bioabsorbable plastic film) through which the tissue penetrator may extend.

FIGS. 23 and 24A-24b illustrate alternate variations of shuttle docks for hold a shuttle and releasing it onto a tissue penetrator. For example, in FIG. 23, the shuttle dock is a retaining dock which is sealed off by a frangible covering (typically made of a biocompatible and/or bioabsorbable material). The tissue penetrator may extend through the covering to engage with the shuttle. In this variation, the shuttle typically cannot fall out of the dock. Further, the device may be configured as single-use, since the shuttle may not be reloadable, making it difficult to reuse the device. As mentioned, the covering film can be made of bioabsorbable material so that any left-over pieces in the knee don't cause issues. In the example shown in FIG. 23, the thin plastic film shown covering the shuttle within the dock is bonded to lead-in on pocket; a needle may be used to pierce the covering film to retrieve shuttle.

In FIG. 24A, the dock includes an elastomeric body (e.g., rubber, silicone, etc.) 2403 into which the shuttle is held. In general, rubber holds the shuttle securely. The elastomeric body allows the dock to flex to receive the shuttle (and tissue penetrator), while retaining the shuttle. In this variation the dock also includes a lead-in region 2407 to guide the needle into the dock and a stop feature 2405 to stop the needle from extending beyond the region where the shuttle may be docked and undocked. FIG. 24B shows an enlarged perspective view of the elastomeric body 2403 surrounding the dock. In this example, the body includes a channel 2409 for management of a lead wire.

Figure 25A:
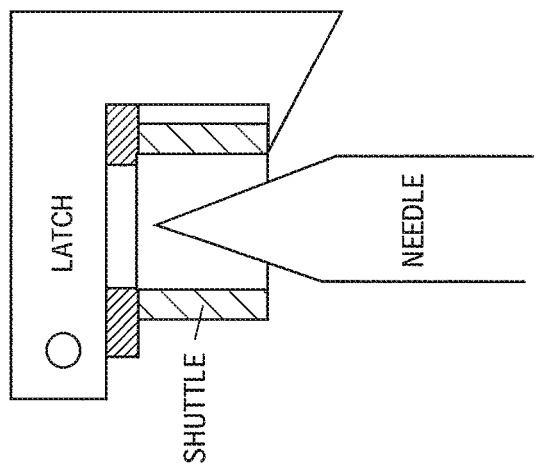
FIGS. 25A-25C illustrate another variation of a dock for releasably securing a suture shuttle within an arm of the suture passer. In this variation, the dock comprises a spring-loaded latch.
Figure 25B:
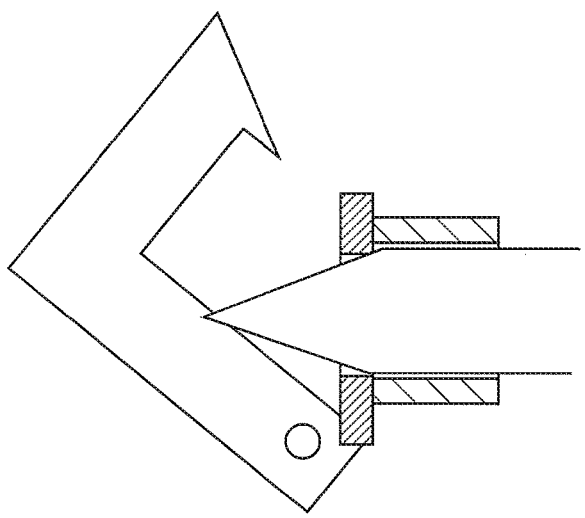
Figure 25C:
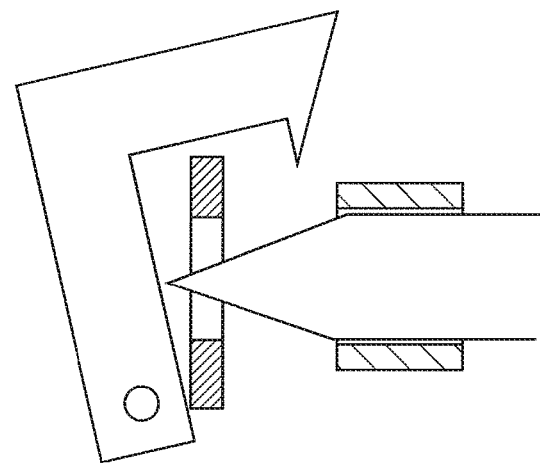

FIGS. 25A to 25C illustrate another variation of a release dock. In this variation the dock includes a spring loaded latch that is triggered by contact with the tip of the tissue penetrator (needle) to release the shuttle onto the tissue penetrator. In FIG. 25A, the spring loaded latch holds the shuttle in position, as shown. In FIG. 25B, a tissue penetrator inserted into the dock contacts the latch and forces it up, releasing the latch from holding the shuttle, so that (in FIG. 25C) the tissue penetrator can be withdrawn, pulling the shuttle with it.

Figure 26A:
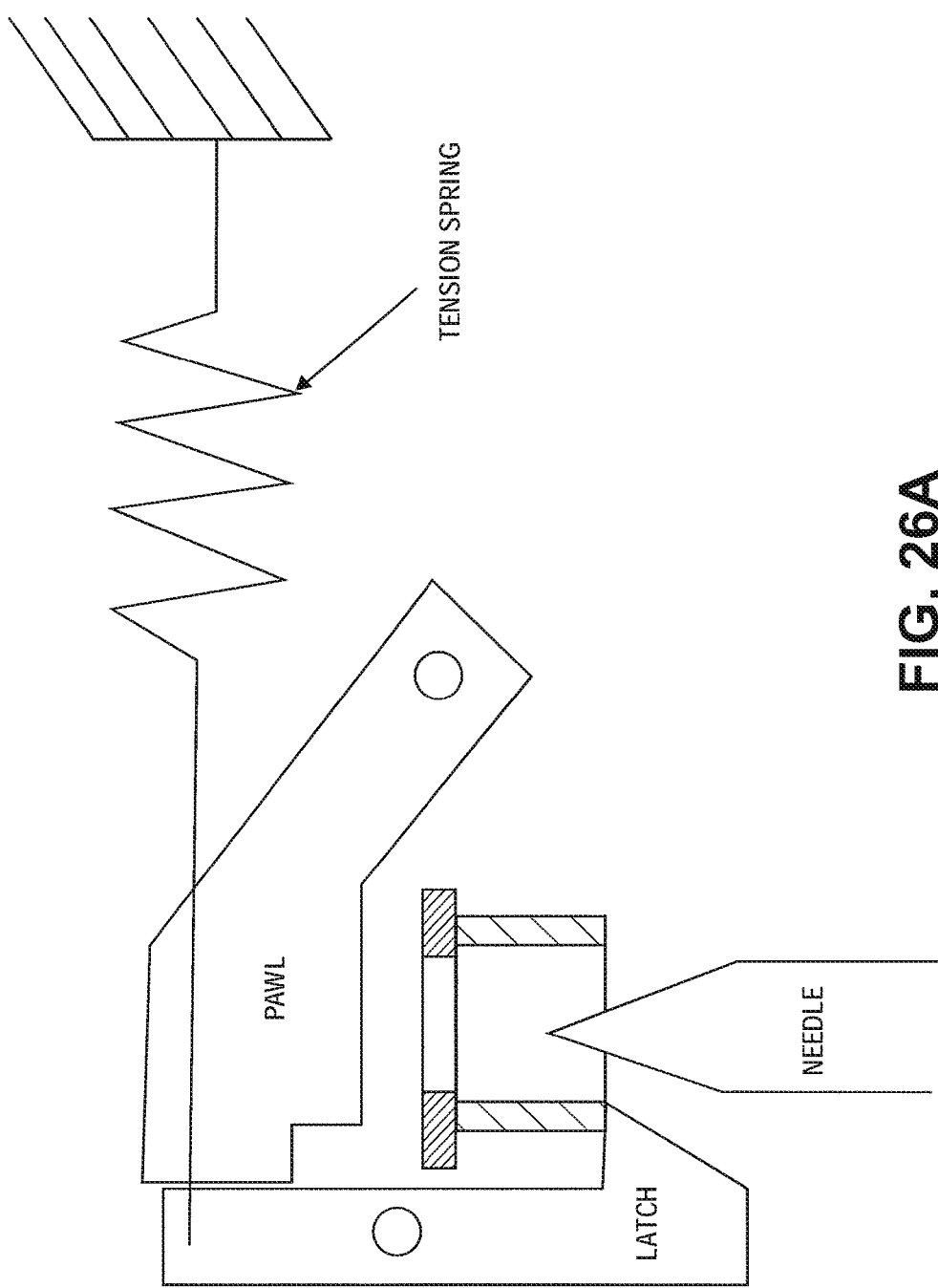
Figure 26B:
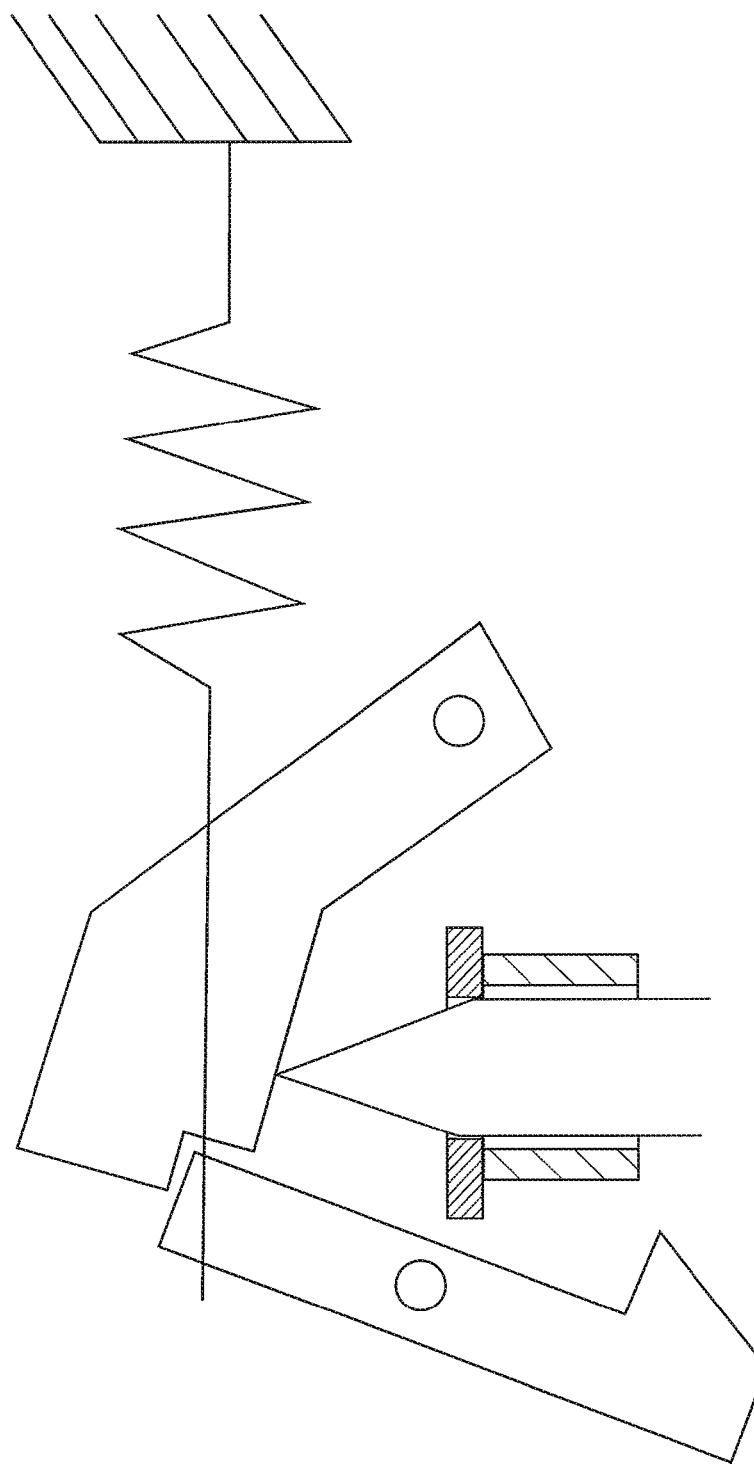

A similar variation is shown in FIGS. 26A-26C, which illustrates the operation of a tension spring loaded latch mechanism including a pawl. In FIG. 26A the latch holds the shuttle within the dock, while the tension spring loads the latch against the pawl. The tissue penetrator (needle) may insert into the dock and push the pawl out of the way, as shown in FIG. 26B, allowing the latch to rotate. The tissue penetrator may then capture the shuttle and be withdrawn from the dock, as shown in FIG. 26C. In this example the latch and pawl are held out of the way by the spring, so that they don't interfere with the removal of the needle and shuttle.

Zip/Pull Wire

In any of the variations described herein, a pull wire may be used to suture the tissue. The pull wire may also be referred to as a zip wire, a pull loop, a leash, a lead, a tether, or the like. In general, the pull wire is typically a thin, flexible wire-like element that may be drawn through the tissue by the suture passer in a suture pattern. In some variations the distal end of a pull wire may be pulled through the tissue before the suture is pulled through the tissue, and in some variations, even before the suture is attached to the pull wire. After the pullwire has been passed, one or more sutures may be coupled to the proximal end of the pull wire and the pull wire may be drawn through the tissue to pull the suture into place; the pull wire may be subsequently removed from the tissue.

For example, the pull wire used may be a small diameter wire/cable. The smaller diameter wire will take much less force that a larger diameter suture to be stitched and may exert minimal forces on the shuttle. Once the wire has been stitched through the tissue (e.g, from a first position to a second position relative to the tissue), the device can be removed and the wire pulled through the tissue; a loop on the proximal end of the wire may hold a suture. For example, a suture may be threaded through the loop at the proximal end of the pull wire. As the pull wire is drawn out of the tissue, the suture is pulled through the channel left by the pull wire. The suture can then subsequently be tied off with various knot tying methods.

In some variations, the pull wire is made from stainless steel cable (e.g., 19 strands wound together as 1). This configuration may allow a great deal of flexibility and may also allow the pull wire to be welded to a stainless steel shuttle. In some variations the pull wire is made from a single wire or several other cable configurations. It can also be made of any other appropriate material, such as nickel titanium (e.g., Nitinol), elgiloy, polymeric materials, etc.

Figure 27:
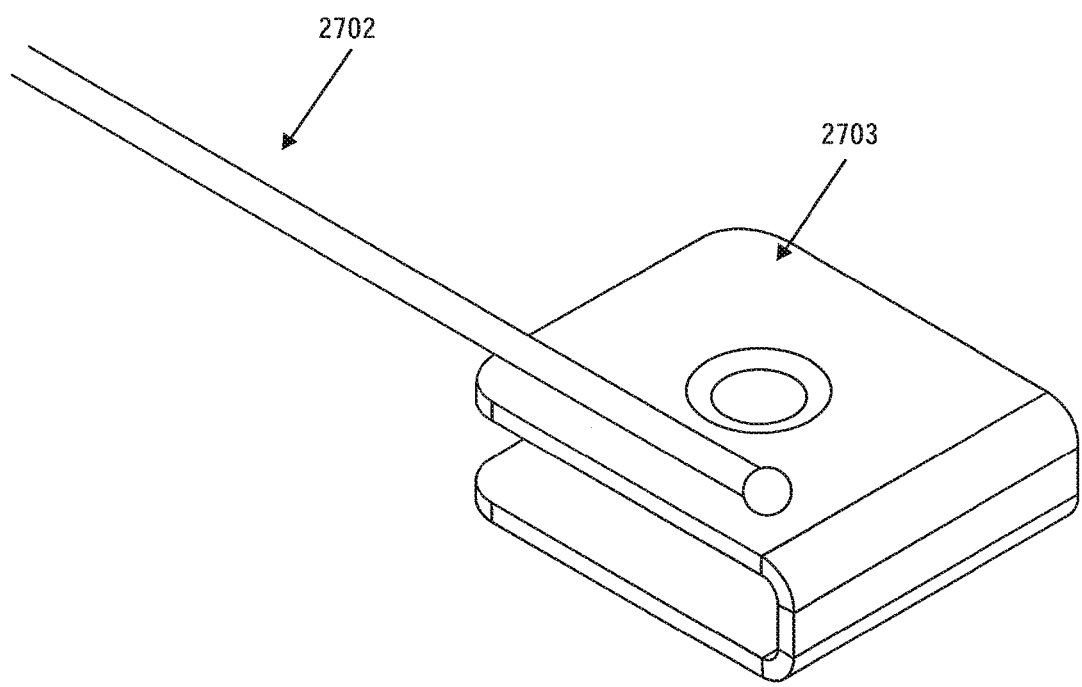
FIG. 27 is another variation of a suture shuttle including a pull wire

FIG. 27 illustrates one variation of the distal end of a pull wire 2702 that has been attached to a suture shuttle, as described above. In this example, the pull wire 2702 has been welded to a shuttle 2703. Another example of a pull wire is shown in FIG. 28, including exemplary dimensions. In FIG. 28, the pull wire 2801 is coupled to a shuttle 2803 at its distal end and extends for some length (e.g., approximately 10 inches, though shorter or longer wires may also be used). The proximal end of the pull wire forms a loop 2805 through which a suture 2807 may be threaded either before or after the shuttle and pull wire have been passed through the tissue. The proximal end of the pull wire in this example is looped onto itself and held by heat shrink tubing 2811; any appropriate method of forming a loop or suture attachment site (including non-loop attachment sites, such as clips, clamps, adhesives, splicing, etc.) may be used.

In some variations, the pull wire can also be coated (i.e., with PTFE) to prevent tissue damage as it is pulled through tissue.

FIGS. 29A and 29B illustrate another variation of pull wires as described herein. In FIG. 29A the pull wire forms a loop; in this example, the loop may be biased to open as shown, making it easy to load a suture on the pull wire after or before it has been passed through the tissue. This may be particularly beneficial when loading the pull wire with the suture from within the tissue (e.g., within the knee), for example, arthroscopically. In FIG. 29B, the pull wire includes a smaller loop region. In both of these examples, the pull wire is shown attached to a suture shuttle.

The devices and systems described herein may be adapted for use with a pull wire. For example the device may include structures to manage or control the pull wire. As discussed in reference to FIG. 22, for example, the seat/dock may be adapted to allow a pull wire to extend out of the seat. FIG. 30A shows another variation of an upper arm of a suture passer including a pair of docks for receiving a suturing element which may include a pull wire. In FIG. 30A, the upper arm includes a cut-out channel 3003 in the lateral side of the arm to allow a pull wire to extend from the upper arm. Similarly, the opposite arm, from which a tissue penetrator extends and retracts, may be adapted to allow the lead wire to extend from the device without interfering with the activity of the suture passer. FIG. 30B shows an enlarged view of a portion of the lower arm including a tissue penetrator 3004 retracted into the lower arm 3006. The tissue penetrator includes a suture shuttle coupled to a pull wire 3012, and the pull wire extends from a channel 3008 in the lower arm.

Articulating Shaft

In some variations the shaft of the suture passer may be articulating which may allow the device to reach different regions of the meniscus. The articulating shaft may be configured to bend or flex (articulate) at a predetermined position along the length of the device, to a predetermined degree/angle or range of angles (e.g., between 1 and 90 degrees, between 5 and 45 degrees, between 10 and 30 degrees, 45 degrees, 30 degrees, etc.), and in a predetermined direction or directions (e.g., "up/down," radially in the direction of the upper arm; side to side, etc.).

For example, the elongate shaft shown in FIG. 7A may include on or more bendable, jointed or the like. In some variations the elongate shaft is relatively stiff until actuated to bend; this may allow the device to be positioned more precisely, even while the distal end of the device (which may form a distal-facing opening) is positioned around the meniscus.

Figure 39A:
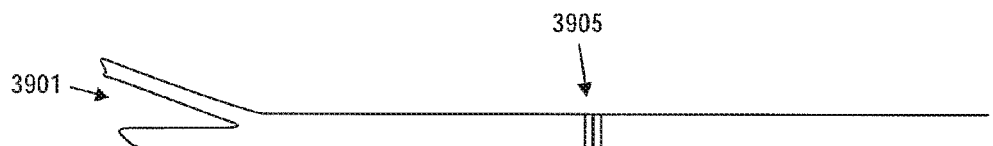
FIGS. 39A-39D show a variation of a meniscus suture passer having articulating shafts.
Figure 39B:
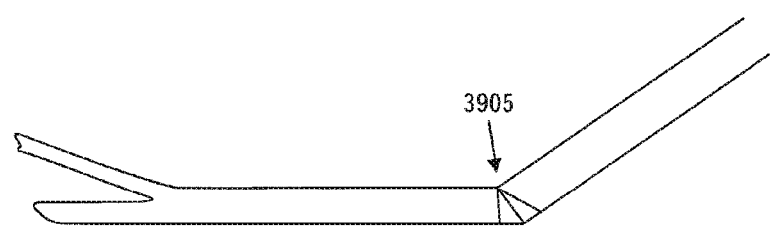

As mentioned, the elongate body may be configured for articulation in any appropriate direction, or multiple axes of direction. For example, FIGS. 39A-39B and FIGS. 39C-39D illustrate two variations of meniscus suture passers having articulating elongate shafts. FIG. 39A shows a side view of a meniscus suture passer including a distal region including the first and second arms 3901 wherein the upper arm is a slider that may slide proximally and distally. This variation includes a hinged or articulating joint region 3905 which may be bent by the user (e.g., by activating a control on the handle region, not shown) to bend the device up/down (e.g., where up is in the direction of the slidable upper arm, and down is in the direction of the straight lower arm). This is illustrated in FIG. 39B.

Figure 39C:
Figure 39D:
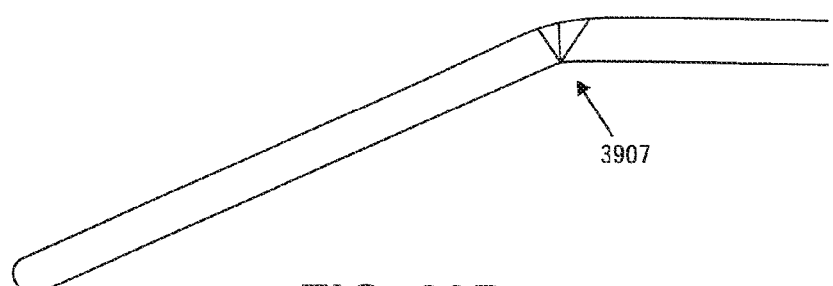

FIG. 39C shows another variation of a suture passer having a hinged or articulating joint region 3907. FIG. 39 shows a bottom view of the device. In this variation the device may be articulated left or right (e.g., side-to-side), as shown in FIG. 39D.

The location of the joint or articulating region may be more proximal or more distal. In some variations, the articulating region is lockable in either the straight (unbent) or the articulated (bent) configuration. For example, in some variations only the distal end region (just proximal to the region forming the distal-facing opening) is configured to articulate. The shaft and/or the arms, including any slider region or arm, may be configured to articulate. For example, the upper arm or slider may be configured to articulate with a hinge region, while the lower arm (extending from or continuous with the elongate body shaft) may be made bendable (e.g., may be formed of a bendable material, such as Nitinol, etc.) to follow a bend at a fixed position relative to the upper arm. In some variations this configuration is reversed. The device may be configured to bend either before, during, or after the distal-facing opening has been formed between the upper and lower arms by extending (or retracting) one or both arms, as described above, and illustrated in FIG. 17A. Thus, in some variations, the device may be configured to bend in the sideways direction (e.g., FIG. 39D) or articulate only when the distal-facing opening is formed between the upper and lower arms 3901.

In operation, bending or articulation of the device may allow it to enter the inner region of the knee joint (the region between the two menisci) from an anterior approach, and be articulated or bent at an angle to treat even regions of the lateral or medial meniscus that are located towards the anterior of the knee. In the variation so the meniscus treatment devices described herein, the device may be manipulated within the knee joint to suture a meniscus without penetrating the capsule or more capsular end of the meniscus, thereby avoiding the more highly vascular region, preventing further injury.

Imaging

In general, the meniscus treatment devices described herein may be used with imaging (e.g., arthroscopic imaging). In some variations, the devices described herein may be adapted to include on-board imaging or one or more channels for imaging. For example, the suture passer illustrated in FIG. 7 may include an imaging sensor at or near the distal end for imaging the tissue as the device is positioned and/or operated. In one variation the device includes an imaging modality (e.g., fiber optic, optical bundle, CMOS, CCD, etc.) sensor located to visualize in the distal-facing direction. The imaging may include a sensor (or channel for a sensor that is positioned on the upper or lower arm to face distally. In some variations the sensor is located just proximal to the bend in the upper arm. Imaging information may be fed back through the body of the device, or transmitted from the tip wirelessly, and be presented to the physician, stored, or otherwise processed.

Indexing

Operation of a meniscus suture passer typically includes moving the upper arm and/or lower arm relative to each other in order to coordinate passing a suturing element between the upper and lower arms by engaging a tissue penetrator and two or more seats or docks. Before passing a suturing element between the upper and lower jaws, the tissue passer be set into a delivery configuration for insertion into the knee and around the meniscus. Thus, one arm (e.g., the bent or angled arm, referred to as the slider in FIG. 7) may be extended fully distally (or the lower arm retracted proximally) so that the lower arm is proximal to upper arm, as shown in FIG. 7. This configuration has a narrow (though slightly bent) diameter, and may make insertion of the device into the knee region easier. Once in position, the upper and/or lower arm may be positioned so that the tissue penetrator crossing between the two arms will engage and transfer the suturing element.

The tissue penetrator typically moves along a predetermined pathway between the upper and lower jaws, and moving either (or both) the upper and lower jaw may determine which of the two or more docks engages with the suture passer. For example, when passing a suturing element to form a first stitch from the superior side of a meniscus to the inferior side of the meniscus, the first and second arms should be in a first stitch configuration, wherein the upper, bent, arm and the lower, straight, arm are both extended distally so that the tissue penetrator can cross through the gap between the arms, including any meniscus tissue between the arms, and engage with a suturing element in the first dock. This may be achieved in some variations of the device by including indexing tabs, marks, detents, locks, stops, or the like, which indicate the correct relative positions of the upper and lower arms in order for the tissue penetrator to mate with the appropriate dock and engage with the suturing element (e.g., shuttle, pull wire, and/or suture).

In some variations, the relative positioning of the first arm and the second arm to form the first and second stitches through the tissue may need to be somewhat precise. Thus, positive indexing features may be built into the suture passer to accurately locate the slider position (upper arm) relative to the needle/shuttle (the lower arm).

Similarly, when passing the second stitch from the inferior side of the meniscus to the superior side of the meniscus, the lower arm may be slightly retracted proximally, relative to the upper (bent) arm, allowing the tissue penetrator to extend towards the second dock into which the shuttle may be released.

Figure 31A:
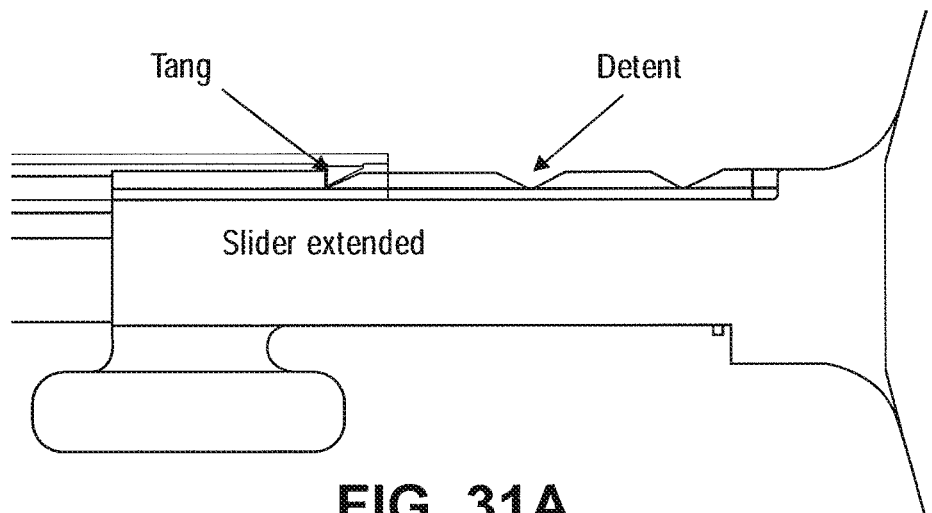
FIGS. 31A-31C illustrate indexing features of one variation of a device which allow distal/proximal extension and retraction of an arm of the suture passer to predetermined functional positions for insertion/placement of the device (FIG. 31A), positioning around the meniscus and passing the first stitch (FIG. 31B), and adjusting the positions on the meniscus and passing the second stitch (FIG. 31C). In this variation the indexing features are detents on the body or one arm of the device that interface with tangs on the other arm of the device.
Figure 31B:
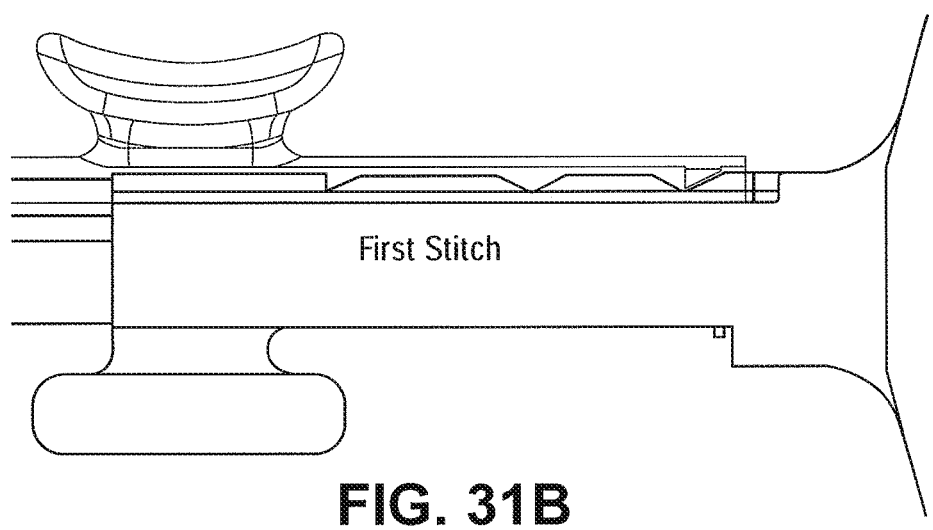
Figure 31C:
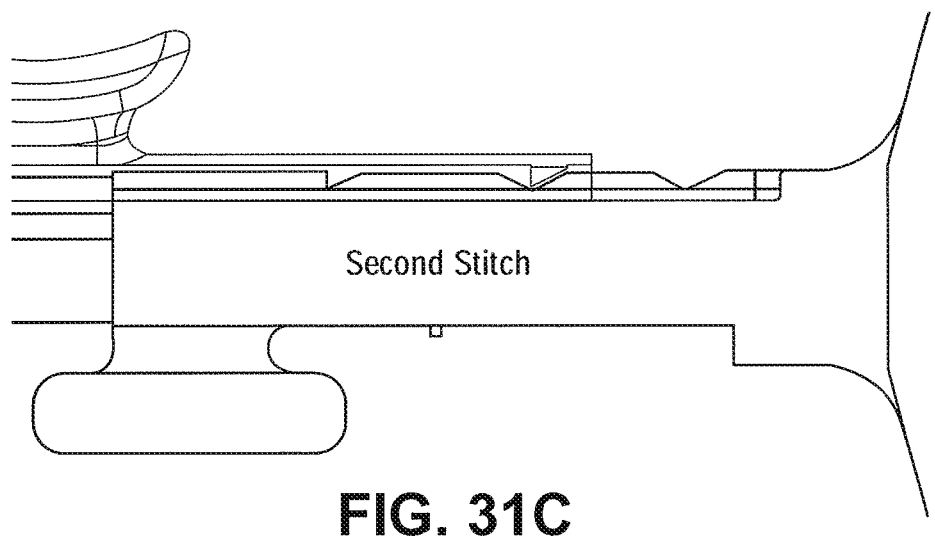

FIGS. 31A to 31C illustrate one example of a suture passer adapted to include stops or detents indicating the different relative slider configurations. In this variation, the upper arm (slider) includes one or more tangs that mate with a detent on the lower arm and/or elongate body of the device. As the tang engages the detent, it holds the upper and lower arms in this configuration, which may also be marked or otherwise indicated on the device. In FIG. 31A the upper arm (slider) is fully extended distally, so the device is in the delivery configuration (e.g., see FIG. 7). In FIG. 31B, the device is in the "first stitch" configuration, with the slider fully retracted proximally so that a tissue penetrator from the lower arm can extend to engage a shuttle and/or lead wire in the upper arm (e.g., see FIG. 17A). FIG. 31C shows the "second stitch" configuration, in which the upper arm is in an intermediate configuration (e.g., see FIG. 17B).

In some variations the devices include markings on the slider (upper arm) and main body to indicate the functional position of the two arms.

The suturing devices described above may also be configured to automatically shift between these different configurations. For example, in some variations the suturing device may include a handle with a control that is operated by a single button, knob, switch, or the like that automatically converts the configuration from the delivery configuration, into the first stitch configuration (and/or passes the suturing element once in the configuration), the second stitch configuration, and a removal configuration.

In FIG. 7, the handle shown includes a grip region 701 and a plunger 709. The plunger may be functionally connected the tissue penetrator (e.g., including the rod as indicated in FIG. 8). The plunger may include a return (e.g., a mechanical return such as a spring, etc.) for returning the implant back to a start position so that the tissue penetrator is retracted back into the first arm. In some variations the implant may alternatively or additionally include an actuator (e.g., mechanical actuator, spring, etc.) for aiding in extending the tissue penetrator from the device and across the tissue.

The handle may be ergonomically designed. For example, other handle configurations can be employed to position the slider/main body and advance the needle.

Additional Tissue Penetrator/Shuttle Designs

FIGS. 32A to 35G illustrate additional tissue penetrator and corresponding shuttle configurations that may be used in suture passer devices including the meniscus suture passers described herein. For example, in FIGS. 32A and 32B, the tissue penetrator 3204 is configured as beveled cylindrical needle shape having a neck region 3206 proximal to the distal top of the needle. In this variation, the suture shuttle 3202 is a tubular shape including two or more tabs 3206 which can pull over the needle and snap into the neck region

Figure 34A:
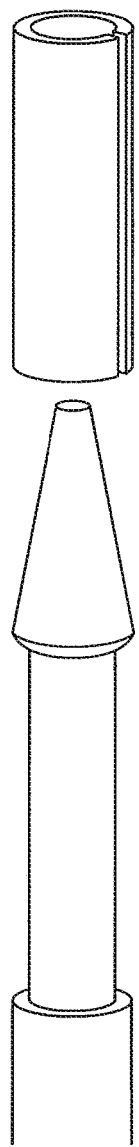
FIGS. 34A-34B illustrate another variation of tissue penetrator and shuttle, similar to that shown in FIGS. 32A-32B but with a split or gap in the hypotubular shuttle.
Figure 34B:

3206. In some variations, such as those shown in the variation of FIGS. 33A to 33C, the shuttle includes cut-out regions 3305, slots, slits or cuts which may enhance flexibility of the shuttle. This is also illustrated in FIGS. 34A-34B. Other examples of shuttles may have similar spring forms in various shapes and sizes, including rectangular and tubular shapes. Any of these examples may also include an attachment site for a suture and/or a pull wire or the like.

FIGS. 35A-35G illustrates another variation of a tissue penetrator 3507 and shuttle 3503 in which the two elements are keyed to retain and release the suture shuttle. For example, FIG. 35A-35G describes a shuttle and tissue penetrator combination that can pick up and drop off for multiple pass stitches without requiring force to be applied to retain or remove the shuttle from the tissue penetrator. For example, in FIG. 35A, the shuttle 3503 starts out in upper arm (e.g., in a release dock in the upper arm). The needle 3507 can extend from the lower jaw across to the upper jaw and the tabs on the shuttle align with profile path on the needle, as shown in FIG. 35B. In FIG. 35C, the needle finishes its stroke upwards, and the shuttle is forced by the profile path formed in the needle body to rotate. The needle is then retracted back down to the first arm, and drag forces push shuttle towards end of needle, as shown in FIG. 35D. The profile path in which the tabs of the shuttle reside allow the shuttle to be retained in the tissue penetrator. In FIG. 35E, the needle then goes back through tissue, forcing shuttle down the needle path as shown. As the needle retracts back to the first arm, the shuttle follows the path off the needle, as shown in FIG. 35F, until the needle fully retracts and the shuttle is retained by upper jaw, as shown in FIG. 35G.

Methods of Operation

In general, the devices described herein allow methods of suturing the tissue by passing from one side of the meniscus to the opposite side of the meniscus and back to the starting side from the "inside" of the knee by minimally invasively (e.g., arthroscopically) placing the suture passer around the meniscus. Such back-and-forth suturing may be performed without removing the suture passer from the tissue, including without removing the suture passer from off of the meniscus. For example, a suture may be passed from the upper outer surface (e.g., the concave, femur-facing superior side) of the meniscus, though the body of the meniscus to the lower outer surface (e.g., the flat, tibial-facing inferior surface) of the meniscus, and then back through the body of the meniscus from the bottom to the top. This allows both vertical and horizontal suture patterns to be formed using the same device.

Returning to FIG. 2, the terminology used to describe the anatomy of the meniscus is illustrated. In general, the meniscus is thicker peripherally and tapers centrally; the thicker, outer vascular capsular region 202 (which faces outward from the knee) is referred to herein as the capsular region of the meniscus; this zone may extend from the outer region inward to between 10% to 40% of the cross-section of the meniscus. This region may also be referred to as the vascular zone of the meniscus. The region lateral to the meniscus may be referred to as the meniscocapsular region 211. The tapered and more medial region 204 may be referred to as the apex of the meniscus (the inner region of the meniscus). The upper (superior) outer surface of the meniscus is typically concave and faces the femur, and therefore may be referred to as the femur-facing upper outer surface of the meniscus 206. Opposite the upper outer surface 206 is the generally flat lower (inferior) outer surface which faces the tibia, and may therefore be referred to as the tibial-facing lower outer surface of the meniscus 208.

In general, the suture passers described herein may be positioned minimally invasively within the knee so that that suture passer approaches the meniscus from the tapered side of the meniscus 210, opposite the vascular capsule of the meniscus. Thus, many of the methods described herein may be referred to as "inside" repairs, because they are performed minimally invasively from within the knee, approaching from the tapered (avascular) side 204 of the meniscus. For example, a camera and/or a suture passer device may be inserted into the knee through an incision made in the front (anterior) region of the knee, avoiding the medial, lateral and posterior aspects of the meniscus. Once within the knee, the devices and methods described herein allow a suturing element to be passed around and/or through the meniscus from within the knee to repair the meniscus without penetrating substantially into the meniscocapsular tissue (e.g., lateral to the meniscus), avoiding the neurovascular tissue feeding the meniscus. In some variations, the tissue penetrator of the suturing device passes through only a circumscribed portion of the meniscocapsular tissue (e.g., a region extending less than 5 mm out of the meniscus, less than 2 mm out of the meniscus, less than 1 mm, etc.). In general, the pathway through the meniscus may be arcuate because the tissue penetrator may be curved or arced. Thus, the tissue penetrator may extend from the superior to the inferior sides of the meniscus in an arcuate pathway which extends superficially through the meniscocapsular tissue.

FIGS. 6A-6M show one variation of a suture passer used to repair a torn meniscus. These figures illustrate the operation of the device to repair a peripheral vertical tear in a meniscus.

For example, FIG. 6A shows a sagittal cross-section through a patient's knee. A portion of the meniscus is shown. The vertical tear 101 (shown as a line) in the peripheral region of the meniscus 100 is illustrated. The femur is shown above the tibia, with the torn edge of the meniscus between the two. One representation of a continuous suture passer 103 (similar to those described above) is shown to the right of the cross-section through the knee. The suture passer may be inserted into the joint via a minimally invasive (e.g., arthroscopic) procedure, an open surgical procedure, or a semi-open surgical procedure. For example, in some variations the torn meniscus may be accessed and visualized arthroscopically; the suture passer may be inserted through a separate incision or through the same incision; in some variations the suture passer is inserted through a cannula.

In this example, the suture passer is inserted in a collapsed or retracted configuration, in which the first arm 105 is retracted proximally (e.g., towards a handle or control at the proximal end). The second arm 102 extends from the distal end (and may be fixed in this extended position, or it may be adjustable or extendable). The second arm 102 shown in this configuration is curved ('upwards') so that it can be inserted around the torn meniscus, as shown in FIGS. 6B-6C. The entire suture passer is sized for use in this space. For example, the suture passer may have a diameter in the un-extended/delivery configuration that is less than a typical (or size-appropriate) space between the femur and tibia, i.e., less than about 10 mm, less than about 9 mm, less than about 8 mm, less than about 7 mm, less than about 6 mm, etc. This diameter may include the diameter of the first arm, which may have an individual diameter of less than about 5 mm, less than about 4 mm, less than about 3 mm, less than about 2 mm, etc.

Figure 6D:
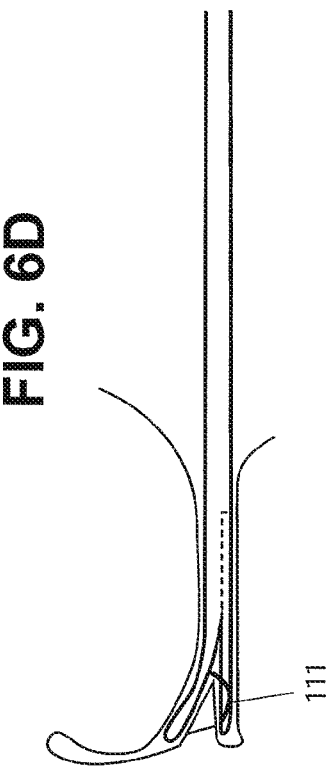

The distal end of the suture passer, formed by the distal end region of the second arm, may thus be extended into the tissue and above the torn meniscus, as illustrated in FIGS. 6A-6C. Once the second (upper) arm is positioned, the first (lower) arm 105 may be extended from the device, as illustrated in FIG. 6D. In this example, the first arm is extended from the proximal region of the device, so that it may extend under the meniscus, opposite from the second arm. The first arm may be straight (as shown in FIGS. 6A-6K), or it may be curved or bendable.

In the illustrated method of FIGS. 6A-6K, the first, lower, arm is extendable axially from the body of the device. The lower arm extends forward by sliding underneath the inferior surface of the meniscus and towards the capsule of the underside of the meniscus. The lower arm may be extended to the most distal "stop." The distal stop may be indicated by a resistance (e.g. a physical stop), and may be locking. For example, the second arm may click into position when held in a stop on the suture passer. A handle or control on the device may be used to disengage and withdraw the device.

Figure 6E:
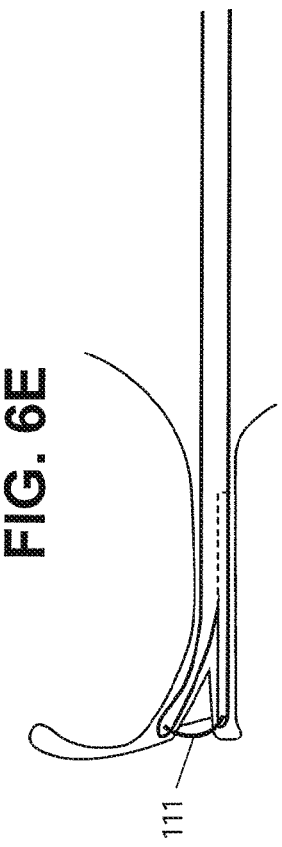
FIGS. 6E-6H illustrate passing the suture through the meniscus multiple times using the suture passer as described herein.

Once the first arm is in the desired axial position (e.g., fully extended or otherwise) relative to the first arm, the suture may be passed. For example, FIG. 6E illustrates the initial step of extending the tissue penetrating element (needle) 111 from within the first arm and across the space separating the first and second arms. In this variation, the tissue penetrating element is a curved needle that is pushed from the distal end region of the device as illustrated to pass through the meniscus as shown. As mentioned above, the tissue penetrator may be configured to bend upon exiting the device, and may be pre-bent.

Figure 6F:
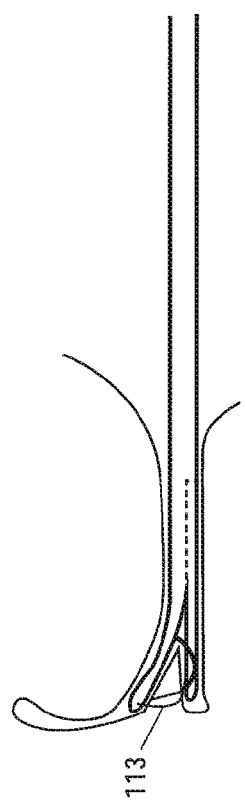

Initially, the tissue penetrating member forms a pathway through the tissue; the suturing element (e.g., a shuttle, pull wire and/or suture) may be held within the second arm. In this example, the needle penetrates through the meniscus (and in some variations, the peripheral meniscocapsular tissue) and mates with a complementary region of the second arm, such as a first distal seat (i.e., shuttle seat or suturing element seat). The suturing element is initially pre-loaded into the distal seat. Contacting the seat with the tissue penetrating member when the suturing element is already held in the seat may cause the suturing element (e.g., shuttle) to snap, clamp, or otherwise secure onto the tissue penetrating member, and be released from the from the seat, as illustrated in FIG. 6E. Thereafter, the suturing element and any attached structure (e.g., pull wire, suture, etc.) 113 may be withdrawn back through the meniscus with the tissue penetrating member as it is retracted into the second arm, as illustrated in FIG. 6F. The suture is thereby drawn across and through the meniscus.

In some variations the device is configured so that the tissue penetrating element (e.g., needle, etc.) may be extended only when the lower arm is extended to a position from which the tissue penetrating element may mate with the receiving site (e.g., seat) on the opposite arm.

Figure 6G:
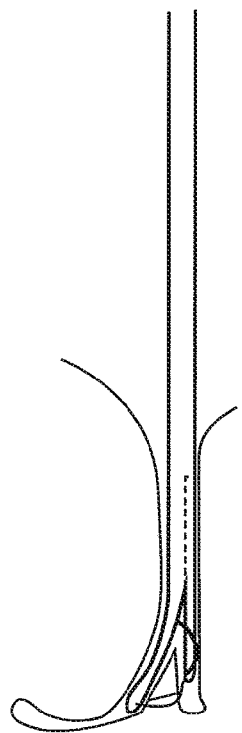
Figure 6H:
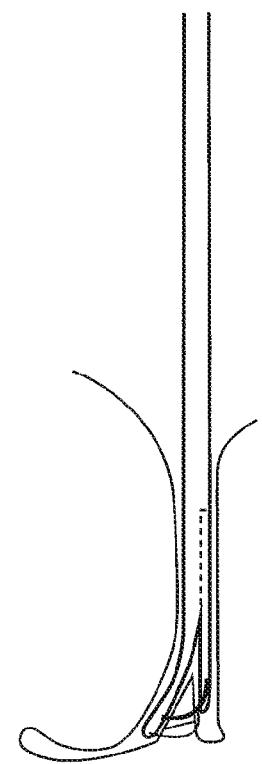

In FIG. 6G, the first (lower) arm 105 can then be retracted slightly. In any of these variations, the arms may be referred to as forming a "jaw" and thus the second arm may be referred to as the upper or second jaw and the first arm may be referred to as the first or lower jaw. In this example, the first arm is retracted into a stop position that is located proximal to the distal end. This second stop may be referred to as the intermediate or second stop position (the distal end position is the first or distal stop, and the fully retracted position may be referred to as the proximal stop position). The device may hold or releasably "lock" the first arm in this position so that the tissue penetrating member (to which the suturing element is now attached) may be extended back through the meniscus, in a region located more peripheral to the tear, as illustrated in FIGS. 6G and 6H. Meanwhile, the upper (second) arm is left securely in place. In some variation (e.g., anatomy permitting), the second arm may also be slightly withdrawn proximally, or the entire device may be moved laterally or proximally to position an additional stitch at a different position.

In some of the variations described herein, the lower arm (e.g., the arm including the tissue penetrating element) may be longitudinally extended/retracted relative to the rest of the device. In some variations the upper arm may be extended/retracted relative to the rest of the device.

Figure 6I:
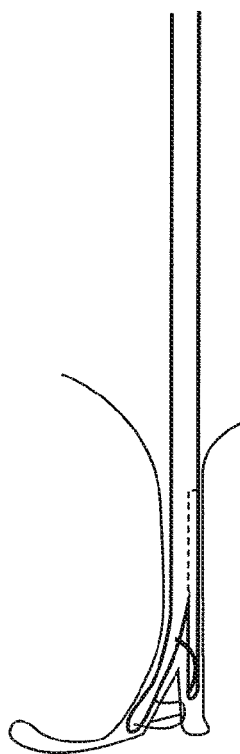
FIGS. 6I-6M illustrate removal of the suture passer, retaining the suture around the meniscus.

Returning now to FIG. 6H, the tissue penetrating member with attached suturing element (e.g., shuttle and suture) is again extended, this time penetrating on the opposite side of the tear from the previous stitch, so that the tear may be stitched closed. The tissue penetrator is passed until it engages (distally) with a second seat region of the second arm; when this occurs the suturing element (e.g., shuttle) is held securely in the seat and is uncoupled (e.g., unclipped, or removed) from the tissue penetrating element, so that the tissue penetrating element can be withdrawn to leave the suturing element behind in the seat on the second arm, as illustrated in FIG. 6I. In some variations the suture passer may be moved slightly (e.g., laterally out of the plane of the cross-section shown) to again pass the suturing element by repeating some of the steps above, e.g., from FIG. 6E forwards, or it may be removed.

Figure 6J:
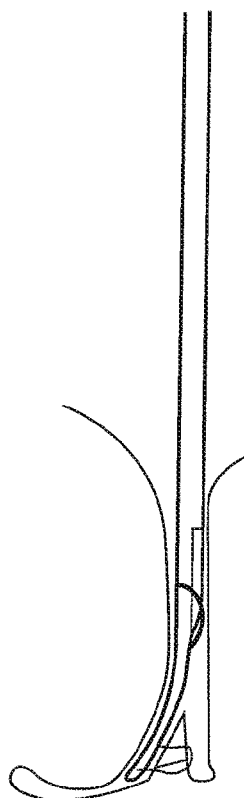
Figure 6K:
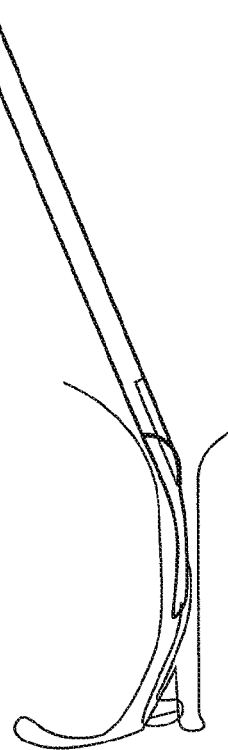
Figure 6L:
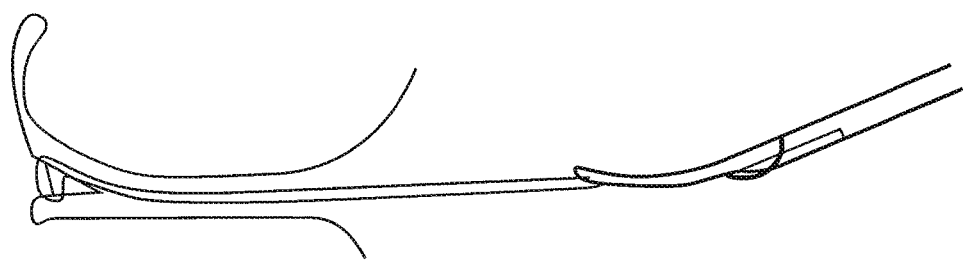
Figure 6M:
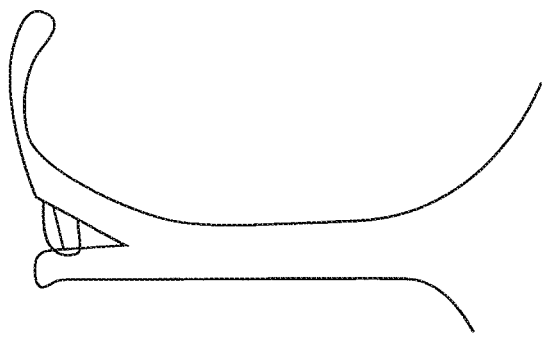

In FIG. 6J, the first arm, and thus the device, is withdrawn axially (proximally), so that the device may be removed, as shown in FIG. 6K. Removing the device leaves the suture and/or lead wire passed through the meniscus, as illustrated in FIG. 6L. The suture maybe drawn through the tissue, leaving behind a loop of suture passing through the tissue. A knot may then be tied or the suture may otherwise be secured, as illustrated in FIG. 6M. A pre-tied knot may be pre-packaged to slide into place as the device is withdrawn.

As described above, the suture passers described herein may be configured to move a suturing element through the meniscus. In general, the suture passers described above are configured use a shuttle which connects to the tissue penetrator extendable and retractable from one of the arms of the suturing device. A suture may be connected to a suture shuttle, either directly or via an extender, such as a lead wire or other structure extending from the shuttle body. A lead wire may be connected (or connectable) to a suture. In some variations the shuttle is configured as a lead wire. In some variations, a separate shuttle that connects to a tissue penetrator is not used, but the lead wire is directly grasped/released from the tissue penetrator. In other variations, the tissue penetrator directly grasps/releases a suture which may also be releasably retained in the seat on the opposite arm from the tissue penetrator. For example, the suture passer may be configured to pull a suture (either attached to a shuttle or without a shuttle) through the tissue using the tissue penetrator.

In general, any of the suture passers described herein may be configured to pull a suturing element through the tissue. As mentioned, a suturing element may be a suture, a suture shuttle, a lead wire, or any combination of these. Of particular interest are variations in which the suture passer includes a tissue penetrator that operates with a suture shuttle from which a lead wire extends. The lead wire may be passed through the tissue and can be connected or coupled to a suture which can thereafter (or concurrently) be pulled through the tissue behind the lead wire.

Thus, in some variations a suture is pulled through the meniscus as the suture passer extends the tissue penetrator through the tissue. For example, the suture may be directly grasped by the suture passer (e.g., the tissue penetrator of the suture passer) or it may be coupled to a suture shuttle and/or lead wire, which is pulled and pushed through the tissue as described above.

In some variation, the suture shuttle may be configured to pull a lead wire thought the tissue. A lead wire may also be referred to as a pull wire, a pull loop, a leash, a lead, a tether, or the like. The lead wire may be connected to a suture shuttle, or it may be held and/or released directly by the suture passer. As described above, in general a lead wire may be configured to connect to a suture. The suture may be coupled to the lead wire before, during or after the lead wire has been passed through the tissue by the suture passer. Once the lead wire has been passed in a suturing pattern through the tissue, the lead wire may be pulled to draw a suture through the tissue. The suture may be tightened and/or knotted, anchored, or otherwise secured in position, and/or to secure tissue or implant material in position within the body. In some variation the lead wire is pulled using the suture passer, which may be adapted for this purpose. In other variations the lead wire is gasped by a separate manipulator or by the surgeon's hand.

A suture shuttle or lead wire may connect to and may be used to pull more than one suture though the tissue. This may allow the suture passer to create a suture pattern without the added resistance of the suture. A lead wire may be thinner, more flexible and lighter than a suture. Once the lead wire is positioned, the suture may be pulled through the tissue in the pattern followed by the lead wire by pulling on the lead wire (and/or the suture shuttle in variations attached to the suture shuttle).

The use of lead wires may also allow more than one loop of suture to be formed through the tissue with the suture passer making only a small number of passes through the tissue. For example, a suture passer may be configured to pass multiple sutures or multiple lead wires through the tissue at the same time.

A. Multiple Pull Wires

Multiple lead wires may be positioned using the suture passer, as illustrated in FIGS. 36A-36C. Multiple lead wires may be particularly useful for forming multiple loops through tissue, as illustrated in FIGS. 36A-36C. In this example, two lead wires may be passed through the meniscus from the upper surface of the meniscus to the lower surface of the meniscus and then back through to the upper surface of the meniscus, as shown in FIG. 36A. In this example, each of two lead wires (although more than two lead wires could be used) is coupled to a suture shuttle (not shown). The suture passer has passed the two lead wires 3603 from the upper surface of the meniscus 3601, shown in cross-section, to the lower surface, and back up through the meniscus near the capsular region to the upper surface, surrounding the tear 3609 in the meniscus. This procedure may be used to form a vertical loop though the meniscus. In FIG. 36A, a suture 3611 is connected to one of the lead wires 3605 at the proximal end of the lead wire.

Once both lead wires have been positioned, as illustrated in FIG. 36A, the suture 3611 may be drawn through the tissue to follow the path formed by the first lead wire 3605 by pulling on the lead wire 3605 to which the suture is attached. In FIG. 36B, the suture 3611 has been pulled around the meniscus from the upper outer surface to the lower outer surface and back through to the upper outer surface, following the path of the first lead wire 3605. In this example, the distal end of the suture is then passed through the remaining lead wire 3603, and the suture 3611 again passes through the tissue along the path of the lead wires, as shown in FIG. 36C. Thus, more than one loop may be formed through the tissue; in FIG. 36C, approximately one and a half loops of suture pass around the meniscus, although if the ends of the suture are knotted together the suture will form two full loops. Passing more than one loop in this manner may allow the suture to be secured without knotting.

In some variations, a suture passer may pass both a suture and a lead wire (or multiple lead wires) to achieve the same result illustrated above.

The devices described herein are particularly well suited for suturing between the upper outer surface of a meniscus and the lower outer surface of the meniscus. Vertical loops, extending radially across at least a portion of the upper outer surface and lower outer surface, as well as longitudinal loops extending longitudinally across at least a portion of the upper outer surface and lower outer surface, are of particular interest.

B. Suturing Vertical loops

Figure 5C:
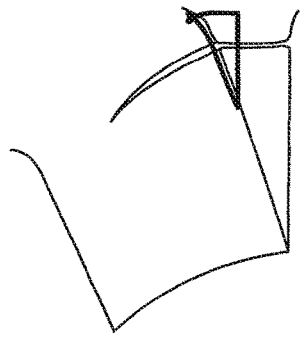
FIG. 5A-5C illustrate meniscus repair using prior art devices.
Figure 5D:
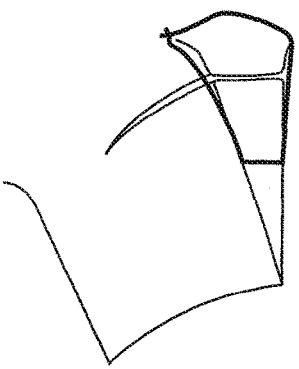
FIG. 5D illustrates meniscus repair using a device as described herein.
Figure 5A:
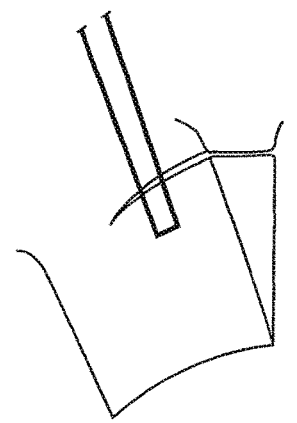
Figure 5B:
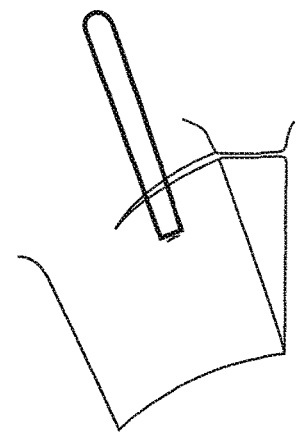

Returning now to FIG. 5, the methods and devices described herein allow for the suturing of vertical loops between the upper outer surface of the meniscus and the lower outer surface of the meniscus, as shown in FIG. 5D (illustrating a full vertical loop), compared to the horizontal loops or partial vertical loops possible with prior art devices (e.g., FIGS. 5A-5C). Studies comparing the biomechanical properties of vertical sutures, horizontal sutures and meniscus repair devices have shown that vertical sutures have superior initial fixation strength and stiffness during load-to-failure testing compared with horizontal sutures and repair devices. As used herein, a horizontal loop or suture pattern typically refers to a pattern that extends roughly parallel to the lower outer surface or upper outer surface, rather than between them. Further, vertical sutures have lower displacements under cyclical loading conditions compared with horizontal sutures and repair devices.

The devices and systems having some or all of the features described herein may be used to place a complete vertical stitch loop around a torn (e.g., longitudinally torn) meniscus while avoiding neurovascular complications and damage. For example, a vertical suture stitch loop may be passed vertically around a longitudinal tear by passing from the lower, tibial-facing outer surface, though the meniscus body (e.g., one side of the longitudinal tear), along the concave, femur-facing upper outer surface of the meniscus and back through the meniscus in a region inward and parallel to the capsule region of the meniscus, e.g., within the capsule region or even outside of the capsule. An example of this stitch is shown in FIG. 5D, and FIG. 37A.

In FIG. 5D and FIG. 37A, a vertical loop is shown made through a region of the meniscus having a longitudinal tear. The resulting suture may be compared with other types of suture fixations ("stitches") made by other devices, as discussed in the background section above, relative to FIGS. 5A-5C. In comparison, the meniscus suture devices described herein may pass a suture through the meniscus near the boundary (or just past the boundary) of the capsule region (to the right of the figure in FIG. 5D and the left of FIG. 37A). Because the device may pass the suture through the meniscus in parallel to the outer capsular region of the meniscus (as illustrated in FIGS. 5D and 37A), and because of the orientation and configuration of the tissue penetrating element, the suture may be passed without risk of plunging deep into and beyond the capsule region. This design may prevent injury to nearby nerves and vascular tissues (e.g., blood vessels). The suture is also passed around the outer upper and lower surfaces regions of the capsule, as illustrated, which may provide optimal support and stiffness for the suture.

In FIG. 37A, the tear in the meniscus 3711 is a horizontal tear 3701 that has been sutured by a closed suture loop 3703.

In FIGS. 5D and 37A, the suturing element (and eventually the suture) is passed from a first outer surface of the meniscus, through to the opposite outer surface of the meniscus, and the suture then extends radially to a second position (inward or outward) to pass back through the meniscus from the second outer surface to return to the first outer surface. In FIG. 5D, the suture element is passed from the upper outer surface to the lower outer surface, radially across the lower outer surface and back up to the upper outer surface where it is knotted. Depending on the configuration of the suture passer, the suturing element may alternatively be passed from the lower outer surface, though the meniscus to the upper outer surface, radially across the upper outer surface and back down to the lower outer surface. For example, in some variations the upper arm of the suture passer positioned opposite the superior surface of the meniscus holds the suturing element which is initially grasped by the tissue penetrator extending from the lower arm of the suture passer after extending through the meniscus, and first pulled down to the lower surface, forming a pattern such as that shown in FIG. 5D. Alternatively, the upper (curved) arm of the suture passer may receive a suturing element preloaded on the tissue penetrator extending from the second arm, forming the pattern such as that shown in FIG. 37A.

Although FIGS. 5D and 37A illustrate full loops of suture, a loop does not have to connect at the ends, although both ends of the loop are on the same (e.g., superior) outer surface of the meniscus. In some variations the ends of the loop are separately anchored, typically on the same outer surface of the meniscus. A loop may refer to a closed loop (as shown in FIGS. 5D and 37A) or an open loop.

C. Suturing Lateral loops

Lateral loops may also be formed. Lateral loops typically extend laterally along the meniscus, and may also be referred to as circumferential loops. The methods and devices described herein describe lateral loops that extend between the upper outer (superior) surface of the meniscus and the lower outer (inferior) surface of the meniscus. This is in contrast with other device and methods that form horizontal suture patterns, which do not extend between the upper and lower outer surfaces, even while extending somewhat laterally or circumferentially.

FIGS. 37B and 37C illustrate a top and bottom view (showing the superior and inferior surfaces), respectively, of a meniscus which has a radial tear 3705 that has been repaired with a lateral loop 3703. In this example, the lateral loop is a closed loop that has been tied on the upper surface. In some variations, multiple loops may be made, spanning the radial tear. On both the upper and lower outer surfaces, the suture extends longitudinally (e.g., circumferentially) along the upper and lower outer surfaces.

D. Knotting the Suture

The sutures passed by the devices described herein may be secured in the tissue by any appropriate securement device or methods, including (but not limited to) anchors, knots, stays, adhesives, clasps, or the like. Thus, a suture passed as described herein may be affixed to be secured within the tissue as appropriate. For example, in FIG. 5D, the vertical loop of suture is anchored at the superior (femur) surface, while in FIG. 37A, the suture is knotted in on the inferior (tibial surface) of the meniscus. A knot may be formed using any appropriate knotting method, device, or mechanism, including known suture knot pushers. In some variations, suture anchors, ties or stays may be used. In some variations, knotless anchors, ties or stays may be used.

Figure 38B:
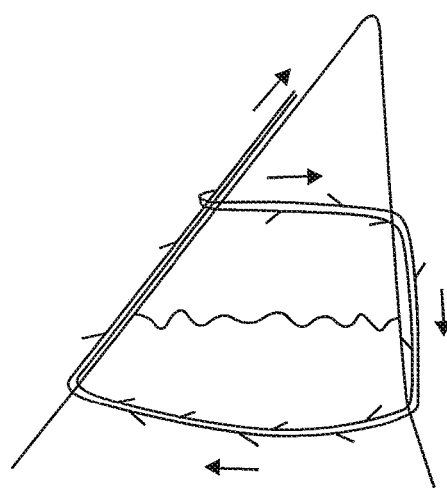
FIGS. 38A and 38B illustrate the use of a barbed suture material with any of the devices described herein in order to suture a meniscus.
Figure 38A:
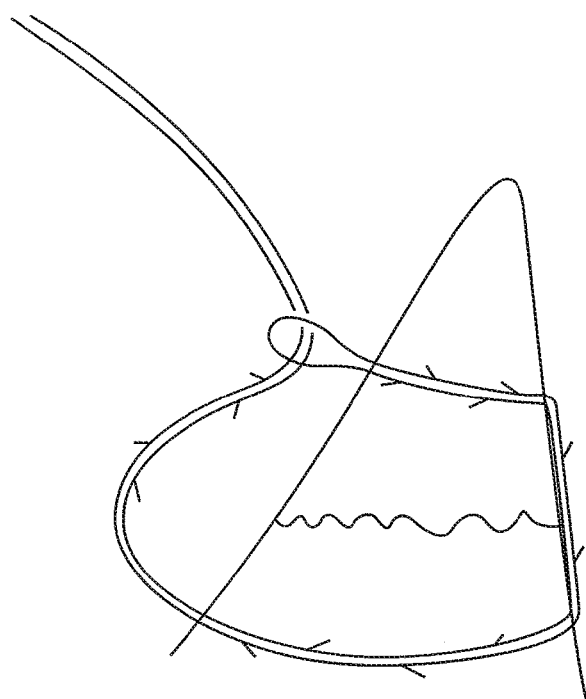

FIGS. 38A and 38B illustrate one variation of a securement method comprising a barbed suture material (which may be referred to as knotless suture material). In this example, the suture material includes barbs that are directionally oriented to prevent movement of all or a portion of the length of the suture in one direction; pulling the opposite direction does not engage the barbs. Thus, the suture material may be pulled into the tissue in the permissive direction, but are prevented from withdrawing from the tissue by the barbs in the suture material.

For example, in FIGS. 38A and 38B, the barbed suture material is positioned in meniscus using a suture passer as described herein. For example, the suture may be connected to a suture shuttle and/or to a lead wire that is passed by the suture passer. In this example, the proximal end of the suture material includes a loop (or the suture material is doubled-back on itself at a point where the orientation of the barbs reverses), though which the distal end of the suture material may be passed, as shown in FIG. 38A. As shown in FIG. 38B, pulling the suture material in the permissive direction (shown by the arrows) by pulling on the distal end of the barbed suture results in tightening the suture and may help joint the torn ends of the meniscus. Additional knots may not be necessary because the barbed suture prevents the suture from loosening.

As mentioned above, described herein are suture passers for meniscus repair. In general, these devices may be referred to herein as meniscus repair suture passers, meniscus repair devices, or simply suture passers.

For example, in some of the variations described herein the suture passers include two elongate arms which may be part of and/or connected to an elongate body. See, e.g. FIG. 40A. Although this configuration is not explicitly shown in every example, any of the examples described herein may include this configuration, unless otherwise specified. The distal end of the device may include a first arm 601 and a second arm 603. One or both of these arms may be slideably disposed so that they may slide proximally and distally 605. One of the arms 601 may be bent or angled (or bendable) to a fixed (or adjustable) degree near the distal end. This bend may correspond to the angle of the tibial surface of the meniscus; similarly the opposite arm 603 may be straight. The bent arm may be bent so that the distal end region is bent relative to the proximal elongate portion of the rest of the arm (or the rest of the device), and therefore relative to the opposite arm. The arms may be slid relative to each other (e.g., by extending the second arm 603 in FIG. 40A) to form an acute opening (which corresponds to the outer surface of the meniscus. When the straight arm 603 is retracted proximally relative to the bent arm 601, the device may be deployed even within the relatively narrow confines of the meniscus; once the bent arm is deployed adjacent to the tibial surface (or as it is deployed), the straight lower arm may be extended.

Any of the variations of the devices described herein may be configured to include this configuration, which may make the device easier and more accurately positionable. In some variations the bent arm 601 is curved at the distal end, rather than forming an abrupt angle. Alternately, in some variations the arms may be fixed relative to each other, rather than sliding proximally and distally. In some variations the upper and lower arms may open and close, scissor-like.

All of the variations described herein are configured to pass one or more suturing elements through the meniscus in order to suture it. A suturing element may include a suture, a suture shuttle connected to the suture, a pullwire or loop through which a suture may be placed for pulling, or the like. Suturing elements as used herein may include any suturing element (including a suture), alone or in combination, that is passed through the meniscus tissue to directly or indirectly pass a suture. For example, the suture element may be any appropriate suture. The suture element may be a plurality (e.g., a bundle) of sutures. In some variations, the suturing element is a suture shuttle to which a suture may be attached; in some variations the suture element may include both the suture and the suture shuttle. In some variations the suture element is a suture puller, such as a loop or pullwire to which a suture may be connected; a suture puller may be passed through the tissue with the suture passer devices described herein, and the suture may be pulled through (suturing the tissue) either after or while the suture is being pulled into position. Any appropriate suture may be used, including, but not limited to natural and artificial materials (including fabrics, metals, polymers, and the like); sutures may be woven, braided, spun, barbed, chained, etc. Sutures may be absorbable or non-absorbable. Sutures are typically biocompatible. Coated sutures (e.g., including a therapeutic substance, adhesive, or the like) are also contemplated. Any appropriate size may be used.

Many of the variations described herein include one or more tissue penetrators or tissue penetrating elements configured to penetrate tissue for placement of a suture element and therefore a suture. In some variations the tissue penetrator is an elongate structure configured to extend and retract into one or both arms of the suture passer. A tissue penetrator may be configured as a needle (including compound needles, telescoping needles, or the like). The tissue penetrator may be curved or straight and may be bendable. For example, tissue penetrators formed of a shape memory alloy may be used. Tissue penetrators may have a sharp or tissue-penetrating distal tip or tip region. In some variations the tissue penetrator may be configured to include a suture element securing region. For example, a tissue penetrator may include a docking region for a suture shuttle. In some variation the tissue penetrator includes a hook or latch region for holding a suturing element (such as a suture). In some variations the tissue penetrator includes two or more suture holding regions; examples of such regions include cut-out regions into the body at or near the distal end of the tissue penetrator for holding the suture element. In general, a tissue penetrator may be formed of any appropriate material, including, but not limited to metals (including shape memory alloys such as Nitinol and others), ceramics, or the like. A tissue penetrator may be configured as a column, tube, cylinder, ribbon, wire, or the like including combinations of these, and may be hollow or solid (or may include hollow and/or solid regions). In some variations the tissue penetrator may be configured to be an assembly of different components (which may be individual tissue penetrators) which may be collected together; for example, a tissue penetrator assembly may include two tissue penetrators that are slidably disposed relative to each other.

Any of the devices described herein may include a proximal handle 612 (or handles), as well as one or more controls for controlling the various action of the device, including extending, retracting, opening, locking or otherwise moving one or more arms, extending and retracing the tissue penetrator or tissue penetrators, and in some variations grasping or releasing the suturing element.

The proximal handle shown in many of the examples (e.g., FIG. 40A) includes a slider 615 control that may extend/retract the tissue penetrator; in some variation, this slider may be a knob, button, trigger, or any other appropriate control. For example the control may be configured to automatically actuate the tissue penetrator, or to assist the user in moving the tissue penetrator through the tissue. For example, the control may be spring loaded or may include a motor or other mechanical assist.

In some variations the handle region may also include indicators, markings, or the like to provide visual or tactile feedback to the operator on the status (e.g., position, orientation, etc.) of the device or components of the device. The handle may include depth markings, or other indicators showing the deployment status of one or both jaws and/or the tissue penetrator.

The handle may also include one or more locks, stops, or stays to hold or maintain one or more of the device components in a desired (or arbitrary) position. For example, the device may include a lock to releasably secure the arms relative to each other, or the second arm 603, relative to the elongate body of the device. In some variations the handle lock may include a button, detent, tab, latch, or control that can be engaged/disengaged from the proximal handle. The handle may include indicators indicating the relative position of the arms, including how extended/retracted the low arm is relative to the bent upper arm. In variations having an adjustable bend, the handle may include an indicator indicating the bend in the upper arm.

Figure 40A:
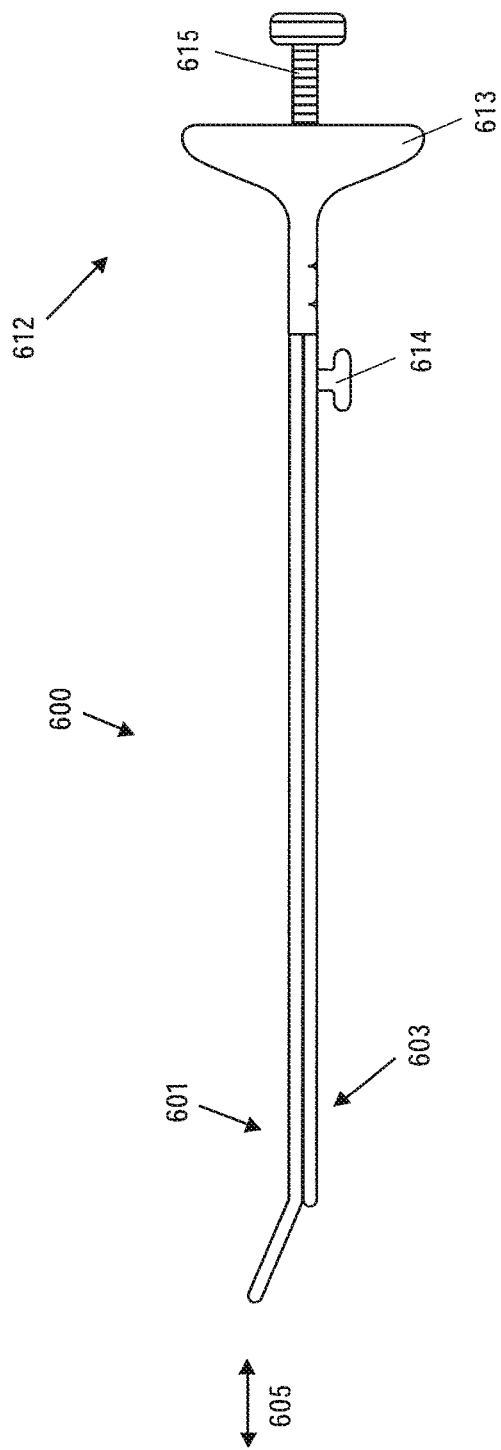
FIG. 40A shows one variation of a meniscus suture passer.

The exemplary handle 612 shown in FIG. 40A includes a grip region 613 that may be grasped or hand held. Additional sliders 614 may also be included; in this example the slider may be finger actuated, and may be used to move the lower arm 603 proximally or distally. A button may be used to engage/disengage a lock that allows or prevents the proximal or distal movement; the button may be on the slider, or elsewhere.

In some variations the device may also be adapted for use with other percutaneous or minimally invasive devices or systems. For example, the device may include one or more mounts, fasteners, or attachment sites for interaction with a cannula or stereotactic positioning device. In some variations the device may be adapted for use with visualization equipment. For example, some variations of the meniscus suture passer include a channel, passage, and/or port for use with a camera, guidewire, or the like.

The devices described herein may be sized to work with one or more patient sizes. For example, the devices described herein may be configured in multiple sizes (e.g., small, medium, large, etc.) for use with different patient sizes. In general the devices described herein may be configured as single-use (including pre-loaded configurations) or for multiple uses (reusable). These devices are typically sterilizeable, and compatible with surgical use.

For example, any of the meniscus suture passers described herein may be pre-loaded with one or more suturing elements (including suture). In some variations the devices may include a pre-tied knot to assist in suturing. In general, the device may be configured to help control the suture and the interaction between the suture and the device, preventing tangling or confusion with the suture or suturing element. For example, the devices described herein may have one or more external or internal suture channels, passages, attachment sites, or the like, for holding/retaining a suturing element (such as suture). In variations in which the suture is preloaded into the device, the suture may be held within (or against) the suture passer so that the suture is held ready for engagement with the tissue penetrator. The suture may be held in position relative to the suture passer by frangible attachments (e.g., wax or other removable attachments) that may be released by the application of sufficient force (including very gentle, low force) from a user.

As will be described in greater detail below, the suturing devices described herein typically include one or more suturing element docks or capture elements on one or both of the arms of the device. A suturing element dock is configured to hold and/or receive and hold a suturing element. The suturing element dock may receive a suturing element from the tissue penetrator after passing it though the meniscus. In some variations the suturing element dock maybe configured to hold the suturing element (e.g., suture) until it can be retrieved by the tissue penetrator. Different types of suturing element docks may be used. In some variations a first suturing element dock may be configured to hold the suturing element in position on an arm of the device until the tissue penetrator can engage the suturing element within the dock and withdraw it from the dock; a second suturing element dock may be configured to receive the suturing element from the tissue penetrator, stripping the suturing element from the tissue penetrator so that the suturing element remains in the dock while the tissue penetrator is retracted back into the opposite arm. Suturing element docks may be configured so that a suturing element is actively, passively and/or both actively and passively retained in the dock. For example, the suturing element may be held in the dock by a retaining pin or clamp, or by a membrane. A retainer (e.g., retaining pin or other surface) may be spring-loaded, pneumatically loaded, or the like, to hold the suturing element within the dock. In some variations the dock includes a retaining membrane or valve that allows the suturing element to readily enter the dock, but prevents it from easily leaving the dock as the tissue penetrator is withdrawn.

A suturing element dock may include an engagement member to engage with a tissue penetrator and help couple or uncouple a suturing element from the tissue penetrator. For example, a dock may include a channel or post that guides or retains the suturing element so that it can be left behind in the dock when the tissue penetrator is withdrawn.

PART I: SUTURE PASSERS WITH SWITCHABLE EXIT PATHWAYS

Some variations of the suture passers described herein have a single tissue penetrator (e.g., needle) that is configured to extend from and retract into a first arm of the device, but to cross at two (or more) distinct positions along the axial length of the suture passer. In this way, the suture passer can pass a suturing element (and thus a suture) from a first position along the length of the suture passer, through the meniscus, then along an outer surface of the meniscus proximally or distally (relative to the length of the suture passer) and back through the meniscus from a second position along the length of the suture passer, where the second position is located proximally or distally from the first position. This suture passing may be performed without removing the suture passer from the tissue. Thus, such devices may place radial as well as longitudinal loop stitches.

For example, FIGS. 40A-40G and 41A-41B illustrate one variation of a meniscus suturing device having a single tissue penetrating element that is configured to extend from one arm, and through the meniscus in two distinct longitudinally-spaced locations in order to pass a suturing element from one side of the meniscus, to the opposite side of the meniscus and back to the first side of meniscus, e.g., from the femoral surface of the meniscus to the tibial surface of the meniscus, and back to the femoral surface of the meniscus to form a suture loop completely around the meniscus. Although the variation shown in FIG. 40A-41B begins and ends the suturing on the femoral surface of the meniscus, the device may be configured to begin and end the suturing on the opposite (tibial) surface.

In some variations, such as the device shown in FIGS. 40A-41B, include a deflector, switch, interposer, toggle, shoulder, fulcrum, or the like, which is configured to be interposed into the path of the tissue penetrator and redirect it from a first pathway through the meniscus to a second pathway through the meniscus.

FIGS. 40B to 40G illustrate one variation of a meniscus suture passer in which the suture passer includes a switch configured as a ramp, deflector or interposer 601 that will alter the direction of the tissue penetrator 603 so that it extends from the lower arm 621 in a second path to extend between the arms of the device. For example, in FIG. 40B, the meniscus suture passer 600 is positioned around the apex of the meniscus 609 so that the upper arm 623 extends along the femoral surface of the meniscus and the lower arm 621 extends along the tibial surface of the meniscus. In FIGS. 40B-40G the device is shown in partial longitudinal cross-section, to illustrate the movement of the tissue penetrator as it sutures the meniscus 609. The tissue penetrator 603 in this example maybe an elongate ribbon-shaped tissue penetrator having a tissue-penetrating distal end (e.g., a sharp distal end) with an attachment site for a suturing element at or near the distal end. Examples of such tissue penetrator are described below in more detail with reference to FIGS. 42A-46K.

Figure 40B:
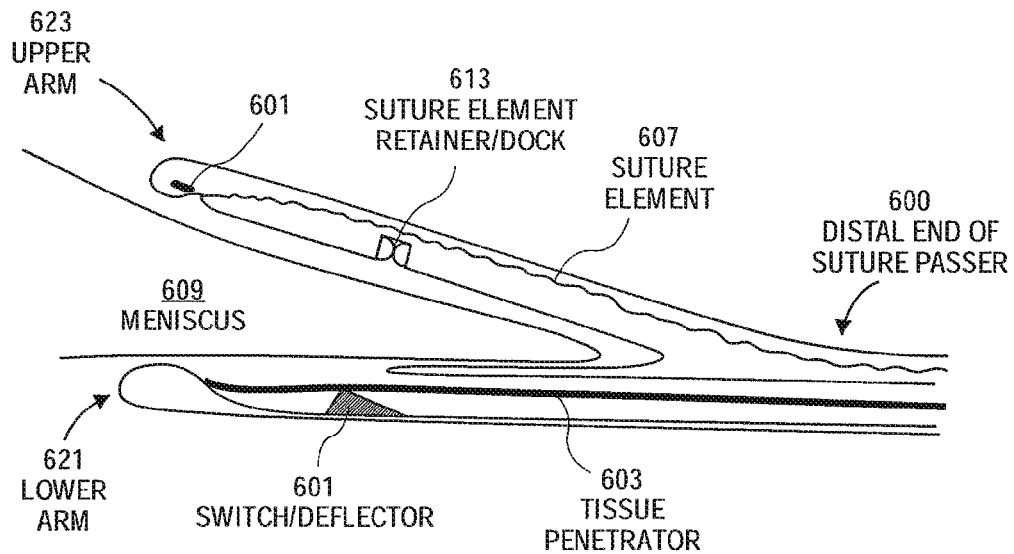
FIGS. 40B-40G illustrate operation of the suture passer of FIG. 40A.
Figure 40C:
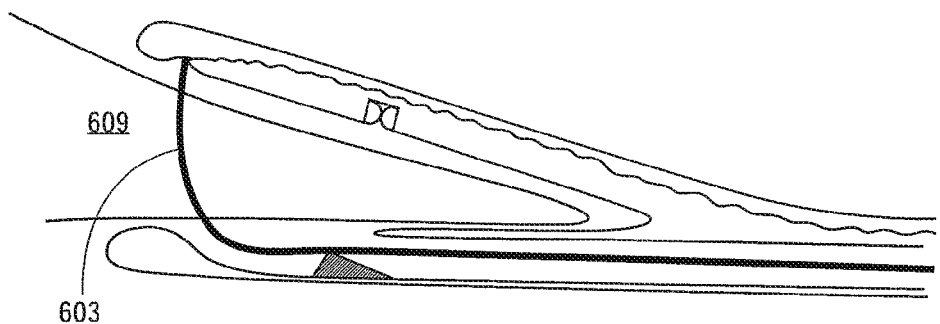
Figure 40D:
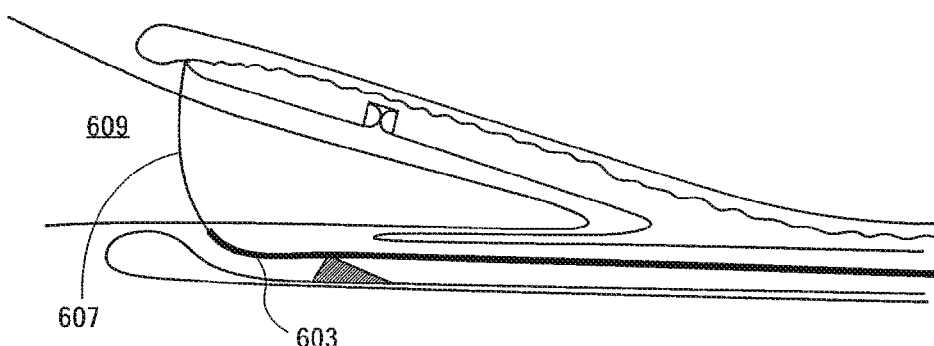
Figure 40E:
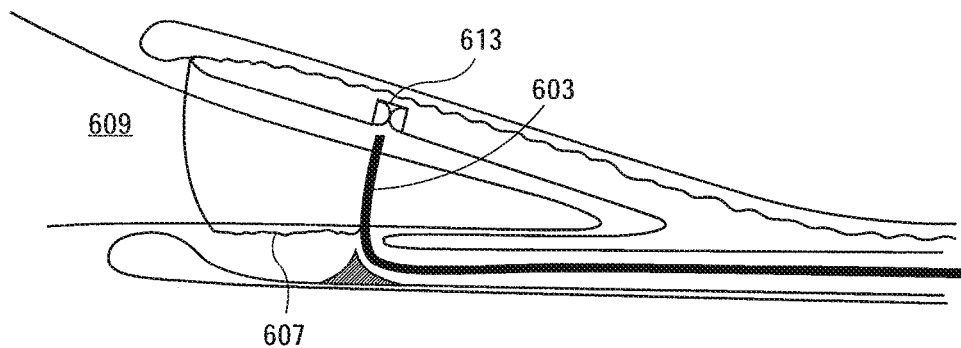
Figure 40F:
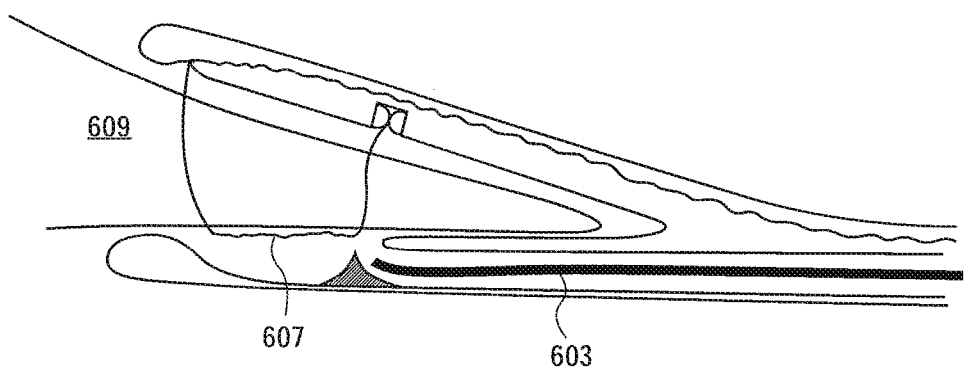

The upper arm 623 of the suture passer 600 in FIG. 40B includes two suturing element docks 612, 613. In this example, the device is pre-loaded with a suturing element (suture 607); hereafter this suturing element will be referred to as simply a "suture", although it should be understood that other suturing elements may be used. In FIGS. 40A-40F the suture is shown pre-loaded within the upper arm 623, however the suture could be held by the device, and pre-loaded into the device, while extending external to the arms of the suture passer.

In FIG. 6C the tissue penetrator 603 is extended distally to cross through the meniscus and engage the suturing element dock 612 on the opposite arm. The tissue penetrator may be extended from the device by pushing or otherwise driving the tissue penetrator from the proximal end of the device; in some variations a plunger, motor, driver or the like on the handle drives the tissue penetrator distally. Distal motion of the tissue penetrator extends the tissue penetrator towards the distal end of the lower arm 621, where it can be guided out of the lower arm 621 at an angle relative to the long axis of the lower arm and into the meniscus towards the opposite arm. In some variations the tissue penetrator is made of a shape-memory material and/or is shape set or otherwise pre-curved to bend upwards, towards the opposite arm. In some variations, the distal end of the tissue penetrator is deflected by a ramp or guide region on the distal end that bends the tissue penetrator and directs it towards the opposite arm. In general the path from the lower arm to the upper arm is stereotyped and may be controlled, thus the tissue penetrator passes through the meniscus in a predetermined pathway so that the distal end of the tissue penetrator meets with the first dock (suturing element dock 612). This is illustrated in FIG. 6C. In this manner the distal end region of the tissue penetrator may engage the suture (e.g., by hooking, clamping, or otherwise connecting with it) so that when the tissue penetrator is withdrawn, as illustrated in FIG. 6D, the suture is also withdrawn back through the meniscus in the first pathway formed by the tissue penetrator.

The tissue penetrator may be moved to extend from and retract into the lower arm 621 along a channel or path (not visible in FIGS. 40B-40G). The channel or path may include a track or channel along either side of the lower arm in which the tissue penetrator may slide. This track may be lubricated. The channel, path or track guides the motion of the tissue penetrator and may allow the tissue penetrator to move in a predictable and controlled manner in, out and within the lower arm.

After retracting the tissue penetrator into the lower arm, as shown in FIG. 6D, the tissue penetrator (with attached suture) may be withdrawn proximally within the lower arm of the suture passer; when the distal tip region of the tissue penetrator is pulled proximally past the switch/deflector element 601, the switch or deflector may be extended upward, forming a ramping surface so that if the tissue penetrator is extended distally it will be deflected up and out of the lower arm and though the meniscus, to engage with the proximally located second suturing element dock 613, as shown in FIG. 6E. The attached suture will be pulled along with the tip region of the tissue penetrator.

Figure 41A:
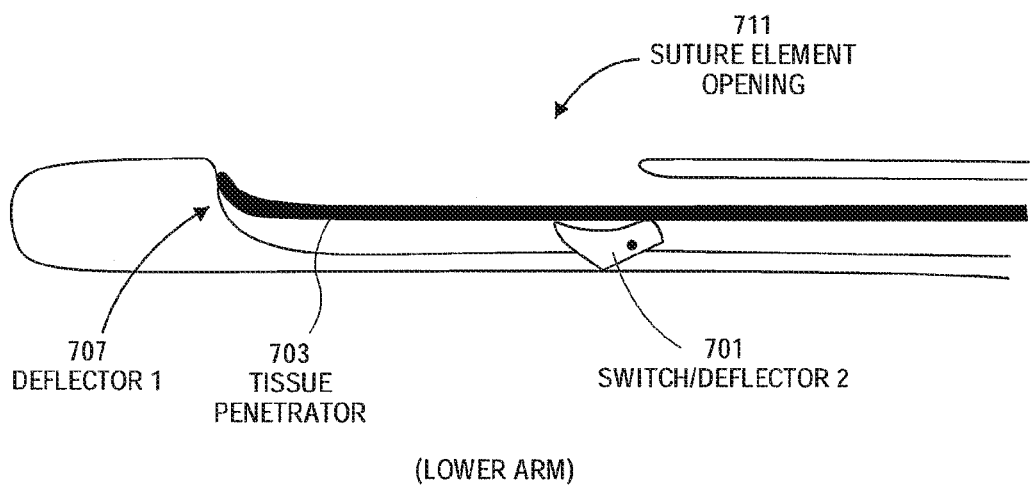
FIG. 41A shows an enlarged view of the lower arm of the suture passer of FIGS. 40A-40G.
Figure 41B:
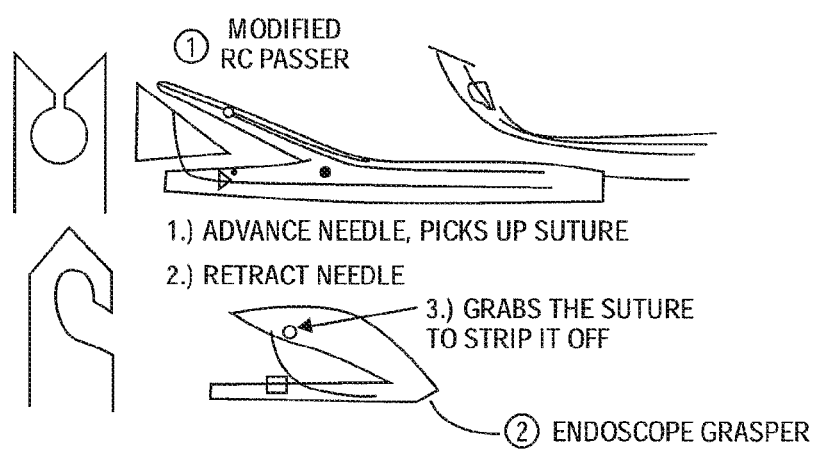
FIG. 41B Shows another variation of a meniscus suture passer.

In some variations the switch/deflector is configured to be spring loaded, so that when the distal end of the tissue penetrator is withdrawn proximally with the suture, the switch is permitted to rotate or otherwise move upwards forming the ramp against which the tissue penetrator may now be deflected. FIG. 41A shows this configuration in greater detail, in which the switch/deflector 701 is configured to rotate forwards and/or upwards and deflect the distal end of the tissue penetrator through the meniscus from a second point along a second predetermined path to engage the dock. As mentioned, in some variations, the switch element is spring-loaded and extends upwards upon withdrawal of the tissue penetrator. In some variations the switch may be controlled by some other switching member, including a tendon or other structures, some variations of which may be actuated from the proximal end of the device.

Figure 40G:
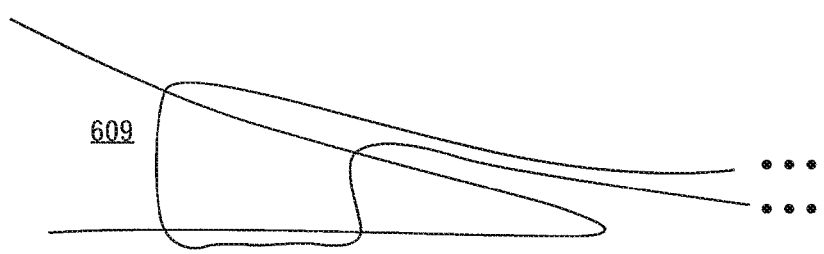

Once the distal tip region engages the second dock 613, the suture is retained by the second dock and the tissue penetrator can be withdrawn back across the meniscus and into the lower jaw, as shown in FIG. 6F. The suture is therefore passed completely through the meniscus twice. Thereafter, the lower arm can be retracted proximally (in some variations) and the upper arm and rest of the suture passer withdrawn, leaving behind the suture as shown in FIG. 40G. In some variations the suture may then be tied. As mentioned, the device (e.g., the upper arm) may include a prettied knot, which may be used to secure the suture.

Any appropriate tissue penetrator may be used, including those having hooks, graspers, pinchers, barbs, channels, or the like, for releasably securing to a suturing element. FIGS. 42A-46K illustrate some variations of tissue penetrators configured as flattened ribbons or bands. The distal ends of these elements are adapted to releasably hold a suturing element (e.g., suture), and may also be adapted for penetrating tissue and engaging a suturing element dock. For example, FIGS. 42A-8D illustrate variations of a ribbon-shaped tissue penetrator that may be formed of a shape memory alloy (e.g., Nitinol) and configured to hook or otherwise grasp a suture so that the suture may be pulled through the tissue by the tissue penetrator. In general, any dimensions mentioned in any of the figures herein are intended for illustration only, and may be modified.

Figure 42E:
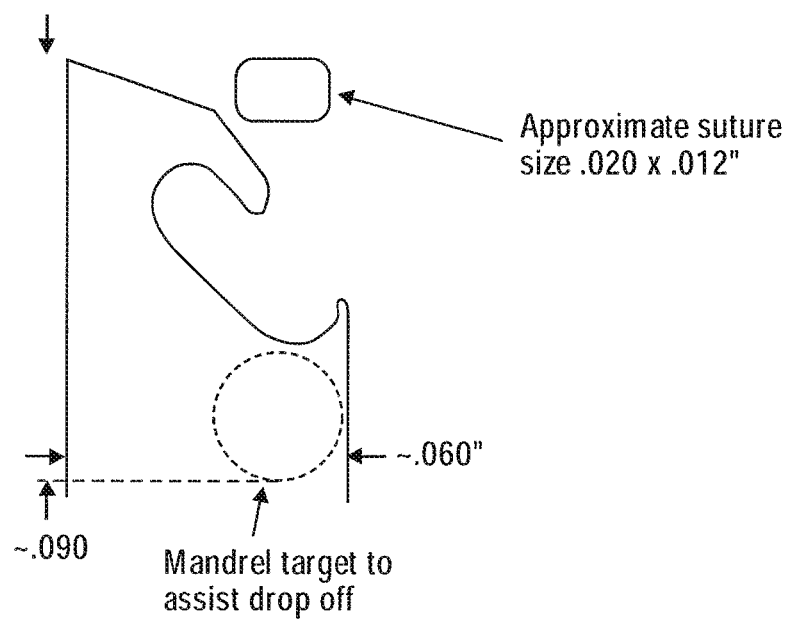

For example, in FIG. 42A, the tissue penetrator includes an angled hook region into which a suture may be slide and pulled when the distal end region of the tissue penetrator is passed into a dock. FIG. 48B shows another variation of a tissue penetrator in which the distal tip region has been adapted with a second bevel region that may help both in penetrating the tissue and also in guiding the suturing element (e.g., suture) into the slot where it can be held. In FIG. 42C, a variation in which the distal tip region is slightly smaller is illustrated; this variation may create room for the suturing element to more easily drop into the hook region where it can be held, as shown in FIG. 42D. FIG. 42E shows another variation of a tissue penetrator in which the capture or retaining region for holding the suturing element is recessed within the body of the tissue penetrator and includes both an upper and lower lip region to aid in retaining the suture as the tissue penetrator is driven between the lower to the upper arms.

Any of the tissue penetrators described herein may be configured as flat ("ribbon") needles. In operation, including when engaging and disengaging the suturing element within a suturing element dock, additional structures may be used to guide, insert and remove the suturing element from the tissue penetrator. For example, in FIG. 42E the dashed lines indicate where a mandrel or other element within a dock may be used to help drop off a suture from the needle into the dock; in some variations a second mandrel or guide member (not shown in FIG. 42E) may be used to push the suture from the left side of the capture region to the right side so that the suture may be pushed left within the dock when the tissue penetrator is removed.

Similarly, FIGS. 43A-43D show another variation of a tissue penetrator in which the suture capture region 901 is centrally positioned and accessed from the tip of the needle. The channel 903 in the relaxed state has a narrower diameter than the suture; this channel may be enlarged (e.g., by a mandrel or by the suture itself) in order to pick up or drop off the suture. FIGS. 43B-43D show variations of this type of tissue penetrator having different adaptations to aid in inserting and/or withdrawing the suture from within the capture region 901.

Figure 44B:
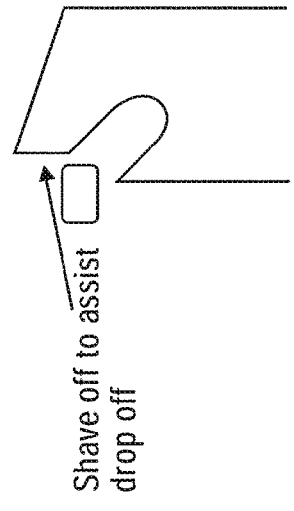
FIGS. 44A-44C illustrate variations of tissue penetrating elements which may be used with some of the suture passers described herein.
Figure 44C:
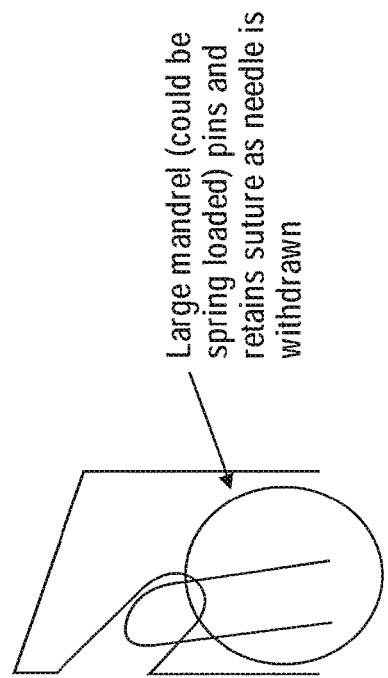
Figure 44A:
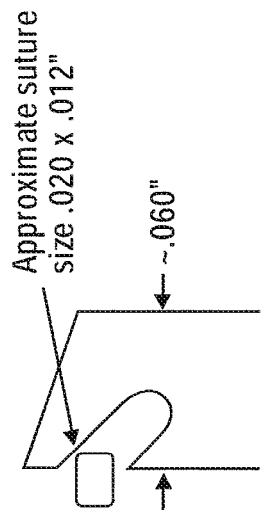

FIGS. 44A-44C illustrate another variation of a tissue penetrator similar to the variation shown in FIGS. 42A-42D, including the use of a mandrel or additional guide structure to help insert, remove, and retain the suture within the tissue penetrator. The operation of one variation of a suture element dock (which may be referred to as a suture dock) is illustrated in FIGS. 44D-44F.

Figure 44D:
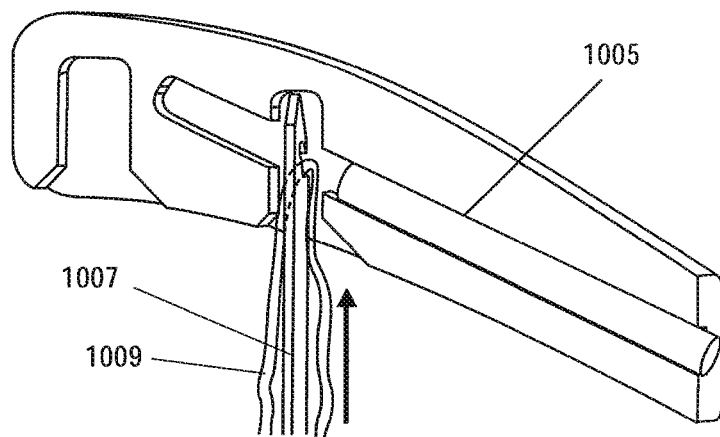
FIGS. 44D-44F illustrate one variation of a dock for receiving a suturing element from a tissue penetrator.
Figure 44E:
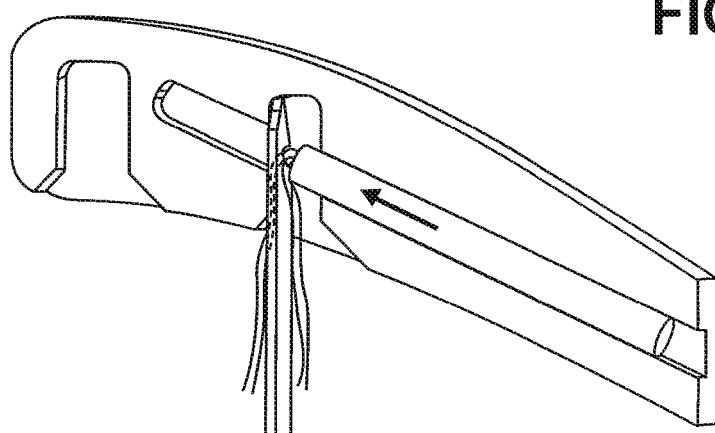
Figure 44F:
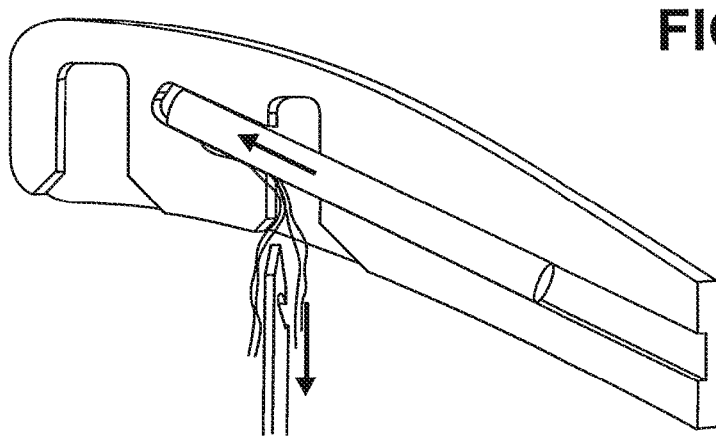

In some variations, such as the example shown in FIGS. 44D-44F, the suture dock includes a suture element retainer 1005 (which may also be referred to for convenience as a suture retainer) configured to remove or aid in removal of the suture element from the tissue penetrator and/or to retain the suture within the dock after the tissue penetrator is withdrawn from the dock. In the example shown in FIG. 44D-44F, the suture retainer is a mandrel or shaft 1005 that extends within the arm having the suture dock. In FIG. 44D, a tissue penetrator 1007 enters the dock with a suturing element 1009 (e.g., suture, lead wire, shuttle, etc.) and the retainer is initially retracted proximally (though it may be configured to retract distally in some variations).

As shown in FIG. 44E, the retainer may then be driven against or partially through the tissue penetrator to engage the suturing element and de-couple it from the tissue penetrator (arrow in FIG. 44E). The tissue penetrator may then be withdrawn, as shown in FIG. 44F, and the suturing element 1009 is left behind in the dock. In FIG. 44F the retainer is driven against the suturing element and further distally (arrow) after the tissue penetrator is removed, which may help retain the loop of suturing element within the dock even after removal of the tissue penetrator. The device may be configured so that the suturing element may be pulled out of the dock (and out of engagement with the retainer) when sufficient force is applied on the suturing element (e.g., pulling it); alternatively, the device may be configured to retain the suturing element within the dock until the retaining element is released.

In some variations the dock and/or retainer are configured so that the tissue penetrator displaces the retainer, which may be extended across or partially across the dock. For example, the retainer may be biased to extend across the dock, and the tissue penetrator may push against the bias force as it is driven into the dock. The retainer may therefore push against the side(s) of the tissue penetrator while the tissue penetrator is within the dock, and the retainer may thereby retain the suturing element in the dock when the tissue penetrator is withdrawn from the dock. Two or more retainers may be included in a single dock. For example, a biased (e.g., spring loaded) retainer may push against each side of a tissue penetrator and thereby uncouple the suture from the tissue penetrator as the tissue penetrator is withdrawn back out of the dock.

In some variations the mandrel is controlled from the proximal end of the device either manually or automatically, while in some variations it extends only within a region of the upper arm. A spring or other bias member may be include (not shown) to drive the mandrel against the side of the tissue penetrator when the tissue penetrator is within the dock.

Figure 45B:
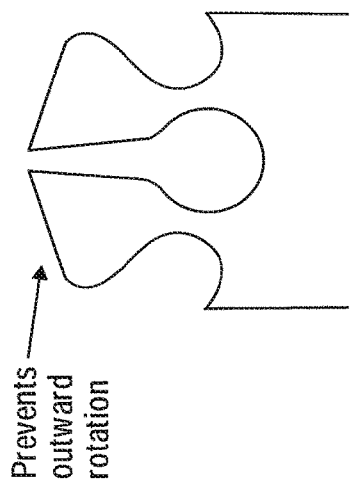
FIGS. 45A-45C illustrate variations of tissue penetrating elements which may be used with some of the suture passers described herein.
Figure 45C:
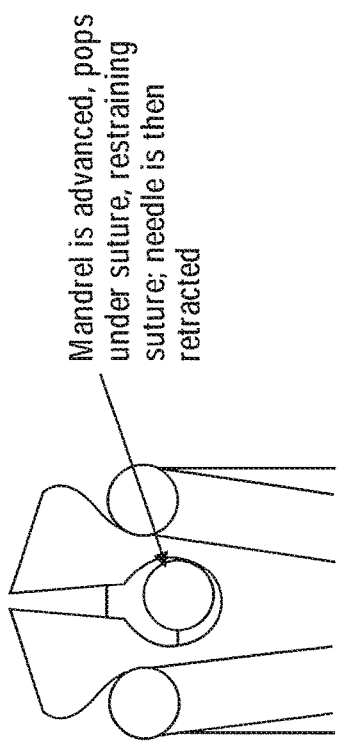
Figure 45A:
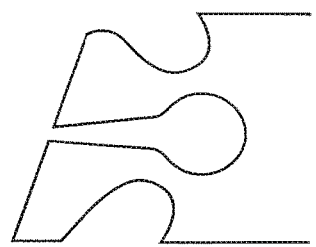

FIGS. 45A-45C illustrate another variation of a tissue penetrator in which, rather than being held within a central retaining region, the suturing element is at least partially wrapped around the tissue penetrator, as shown in FIG. 45C. A central opening through the tissue penetrator may be configured to help remove or attach the suture to the tissue penetrator.

FIGS. 46A-46K illustrate a variety of tissue penetrators configured as ribbon-type needles having suture retaining regions at or near their distal ends.

In some variations, the tissue penetrator may be configured to include a grasper or grasper-type region for engaging the suturing element. For example, in FIGS. 47A1 and 47A2 show one variation of a tissue penetrator including a grasper at the distal end. This grasper may be actuated actively by pulling or pushing on a tendon member 1301. Other variations, including the variation shown in FIG. 47B may include a lock or collar mechanism 1303 that holds pre-biased jaws open or closed; moving the collar or lock allows the jaws to open or close. In FIG. 47C, the grasper is configured to include a projecting member 1305 that helps retain the suture between the jaws when they are closed.

Figure 3:
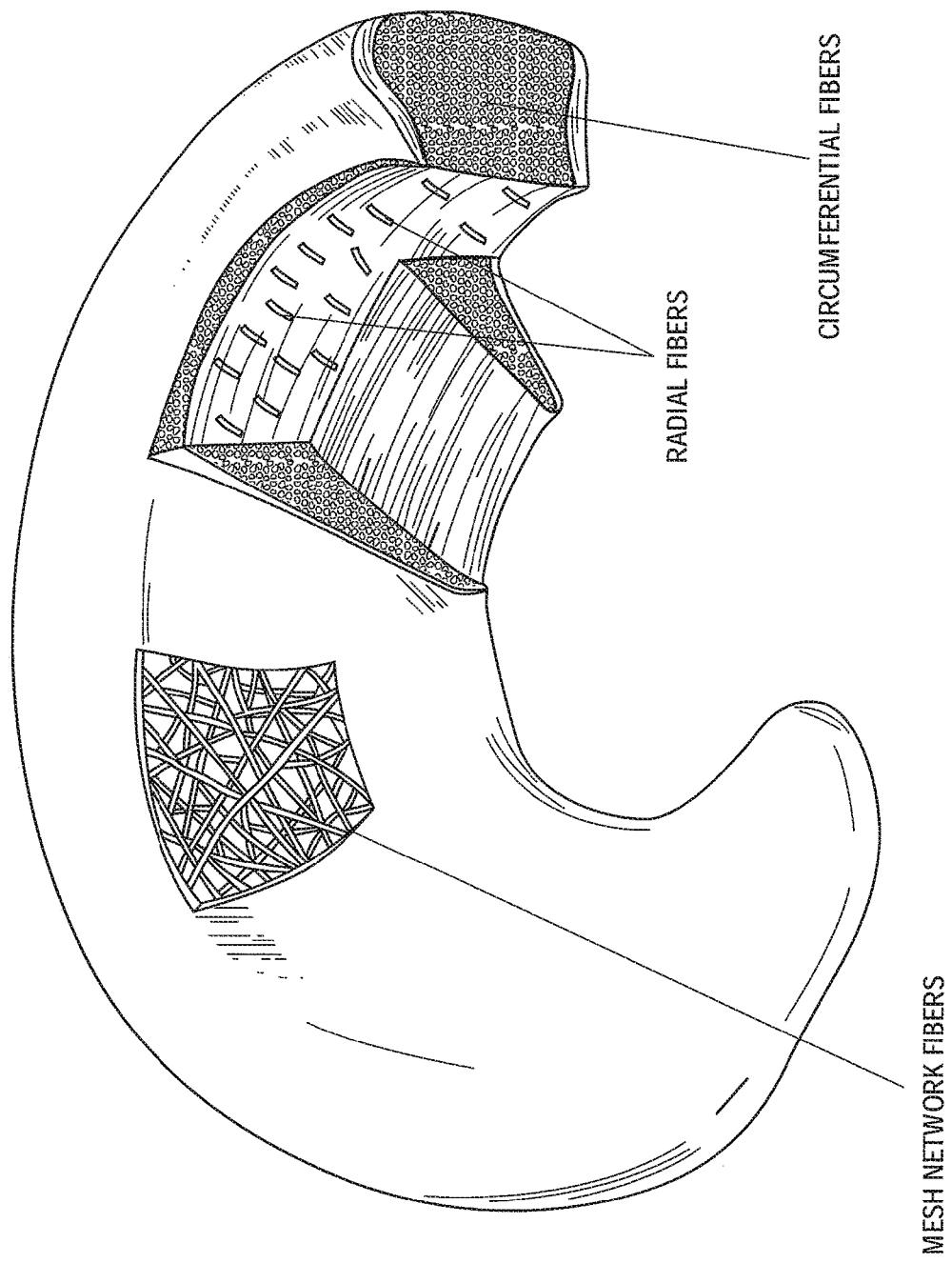
FIG. 3 illustrates the structure of a meniscus.

FIG. 47D1 shows a partial side view of the distal end of a meniscus suture passer, and FIG. 47D2 shows a slightly enlarged view of the dock region with tissue penetrator having a grasper-type distal end engaged with the dock. In this variation the dock includes a biasing member (e.g., mandrel or biasing surface) against which the grasper may be driven to open the jaws of the grasper and allow the suture to be released into the dock. In FIG. 47D2 the distal end of the tissue penetrator is a grasper such as the variation shown in FIG. 47B, however the jaws of the grasper 1322 in this variation are biased closed until they can be opened against a biasing member such as the one shown in the dock 1325. FIG. 47D3 shows a perspective, partial cut-away view of another variation of a dock of a suture passer device showing a retainer within the dock and the tissue penetrator with attached suturing element. In this example, the clip-like retainer element is partially displaced by the tissue penetrator as it enters the dock and the suturing element is held by the retainer while the tissue penetrator is withdrawn.

As mentioned above, any of the devices described herein may include a tissue penetrator as illustrated above in FIGS. 42A-47D. Other tissue penetrators may include cannulated, and/or cylindrical members (rather than ribbon-shaped members) or members having variable diameter shapes/thicknesses along their length.

Another variation of a meniscus suture passer device having a single tissue penetrator configured to have two distinct tissue-crossing regions is illustrated in FIGS. 48A-48I. In this variation, the tissue penetrator and lower arm are configured so that the switching element is not necessary, because the tissue penetrator is deformed during operation or pre-biased before use to assume a curved configuration so that it crosses the space between the upper and lower jaws in a predetermined manner when the distal ends of the device are in the deployed configuration around the meniscus.

Figure 48C:
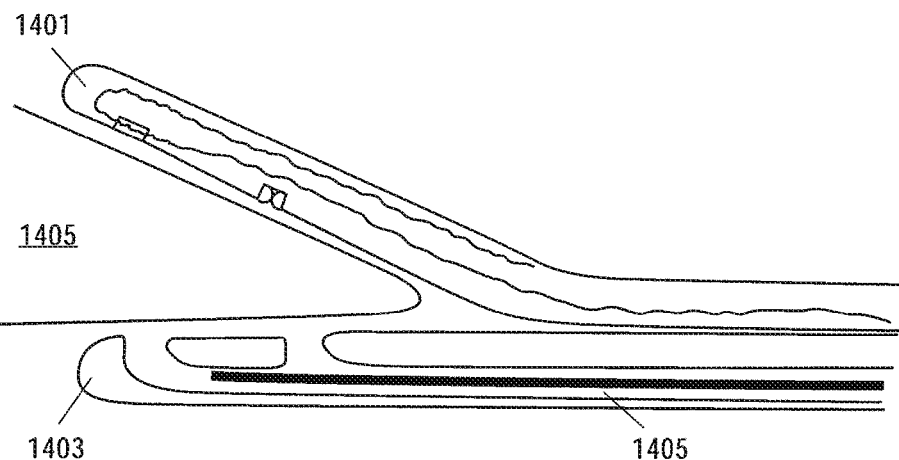

FIG. 48A shows a perspective view of a suture passer similar to the device shown in FIG. 40A. FIGS. 48B-48H illustrate an enlarged view of the distal end region of the device during operation. For example, in FIG. 48B, the device is shown in the un-deployed, delivery configuration, in which the lower arm 1403 is retracted. The lower arm is configured to move longitudinally proximally and distally so that the device can be positioned around the meniscus. In any of the variations described herein, one of the arms (e.g., the lower arm) may be configured to extend and retract, and may be lockable in a predetermined position so that the tissue penetrator travels between the two arms in a predictable manner, and engages with one or more docks on the opposite arm.

The tissue penetrator 1405 is initially positioned within the lower arm 1403. In variations in which the tissue penetrator is pre-biased (bent) and would otherwise extend upwards from the lower arm, it may be held initially between the distal exit 1407 and the proximal exit 1409 out of the lower arm. In variations in which the tissue penetrator is not (or not fully) pre-biased in this manner, the tissue penetrator may be positioned anywhere within the lower jaw; movement out of the distal exit 1407 will deform the tissue penetrator so that it assumes the bent shape, as described in more detail below.

Figure 48D:
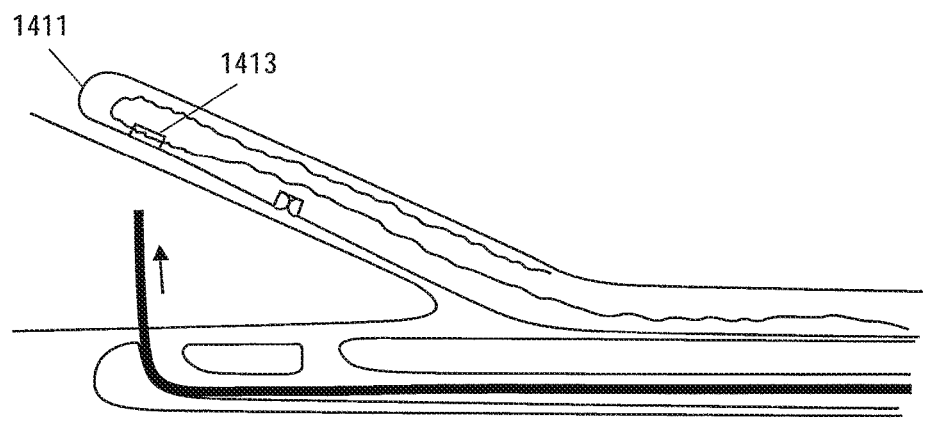

In this example, once the lower arm 1403 has been extended under the meniscus 1405, as shown in FIG. 48C, the tissue penetrator 1405 may be extended through the meniscus, as shown in FIG. 48D. To being suturing the meniscus, the tissue penetrator is driven distally, so that it extends through the meniscus and engages with the suturing element (e.g., a suture) within the distal dock 1413 on the upper arm 1411. As mentioned briefly above, in some variations the act of driving the tissue penetrator out of the distal exit on the lower arm may result in bending (e.g., shaping) the tissue penetrator so that it extends across the tissue in a predictable manner; this shape may be retained even after retracting the tissue penetrator into the lower arm. The bend radius seen by the tissue penetrator in the distal exit of the lower arm may be chosen so that the strain applied to the tissue penetrator is sufficient to deform it, including when the tissue penetrator is formed of a shape memory alloy.

Figure 48E:
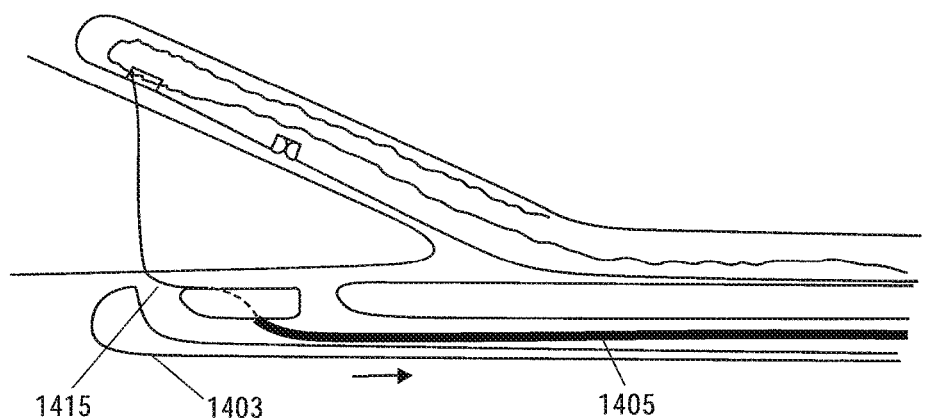
Figure 48F:
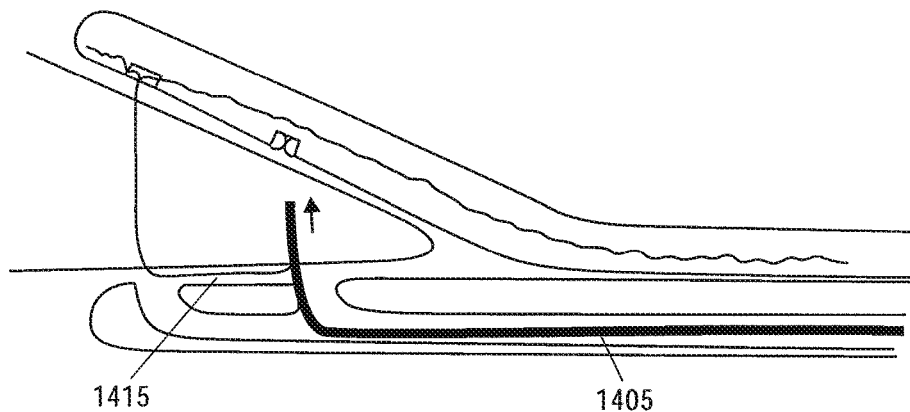
Figure 48G:
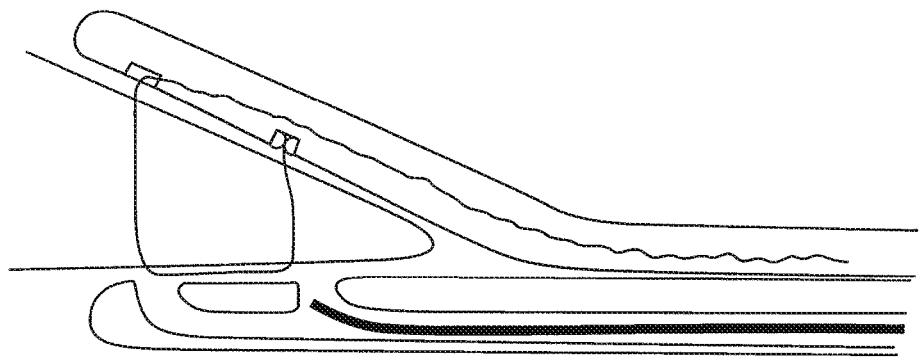
Figure 48H:
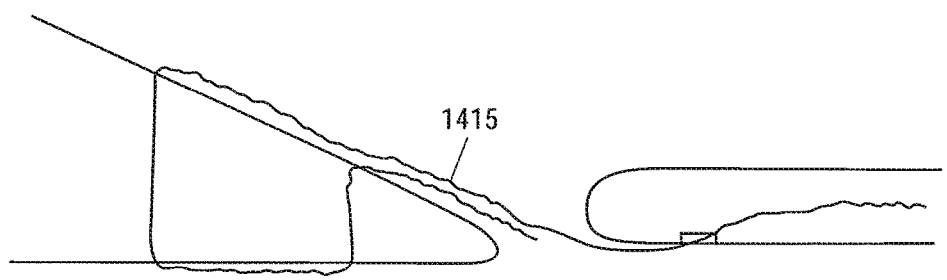
Figure 48I:
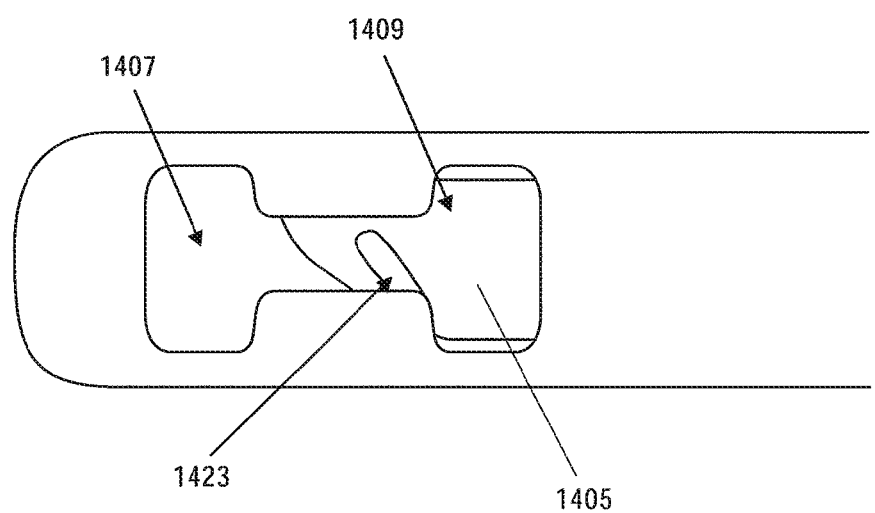
FIG. 48I shows an enlarged top view of the lower arm of the suture passer of FIG. 48A.

In FIG. 48E the tissue penetrator 1405 is shown retracted back into the lower arm 1403; the attached suturing element 1415 is drawn back with the tissue penetrator, and can pass through an open channel in the lower arm (visible in FIG. 48I). As the pre-biased tissue penetrator is drawn proximally relative to the lower arm, as shown in FIG. 48F, the distal tip of the tissue penetrator will extend towards the proximal exit in the lower arm 1409. This distal tip of the tissue penetrator may be restrained by the lower arm until it passes the opening forming the proximal exit 1409. In some variations, entering this opening may be felt by the user, or the device may include an indicator that tells when the tissue penetrator is again ready to be sent through the meniscus.

In FIG. 48F, the tissue penetrator is advanced distally to send it out of the lower arm and through the meniscus in a predetermined pathway so that it can transfer the suture 1415 to a suturing element dock 1421 on the opposite arm, as shown in FIG. 48C. Thereafter, the suture can be retained in the dock (actively or passively) and the tissue penetrator retracted back into the lower arm. Finally, the meniscus suture passer can be retracted, in some variations by retracting the lower arm proximally and then withdrawing the upper arm away from the meniscus, as shown in FIG. 48H the suturing element (in this example, a suture 1415 can be left behind. As mentioned above, in some variations a pre-tied knot may be included at one end of the suture. In FIG. 48H, the suture (including pre-tied knot) may be held within or against the upper arm of the suture passer, and the meniscus suture passer may be adapted to help push and secure the knot (not shown).

FIG. 48I shows an enlarged top view of the distal region of the lower arm 1403, showing the distal 1407 and proximal 1409 exits for the tissue penetrator, as well as a connecting suture channel between the two. The distal end region of a tissue penetrator 1405 is partially visible through the suture channel and proximal exit, showing the hooked region for retaining the suturing element 1423.

FIGS. 49 and 50A-50L illustrate another variation of a meniscus suture passer having a single tissue penetrator that is configured to extend from the lower jaw in a distinct proximal and distal pathway to form a radial loop stitch around the meniscus. This example is similar to the previously described variations, and is shown adapted for passing a suture directly, without the use of an additional suture puller or suture shuttle.

Figure 49:
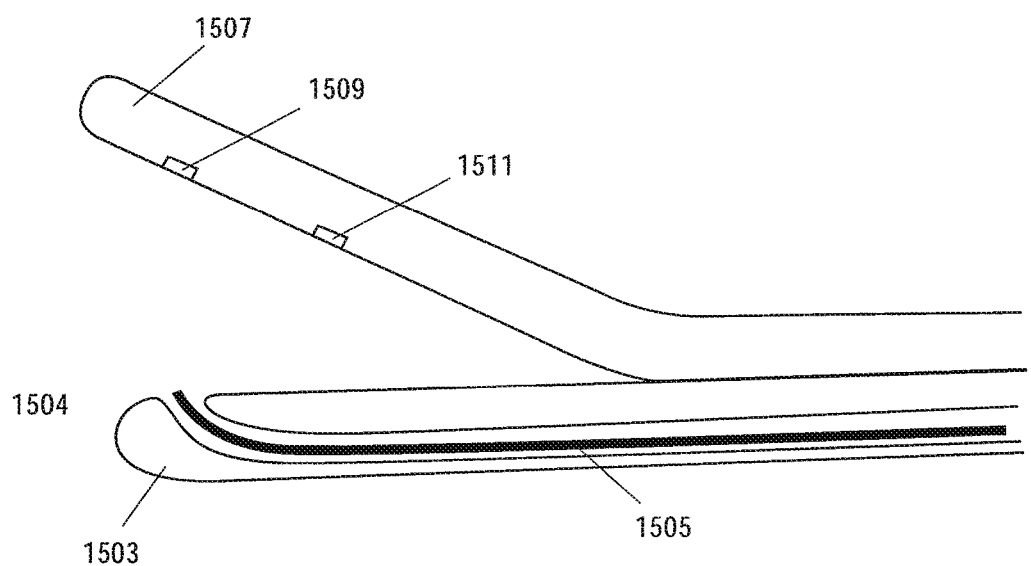
FIG. 49 shows the distal end region of another variation of a suture passer in partial cross-section.

FIG. 49 shows a partial longitudinal section through the distal end of the meniscus suture passer. In this example, the device includes a longitudinally movable 1504 lower arm (or jaw) 1503 which contains a tissue penetrator 1505. The opposite ("upper") arm 1507 includes a distal suture dock 1509 and a proximal suture dock 1511. In this example, the distal suture dock is pre-loaded with a suture (not visible in FIG. 49).

Figure 50A:
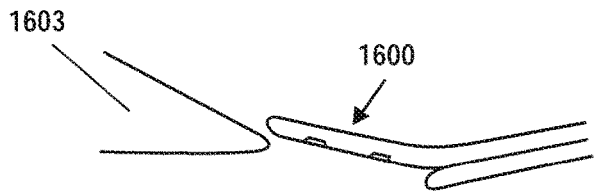
FIGS. 50A-50L illustrate operation of the suture passer of FIG. 49.
Figure 50B:
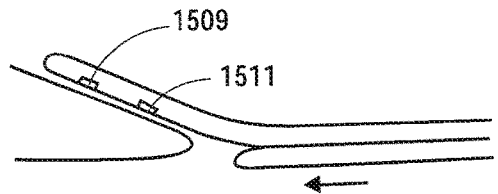
Figure 50C:

Operation of the exemplary meniscus suture passer is illustrated in FIGS. 50A-50L, including the somewhat generic positioning and withdrawal steps. For example, in FIG. 50A the suture passer 1600 is shown in a delivery configuration in which the lower arm is retracted so that the device does not have any "branches" which might may it difficult to insert into a minimal opening into the region around the meniscus 1603. The distal end of the device (the distal end of the upper arm) is then positioned near the meniscus from an apical (inside-out) approach, and this upper arm is slid over the femoral surface of the meniscus, as shown in FIG. 50B. Once the upper arm is positioned along or adjacent to the femoral surface of the meniscus 1603, the lower arm can then be extended distally, forming an acutely angled opening at the distal end of the suture passer device, and partially surrounding the meniscus from around the apical end on both the femoral and tibial surfaces of the meniscus, as shown in FIG. 50C.

Figure 50D:
Figure 50E:
Figure 50F:
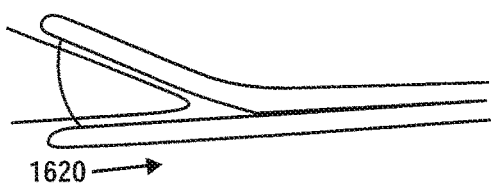
Figure 50G:
Figure 50H:
Figure 50I:
Figure 50J:
Figure 50K:
Figure 50L:

The suture passer 1600 configuration shown in FIG. 50C may be referred to for simplicity as the first deployed configuration. In this configuration the tissue penetrator may be extended through the meniscus transversely to the longitudinal axis of the suture passer (and between the two arms) to engage a suture within the distal suture dock 1509, as shown in FIG. 50D. Once the loop of suture is captured by the tissue penetrator, the tissue penetrator may be pulled back down into the lower arm, withdrawing the suture though the meniscus along the first path, as shown in FIGS. 50E and 50F. As indicated by the arrow 1620 in FIG. 50F, the lower arm may then be retracted proximally until it reaches a predetermined set position as shown in FIG. 50G, leaving the suture passer in a second deployed configuration. Detents, stops, or other indicators (tactile, visual, or other) may indicate when the suture passer is in the correct position (e.g., the delivery configuration, the first deployed configuration, the second deployed configuration, etc.). From the second deployed configuration, the tissue penetrator 1505 can again be extended distally to pass through the meniscus and between the upper and lower arms, pulling the suture, as shown in FIG. 50H. In this example, the proximal path through the meniscus is distinct from the distal path; the suture is released from the tissue penetrator, and may be tentatively held by the proximal dock in the upper jaw until the suture passer is withdrawn, as shown in FIGS. 50K and 50L. The suture passer may be withdrawn by retracting the lower arm to return to the delivery configuration, as shown in FIG. 50K.

PART II: MULTIPLE TISSUE PENETRATORS

In some variations of the meniscus suture passers described herein two or more tissue penetrators may be used to simultaneously or sequentially pass (push/pull, etc.) suturing elements through the meniscus. In many of these variations the overall configuration of the suture passer may be similar to those described above, including the movable lower/upper arms, the elongate body, and the like. In some variations the same tissue penetrators may be used, as illustrated in the exemplary tissue penetrators shown in FIGS. 52A and 52B, which may be used with the device shown in FIG. 51.

FIG. 51 shows a partial longitudinal section through one variation of a suture passer 1700 having two parallel tissue penetrators 1701, 1703 that may be used to pass a single suture 1705 (e.g., by pulling on opposite ends of the suture) to pass a complete loop (e.g., radial loop) around the meniscus. This is illustrated in FIGS. 53A-53G.

Figure 53A:
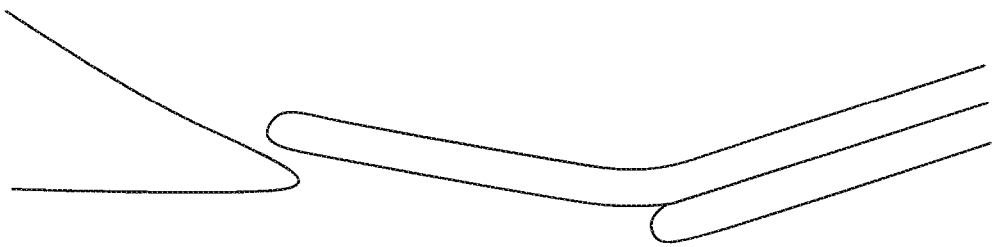
FIGS. 53A-53G illustrate operation of the meniscus suture passer of FIG. 51.
Figure 53B:
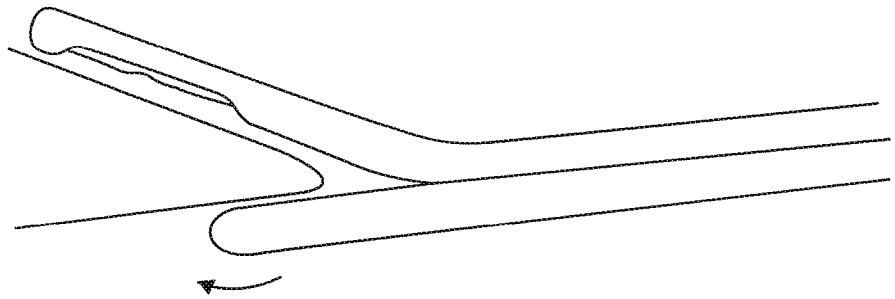
Figure 53C:
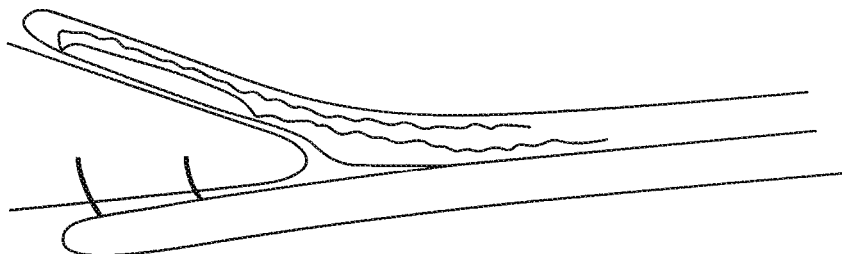
Figure 53D:
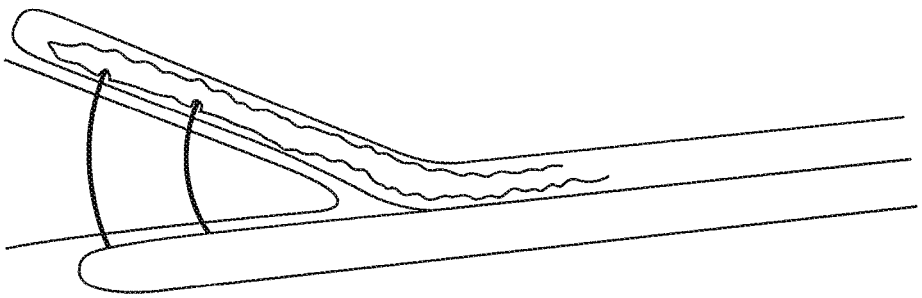
Figure 53E:
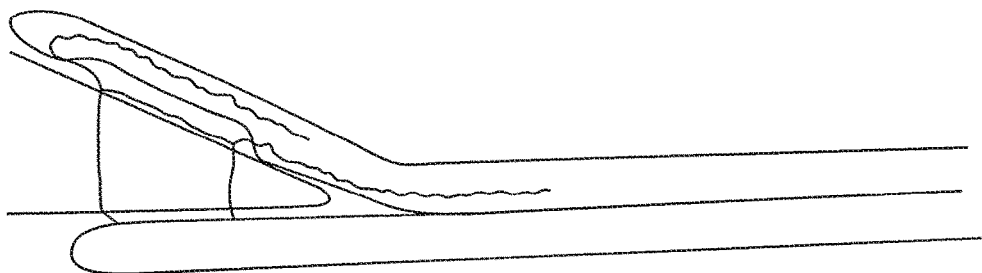

For example, in FIG. 53A, the meniscus suture passer of FIG. 51 is shown approaching a meniscus in a delivery configuration in which the lower arm is retracted proximally. After positioning the upper arm against the tibial surface of the meniscus, as shown in FIG. 53B, the lower arm is extended to a fully deployed configuration in which the acute opening formed at the distal end of the suture passer partially surrounds the meniscus. In FIG. 53C, both of two tissue penetrators are shown simultaneously extending through the meniscus; in some variations the tissue penetrators may be extended sequentially, rather than simultaneously. If the tissue penetrators are simultaneously extended, the device may be adapted to accommodate the slightly shorter pathway experienced by the more proximal tissue penetrator.

Figure 53F:
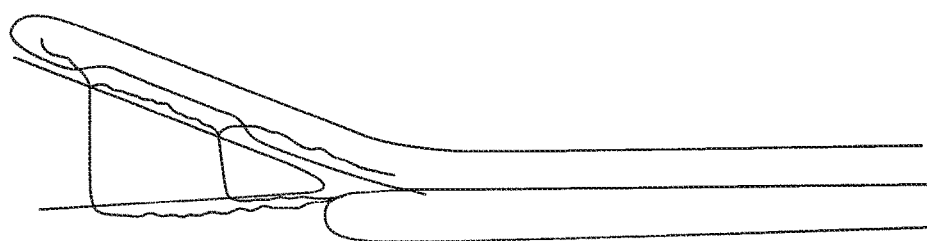
Figure 53G:
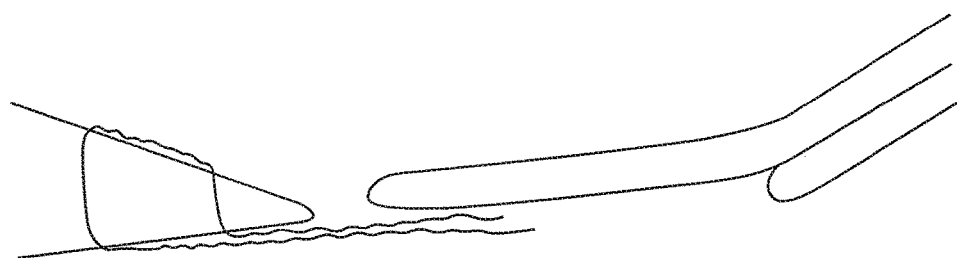
Figure 55:
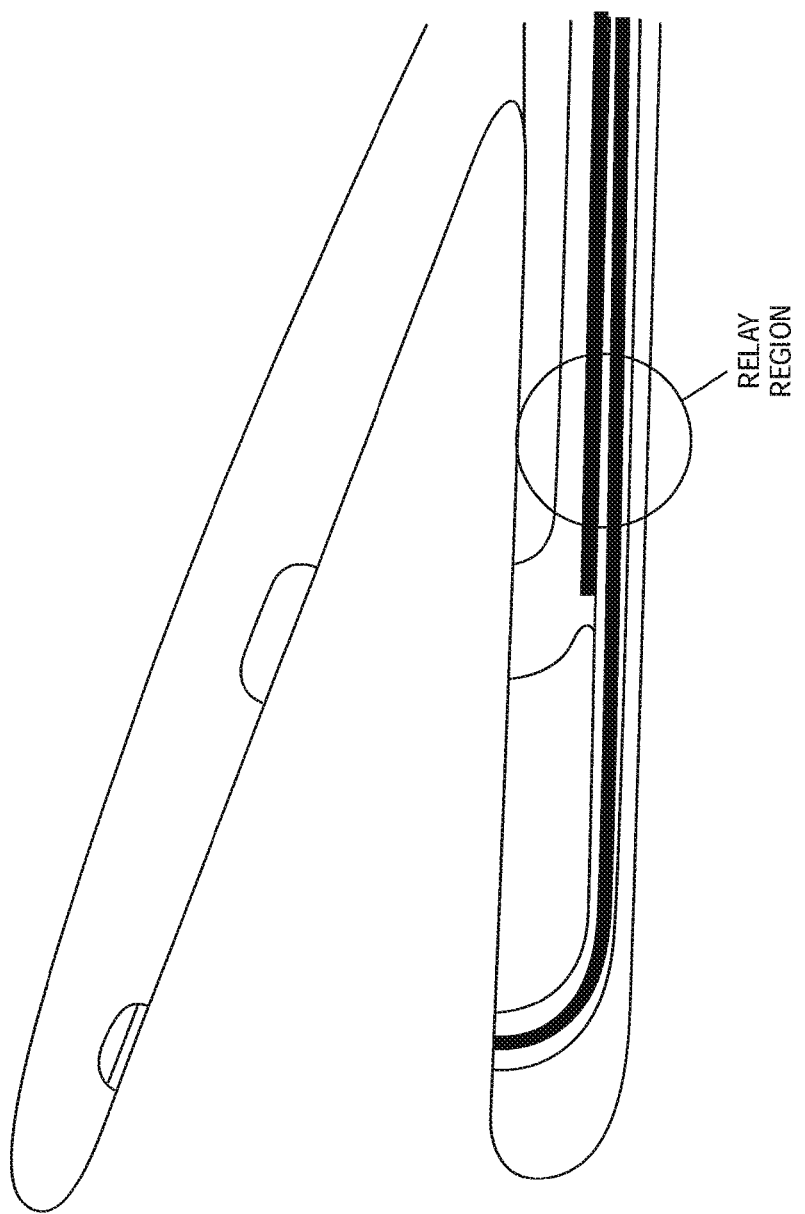
FIG. 55 shows another variation of a suture passer having two tissue penetrators and configured so that the first tissue penetrator hands off a suturing element to a second tissue penetrator during operation.

Both tissue penetrators may engage a suture held in a dock region (shown as a single large dock region in FIGS. 51 and 53A-53G, although two discrete dock regions may be used and in some variations connected by a suture channel. For example, the sutures may be hooked onto the tissue penetrators. Thereafter, the suture passer may be withdrawn by retracting the lower arm, then removing the device from around the meniscus, leaving the free ends of the suture on the tibial side of the meniscus, as shown in FIGS. 53F and 53G. The suture may then be knotted and/or tied off.

In this example, the suture ends are terminated on the tibial (as opposed to femoral) side of the meniscus. As mentioned above, any of the variations described herein may be adapted so that the ends of the suture may be terminated (and therefore knotted, etc.) on either the femoral or tibial side; for example, although the tissue penetrator is shown (for convenience) contained and extending from the lower arm, this may be reversed so that the tissue penetrator is contained and extends from the upper arm.

FIGS. 54A-54C illustrates another variation of a suture passer device having a pair of tissue penetrators that extend across the meniscus; in this variation the suturing element is passed from one tissue penetrator to the other, and thus a "hand off" is made between the two. For example, in FIG. 54A a first tissue penetrator and a second tissue penetrator are located in the lower arm. The first tissue penetrator may be pre-loaded with a suture. In FIG. 54B, the first tissue penetrator with the pre-loaded suture is advanced through the meniscus into the upper arm; in FIG. 54C the second tissue penetrator is advanced distally to extend through the meniscus into the upper arm, where it is deflected so that engages the distal end region of the first tissue penetrator while within the upper arm and the suturing element is transferred from the first tissue penetrator to the second tissue penetrator. The second tissue penetrator is then withdrawn proximally and back through the meniscus, pulling the suture with it.

FIGS. 54D and 54E show the first tissue penetrator and the second tissue penetrator, respectively. The first tissue penetrator includes a distal end region around and outer edge of which a suturing element (shown as a suture in FIG. 54D) may be wrapped; the distal end includes an opening or channel into which the second tissue penetrator may engage to receive the suturing element. The hook region formed by the distal end of the second tissue penetrator therefore receives the suturing element.

FIGS. 55 and 56A-E illustrate another variation of a meniscus suturing device having a pair of tissue penetrators that are configured to exchange a suture as the meniscus is sutured through two or more regions. For example, in FIG. 55, the lower jaw includes a pair of tissue penetrators which are illustrated in greater detail in FIGS. 56D and 56E, and shown in operation in FIGS. 56A-56C. For example, in FIG. 55, the first and second tissue penetrators are arranged so that they may be slid relative to each other and thereby exchange a suturing element between the two. The first tissue penetrator (e.g., such as the one shown in FIG. 56D) is configured (as described above) to extend from a distal exit on the lower arm and extend through a meniscus to engage a suture element on the upper arm and pull it back through to the lower jaw. As the first tissue penetrator is retracted within the lower arm proximally it may engage the second tissue penetrator (such as the one shown in FIG. 56E). For example, in FIG. 56A the lower (first) tissue penetrator is pulled proximally; as it nears the second tissue penetrator within the relay region shown in FIG. 55, the suture 2201 is driven laterally (up in FIG. 56A), so that it can align with the opening of the second tissue penetrator, as shown in FIG. 56B. For example, a deflector, mandrel, or the like 2203 may be used to guide the suture loop 2201 from the first tissue penetrator into the second tissue penetrate. This second tissue penetrator may then be driven distally to extend through the tissue and engage with a suturing element dock on the opposite arm.

PART III: CURLED NEEDLES

In some variations, the suturing devices described herein may be configured as a double passing, single exchange device. Such devices may include a tissue penetrator that is preloaded with a suturing element and is configured to extend from a first arm of the suture passer device, though the tissue, bend around (e.g., through 180 degrees of turn) and return to the same arm of the suture passer, but at a laterally displaced position, where the suturing element is dropped off, so that the tissue penetrator can then be retracted back through the meniscus leaving the passed suture behind.

Figure 57:
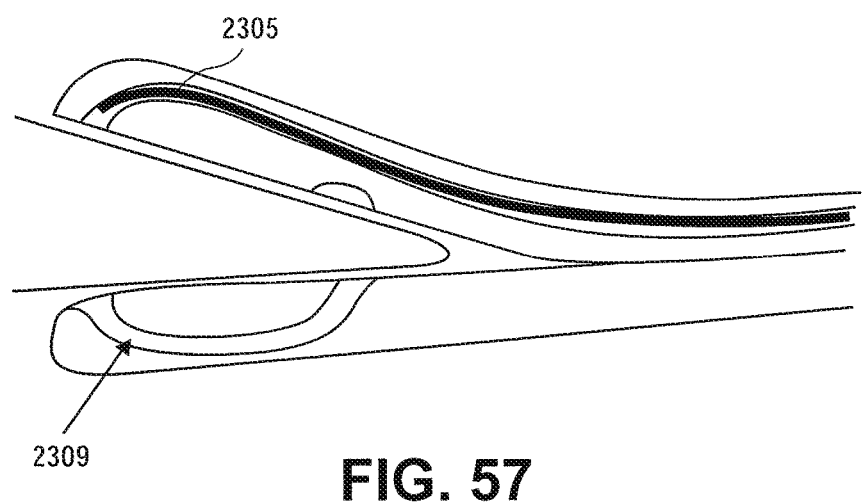
FIG. 57 shows another variation of a meniscus suture passer.
Figure 59A:
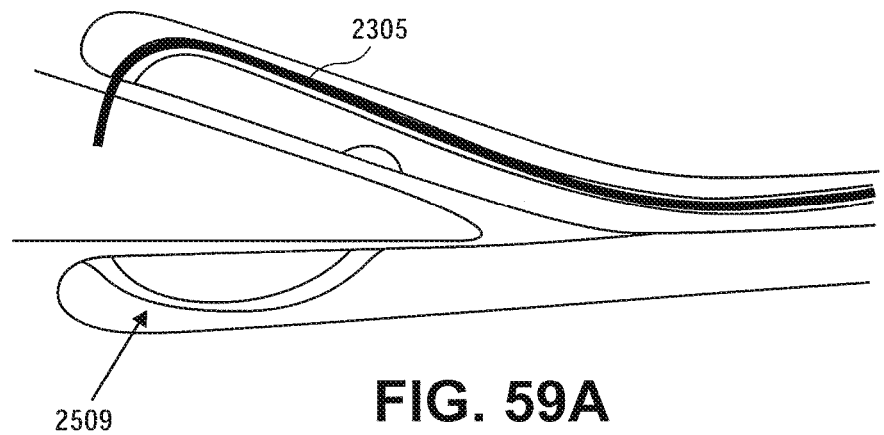
FIGS. 59A-59F illustrates operation of the meniscus suture passer shown in FIG. 57.
Figure 59B:
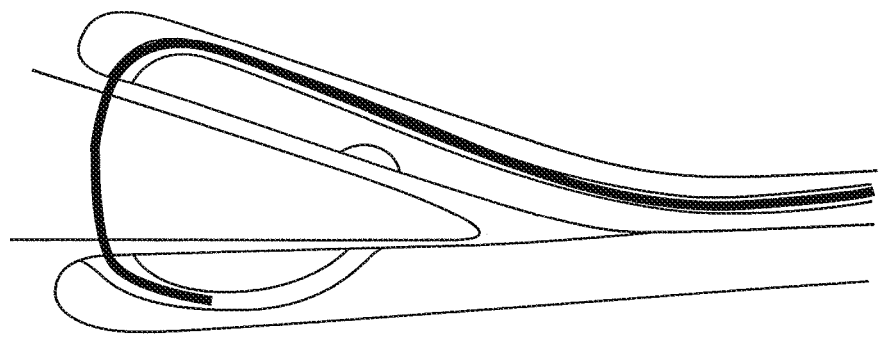
Figure 59C:
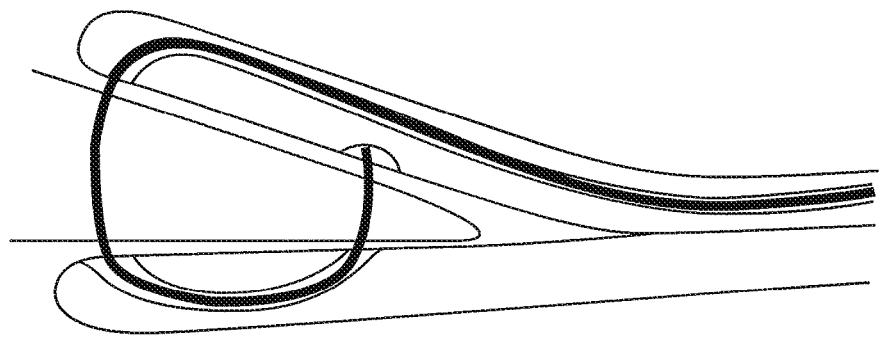
Figure 59D:
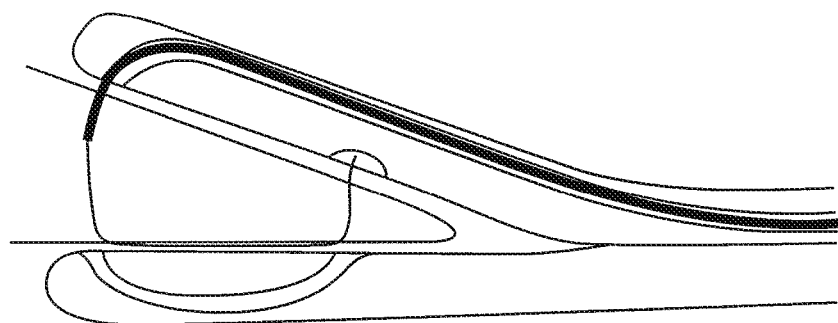
Figure 59E:
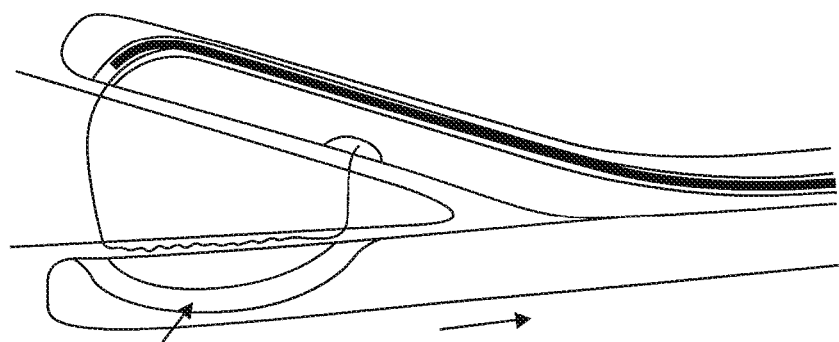
Figure 59F:
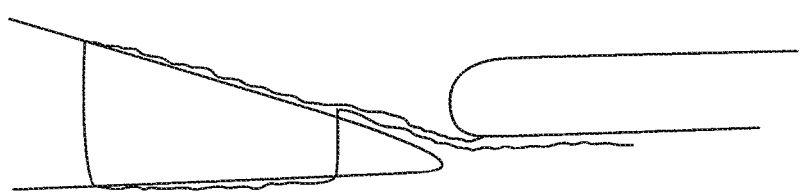

One variation of this device is shown in FIG. 57. In this example, the upper and lower arms may be configured as described above, with the tissue penetrator 2305 (e.g., made of a shape memory alloy) is held within the upper arm. The lower arm includes a channel 2309 to receive the tissue penetrator and steer it to a laterally-displaced position where it again crosses the meniscus to engage a dock back on the upper arm. The lower arm in this variation may protect the surrounding tissue by guiding the tissue penetrator and preventing it from damaging adjacent tissues. FIGS. 59A-59F illustrate operation of this variation. In FIG. 59A, once the arms of the suturing device have been positioned around the meniscus as described previously, the tissue penetrator can be driven distally and pushed through the meniscus. In FIG. 59B, the tissue penetrator (with attached suture) is shown being deflected by a deflection region on the lower arm so that it is guided through the lower arm and then out of the lower arm to extend back through to the upper arm where the distal end of the tissue penetrator with the attached suture can engage a suture dock on the upper arm, as shown in FIG. 59C. As shown in FIG. 59D, after leaving the suture in the suture dock, the tissue penetrator can be withdrawn back through the tissue into the upper arm. The device may then be retracted from the tissue (e.g., by retracting the lower arm proximally and then removing the device, as shown in FIGS. 59E and F).

Other variations similar in operation to those shown in FIG. 59A-59F are illustrated in FIGS. 59G1 and 59G2, FIGS. 59H1 and 59H2, and FIGS. 59i1 and 59i2. The path taken by the suture passer 2305 (and thus an attached suturing element) through the meniscus is guided by the suture passer. In some variations (e.g., FIGS. 59G1-59G2) the suturing element passes from the top (femoral) surface of the meniscus and loops down to the tibial surface and back up to the femoral surface; in other variations the suturing element passes from the bottom (tibial) surface up to the femoral surface and back down to the tibial surface. Thus a suture loop may be tied off on either the tibial or femoral side. Further, in some of the variations illustrated above (e.g., FIGS. 59A-59F and FIGS. 59i1-59i2, the suture passer is configured so that the tissue penetrator penetrates the thicker distal region of the meniscus first; in FIGS. 59G1-

59G2 and FIGS. 59H1-59H2 the suture passer is configured so that the tissue penetrator penetrates the thinner (e.g., more apical) region of the meniscus first. Any of these variations could be configured so that the suturing element is either pushed or driven through the meniscus by the tissue penetrator because the suturing element is pre-loaded onto the tissue penetrator; alternatively the variations could be configured so that the suturing element is pulled through the meniscus as the tissue penetrator is withdrawn back through the meniscus.

Figure 58:
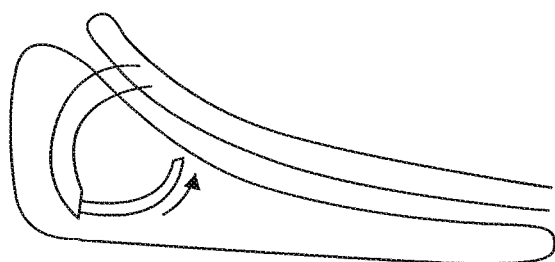
FIG. 58 shows another variation of a meniscus suture passer.

In some variations the tissue penetrator is a single tissue penetrator. As mentioned, it may be pre-bent or biased to extend around after leaving the first arm of the suture passer. Thus, in some variations a second arm of the suture passer may not be necessary; however the second arm may be particularly useful for deflecting the tissue penetrator as illustrated above. FIG. 58 illustrates another variation of a suture passer, in which the tissue penetrator is a compound tissue penetrator, having a telescoping member that may extend to increase the turn radius and/or length of the tissue penetrator.

In some variations the device may be configured to allow a user (e.g., surgeon) to determine how big of a stitch to create with the device. For example the device may include a control (or controls) configured to adjust the axial location of the curves guiding the needle. For example, in FIGS. 59A-59E the lower arm of the meniscus suture passer includes a channel 2509 that guides the tissue penetrator laterally before it exits the lower arm to again cross the meniscus. In some variations the channel shape or size (e.g., lateral extent) may be adjustable from the proximal handle, helping determine where the needle exits the lower arm to cross the meniscus. In some variations the upper arm may include multiple, laterally displaced docks to receive the tissue penetrator and/or suture element, or one or more docks configured to receive the tissue penetrator/suture element from a variety of lateral positions.

Figure 59J:
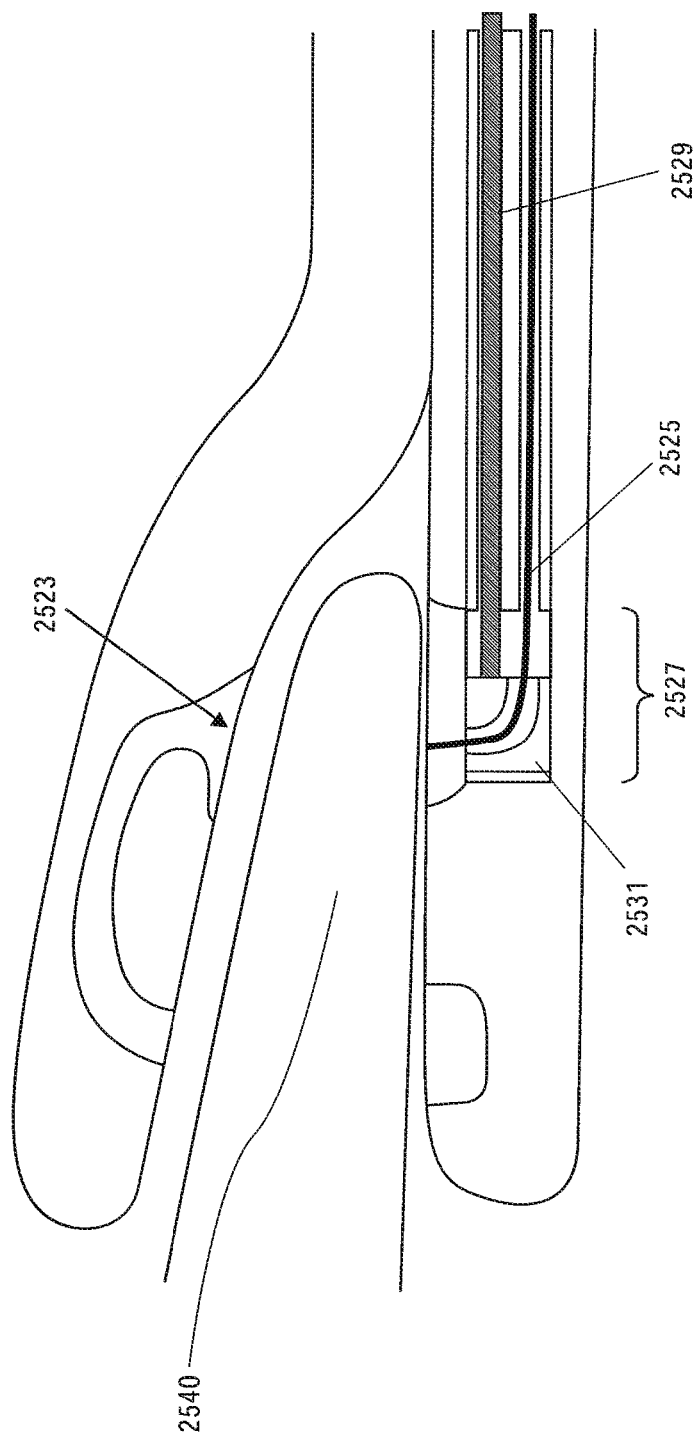
FIG. 59J illustrates another variation of a meniscus suture passer similar to those shown in FIGS. 59A-59*i*2, configured to have an adjustable suture loop size.

For example, FIG. 59J illustrates one variation in which separation between the first and second stitch through the meniscus is adjustable, and thus the size of the loop through the meniscus 2540 is adjustable. In this example, the lower arm includes a tissue penetrator that is guided at the distal end within the lower arm by a slider 2529 attached to a guide block 2531. The slider 2529 may be moved proximally and distally within a window 2527 to select the width of the stitch/loop. In this example, the slideable block 2531 includes a bending channel region to redirect and guide the tissue penetrator from the lower arm to the upper arm and through the meniscus 2540. The upper arm includes either a lead-in region 2533 to accommodate tissue penetrators approaching from a range of directions, depending upon the slider position of the lower arm. The slider 2529 includes a shaft or other control for controlling the position of the block 2531 within the window 2527 of lateral positions for the exit of the tissue penetrator 2525.

In general, any of the suture passers described herein may be configured to protect the non-target tissues around the meniscus, and particularly the chondral surfaces in the joint, as well as the capsule region. For example, in any of the variations of meniscus suture passers described herein, the tissue penetrators are configure so that they are contained within the boundaries of upper and lower arms; in general, the tissue penetrator(s) follow a predetermined pathway between upper and lower arms and do not extend vertically (e.g., beyond the upper or lower arms). The tissue penetrating distal tip of the tissue penetrator is generally secured within (e.g., entirely within) the upper and/or lower arms, except when being extended between the arms. This control of the tissue penetrator(s) may enhance the ease of use and safety of the device.

PART IV: STAPLING SUTURE PASSERS

In some variations, the meniscus suturing devices described herein may be configured to pass two or more tissue penetrating elements that are connected by a suturing element and thereby "staple" the tissue. In this example, two tissue penetrating elements connected by a suture are driven through the meniscus from one side to the opposite side. The tissue penetrating elements may be left behind, while connected by the suture.

PART V: ADDITIONAL FEATURES

As mentioned, various additional features may generally be included or implemented as part of any of the suture passers described herein. Some of these features are illustrated in FIGS. 60A-61D.

Figure 60A:
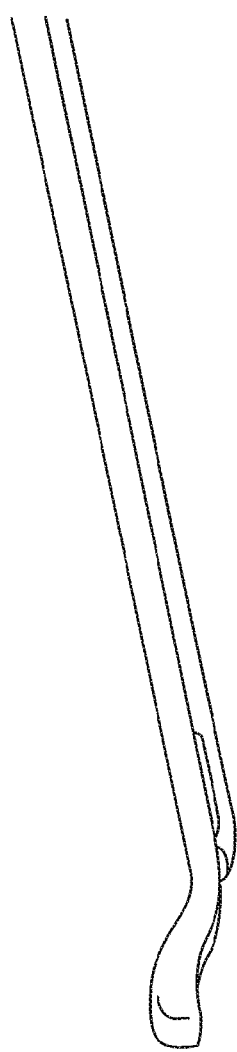
FIGS. 60A and 60B show perspective views of portions of a suture passer.
Figure 60C:
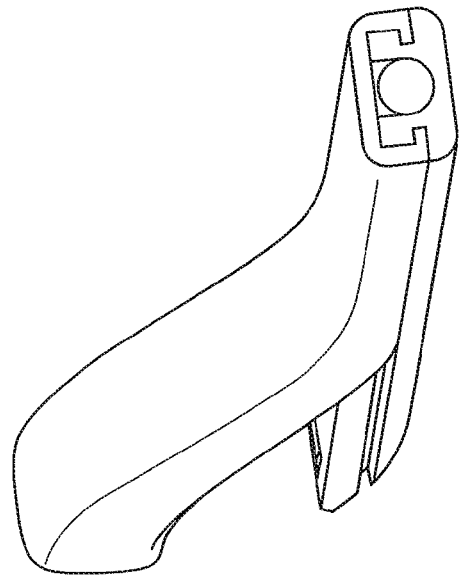
FIG. 60C shows a perspective view of another variation of a suture passer.
Figure 60B:
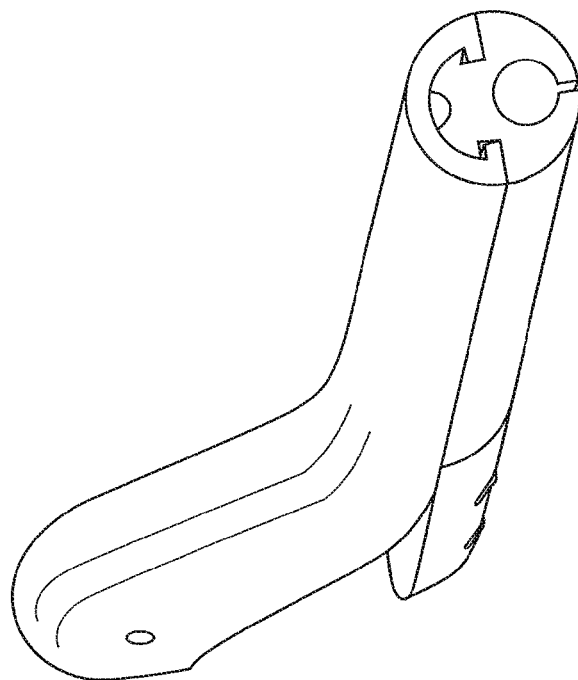

For example, FIGS. 60A-60C illustrate profiles of the upper and lower arms in some variations of the suture passers described herein. FIG. 60A shows a variation in which the elongate body of the suture passer is tubular (e.g., has a round or oval cross-section), so that the upper arm and lower arm are slideably disposed, and each is approximately semi-circular. In some variations it may be beneficial to reduce the height or thickness of the upper and/or lower arms. One variation, shown in FIG. 60C is configured so that the upper arm and lower arm are rectangular and somewhat nested. In this example the upper arm partially surrounds the lower arm while still allowing sliding. The overall height of the device and particularly the individual upper and lower arms has thus been reduced.

Any of the variations described herein may be used with a suture shuttle or without. FIGS. 61A-61D illustrate a variation in which the tissue penetrator includes a clip or snap region onto which a suture shuttle (e.g., ring-type shuttle) can attach. In FIG. 61A, the distal end of the tissue penetrator is shown with an attached shuttle within a dock. The distal end of the tissue penetrator, including the shuttle engagement region, is shown in FIG. 61B. FIGS. 61C and 61D illustrate different variations of tissue penetrators.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the invention.

Although the description above is broken into parts and includes specific examples of variations of suture passers, any of the features or elements described in any particular example or section may be incorporated into any of the other embodiments. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of arthroscopically placing a suture around a portion of meniscus without penetrating a meniscocapsular region of the meniscus, the method comprising using a suture passer to pass a suture along an inferior meniscus surface and between the inferior meniscus surface and a tibia, through the meniscus, along a superior meniscus surface between the superior meniscus surface and a femur, and through the meniscus again.

2. The method of claim 1 comprising entirely arthroscopically placing the suture.

3. The method of claim 1, wherein placing the suture comprises extending a tissue penetrating element in an arcuate pathway through the meniscus.

4. The method of claim 1, further comprising approaching the meniscus from an apex of the meniscus.

5. The method of claim 1, further comprising minimally invasively positioning a distal end of the suture passer near an apex of the meniscus before passing the suture.

6. The method of claim 1, further comprising minimally invasively entering a knee joint with the suture passer from an anterior approach.

7. The method of claim 1 further comprising: extending a first arm of the suture passer into a space between the superior surface of the meniscus and the femur; extending a second arm of the suture passer into a space between the inferior surface of the meniscus and the tibia; and passing the suture between the first arm and second arm of the suture passer.

8. The method of claim 1, further comprising: extending a first arm of the suture passer into a space between the inferior surface of the meniscus and the tibia; extending a second arm of the suture passer into a space between the superior surface of the meniscus and the femur; and passing the suture between the first arm and second arm of the suture passer.

9. The method of claim 1 further comprising:
coupling two ends of the suture so as to form a suture loop around the portion of meniscus.

10. The method of claim 1 wherein passing the suture along the inferior meniscus comprising passing the suture radially along the meniscus.

11. A method of arthroscopically placing a suture around a portion of a meniscus without penetrating a meniscocapsular region of the meniscus, the method comprising:
minimally invasively positioning a distal end of a suture passer near an apex of the meniscus; and then
using the suture passer, passing a suture along a superior meniscus surface and between the superior meniscus surface and a femur, through the meniscus, along an inferior meniscus surface between the inferior meniscus surface and a tibia, and through the meniscus again.

12. The method of claim 11 comprising entirely arthroscopically placing the suture.

13. The method of claim 11, wherein placing the suture comprises extending a tissue penetrating element in an arcuate pathway through the meniscus.

14. The method of claim 11, further comprising approaching the meniscus from the apex of the meniscus.

15. The method of claim 11, further comprising minimally invasively entering a knee joint with the suture passer from an anterior approach.

16. The method of claim 11 further comprising: extending a first arm of the suture passer into a space between the superior surface of the meniscus and the femur; extending a second arm of the suture passer into a space between the inferior surface of the meniscus and the tibia; and passing the suture between the first arm and second arm of the suture passer.

17. The method of claim 11, further comprising: extending a first arm of the suture passer into a space between the inferior surface of the meniscus and the tibia; extending a second arm of the suture passer into a space between the superior surface of the meniscus and the femur; and passing the suture between the first arm and second arm of the suture passer.

18. The method of claim 11 further comprising:
knotting two ends of the suture so as to form a suture loop around the portion of meniscus, the two ends of the suture knotted at the superior meniscus surface.

19. The method of claim 11 wherein passing the suture along the superior meniscus and inferior meniscus comprise passing the suture radially.

* * * * *